United States Patent [19]
Sugai et al.

[11] Patent Number: 5,945,404
[45] Date of Patent: Aug. 31, 1999

[54] 21-SUBSTITUTED STEROID COMPOUND

[75] Inventors: Kei Sugai, Kawagoe; Motoaki Goto, Higashikurume; Satoshi Yoshida, Tokorozawa; Yumiko Noda, Tachikawa; Takayuki Ishii, Kawagoe; Nobuyuki Kibushi, Iruma; Hutoshi Nishikawa, Tokorozawa, all of Japan

[73] Assignee: Nissin Shokuhin Kabushiki Kaisha, Osaka, Japan

[21] Appl. No.: 08/927,399

[22] Filed: Sep. 10, 1997

Related U.S. Application Data

[63] Continuation of application No. 08/604,969, filed as application No. PCT/JP94/01602, Sep. 28, 1994, abandoned.

[30] Foreign Application Priority Data

Sep. 29, 1993 [JP] Japan ................................. 5-243123

[51] Int. Cl.$^6$ ............................. A61K 31/705; C07J 5/00; C07J 7/00; C07J 9/00
[52] U.S. Cl. ................................. 514/26; 536/5; 536/18.6
[58] Field of Search ............................. 514/26; 536/18.5, 536/18.6, 5

[56] References Cited

U.S. PATENT DOCUMENTS

| | | | |
|---|---|---|---|
| 3,185,682 | 5/1965 | Sarett et al. | 260/239.55 |
| 3,240,777 | 3/1966 | Sarett et al. | 260/239.55 |
| 3,427,300 | 2/1969 | Sarett et al. | 260/210 |

FOREIGN PATENT DOCUMENTS

| | | |
|---|---|---|
| 123 485 | 10/1984 | European Pat. Off. . |
| 3627 | 10/1965 | France . |
| A-60-501105 | 7/1985 | Japan . |
| 1015396 | 12/1965 | United Kingdom . |
| 1059548 | 2/1967 | United Kingdom . |
| WO 84/04041 | 10/1984 | WIPO . |
| WO 93/22334 | 11/1993 | WIPO . |
| WO 94/15947 | 7/1994 | WIPO . |

OTHER PUBLICATIONS

The Merck Index, 12$^{th}$ Edition, 1996, Therapeutic Category and Biological Activity Index, p. Ther–22.
Tozer et al., *Pharm. Res.*, vol. 8(4): 445–454, (1991)(Abstract only).
*Monosaccharides: Their Chemistry And Their Roles In Natural Products*, ed. Collins & Ferrier, (John Wiley & Sons), p. 4 (1995).
The Merck Index (Eleventh Edition), pp. 184, 463, 464, 494–496 (1989).
Journal of Medicinal Chemistry, vol. 27, No. 3, Mar. 1984, "A Colon–Specific Drug Delivery System Based on Drug Glycosides and the Glycosidases of Colonic Bacteria", David R. Friend et al., pp. 261–266.
Journal of Medicinal Chemistry, vol. 28, No. 1, Jan. 1985, "Drug Glycosides: Potential Prodrugs for Colon–Specific Drug Delivery", David R. Friend et al., pp. 51–57.
J. Am. Chem. Soc. (1964), vol. 86, Sep. 20, 1964, 3903–3904.
J. Pharm. Pharmacol. vol. 43 (1991), "Relative anti–inflammatory effect of oral dexamethasone–β–D–glucoside and dexamethasone in experimental inflammatory bowel disease in guinea pigs", D.R. Friend et al., pp. 353–355.

*Primary Examiner*—Howard C. Lee
*Attorney, Agent, or Firm*—Oliff & Berridge, PLC

[57] ABSTRACT

A glycoside represented by formula (I), wherein dexamethasone or betamethasone is the aglycon and the 21-position is substituted by a simple sugar or an acylated sugar selected from the group consisting of glucose, galactose, mannose, rhamnose, fucose, N-acetylglucosamine, N-acetylgalactosamine, galacturonic acid, glucuronic acid and sialic acid.

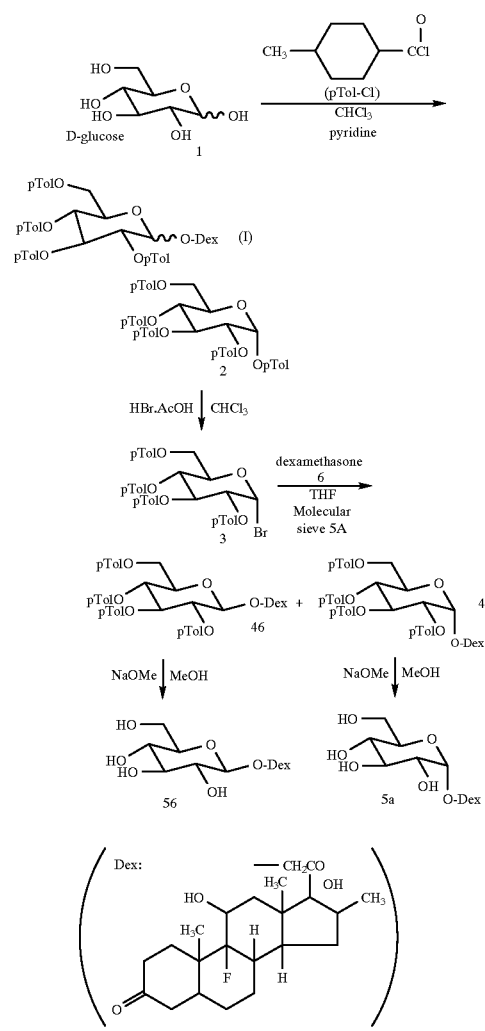

21 Claims, 27 Drawing Sheets

21-SUBSTITUTED STEROID COMPOUND

This is a Continuation of application Ser. No. 08/604,969 filed Mar. 20, 1996, now abandoned, which in turn is a U.S. National Stage Application of PCT/JP94/01602 filed Sep. 28, 1994.

FIELD OF THE INVENTION

This invention relates to novel steroidal compounds substituted at position-21 with simple sugars or acylated derivatives of said simple sugars.

BACKGROUND OF THE INVENTION

Development of sugar-steroid compounds which have no steroidal activities themselves, but can be converted to the active forms by glucosidases which increase at the inflammatory site of rheumatism or the like have been reported by the research group of Merck & Co. [J. Am. Chem. Soc. (1964), 86, 3903–4, FR3627 (1965) and GB1015396 (1965)].

Several steroid derivatives aimed to reduce toxicity were also synthesized. For example, a sugar-steroid compound capable of specifically reaching the colon was reported (Japanese Patent Laid-open Publication, Sho60-501105 (WO8404041), J. Pham. Pharmacol. (1991), 43, 353–5, WO9415947 (disclosed on Jul. 21, 1994) and WO9322334 (disclosed on Nov. 11, 1993).

Although the unfavorable side-effects were somewhat reduced in the sugar-steroid compounds described in the aforementioned literatures, but still not sufficiently, requiring further improvement.

Inventors of the present invention actually synthesized glycosyl steroid derivatives wherein simple sugars or said simple sugars with hydroxyl groups thereof modified with acetyl groups were linked to steroids, and examined their pharmacological activities, confirming that side-effects of these derivatives were about the same as those of the aglycon steroids, and actually not sufficiently reduced probably because they might be readily hydrolyzed by glucosidases usually omnipresent within living body to release the aglycon steroids.

DISCLOSURE OF THE INVENTION

The present invention was made in view of the aforementioned problems, aiming to provide sugar-steroid compounds with significantly reduced unfavorably side-effects.

In order to resolve the above-mentioned problems, the present invention features the modification of hydroxyl groups of simple sugar component of sugar-steroid compounds with sterically bulky protective groups, more specifically, toluoyl (ortho-, meta-, or para-methylbenzoyl), benzoyl, p-chlorobenzoyl or arylalkyl (e.g., benzyl) groups.

By the introduction of these bulky protective groups, the resulting sugar-steroid compounds are rendered more resistant to endogenous glycosidases omnipresent in living body, releasing the active aglycon (steroid) only after the cleavage action of glycosidases which are known to increase at the inflammatory site. Therefore, glycosylsteroid derivatives of the present invention are able to exert anti-inflammatory effect without showing unfavorable side-effects on the non-inflammatory sites. Furthermore, this effect is also achieved by limiting simple sugars to be used to those not present or almost not present in living body (e.g., fucose and rhamnose).

That is, glycosylsteroid derivatives of the present invention are glycosides of the aglycon steroids which are substituted at position-21 with simple sugars or acylated simple sugars with hydroxyl groups thereof protected with toluoyl, benzoyl, p-chlorobenzoyl, or arylalkyl groups.

Said steroid compounds of said glycosides, that is, glycosylsteroid derivatives of the present invention are dexamethasone, betamethasone, difluprednate, diflorasone, diflucortolone or betamethasone valerate.

Moreover, glycosylsteroid derivatives of the present invention are glycosides of steroid compounds as the aglycone which are substituted at position-21 with simple sugars or acylated simple sugars, wherein hydroxyl groups of said simple sugars or acylated derivatives of simple sugars are protected with toluoyl group.

In addition, glycosylsteroid derivatives of the present invention are glycosides of dexamethasone as the aglycone, wherein position-21 thereof are substituted with simple sugars or acylated sugars selected from a group comprising glucose, galactose, mannose, fucose, rhamnose, N-acetylglucosamine, N-acetylgalactosamine, galacturonic acid, glucuronic acid and sialic acid.

Furthermore, glycosylsteroid derivatives of the present invention are glycosides of betamethasone as the aglycone which are substituted at position-21 thereof with simple sugars or acylated simple sugars selected from a group comprising glucose, galactose, mannose, fucose, N-acetylglucosamine, N-acetylgalactosamine, galacturonic acid, glucuronic acid and sialic acid.

Moreover, hydroxyl groups of simple sugars or acylated simple sugars in said glycosides, that is, steroid derivatives of the present invention are protected with toluoyl group.

In addition, of steroid derivatives related to the present invention, the compounds with the following constitutional formulas are especially useful.

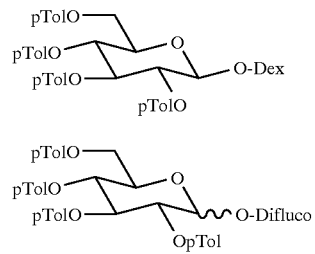

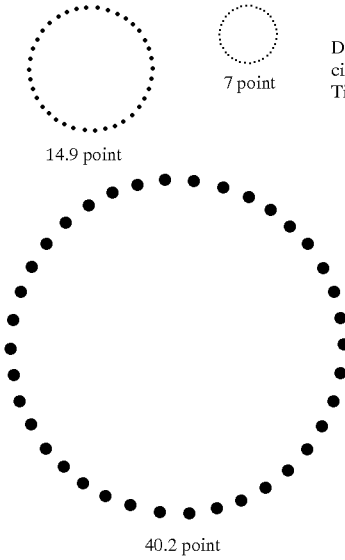

All anti-inflammatory agents comprising said compounds (glycosides) can be used singly or in combination thereof as dermatological ointment, cream, lotion or tape (liniment for external use only). For the treatment of bronchial asthma and allergic rhinitis, they can be used as the intra-oral and intra-nasal inhalation agents, respectively.

Steroid derivatives (glycosides) of the present invention mentioned above not only have the activities for suppressing the granuloma growth and crotone oil-induced ear edema, but also less unfavorable side-effects on weights of body, thymus, spleen or adrenal and on leucocyte counts at the administration or painting of them. Therefore, these agents are less toxic and more highly safe as compared with conventional steroid drugs.

Steroid derivatives of the present invention can be applied for the treatment of eczema, dermatitis (including keratodermia tylodes palmaris progressiva, female facial melanoderma, lichen Vidal, radiodermatitis and dermatitis solaris), pruritus cutaneus, prurigo (including lichen urticatus, strophulus and urticaria perstans), bug bites, psoriasis, palmoplanter pustulosis, lichen planus, lichen nitidus, pityriasis rubra pilaris, pityriasis rosea Gilbert, erythema group (including erythroderma derived from malignant lymphoma), chronic discoid lupus erythematosus, drug rash/toxicoderma, alopecia areata, burn injury (including cicatrix and keloid), frostbite, dermatitis herpetiformis (Duhring) (including psuedosmallpox (permphigoid)), hemorrhoids, and surgical wounds due to tympanoplasty, fenestration operation and tympanomeatomastoidectomy.

The aforementioned protected compounds (glycosides) may be prepared by first protecting the starting material simple sugars or acylated simple sugars with toluoyl or acetyl group, replacing position-1 thereof with a halogen atom, and then reacting the sugar halide with dexamethasone or betamethasone in the presence of molecular sieve and Lewis acids such as silver carbonate, silver triflate or tin (VI) chloride. Said compounds (glycosides) may be obtained by deprotecting these protected glycosides with MeONa/MeOH of the like.

In this case, the use of toluoyl group as the protecting group is advantageous, because said group not only provides the requested product in a better yield by preventing the formation of undesirable ortho ester, but also the toluoyl-protected derivatives themselves have lower undesirable side-effects and higher pharmacological safety.

MOST PREFERRED EMBODIMENT FOR PRACTICING THE PRESENT INVENTION

The most preferred embodiments of the present invention will be described below.
1) Synthesis of compounds Syntheses of derivatives of dexamethasone and betamethasone are described below. Unless otherwise noted, chemicals used of the reagent grade were purchased from Tokyo Kasei Kogyo Co., LTD.

EXAMPLE 1

Figure 1:
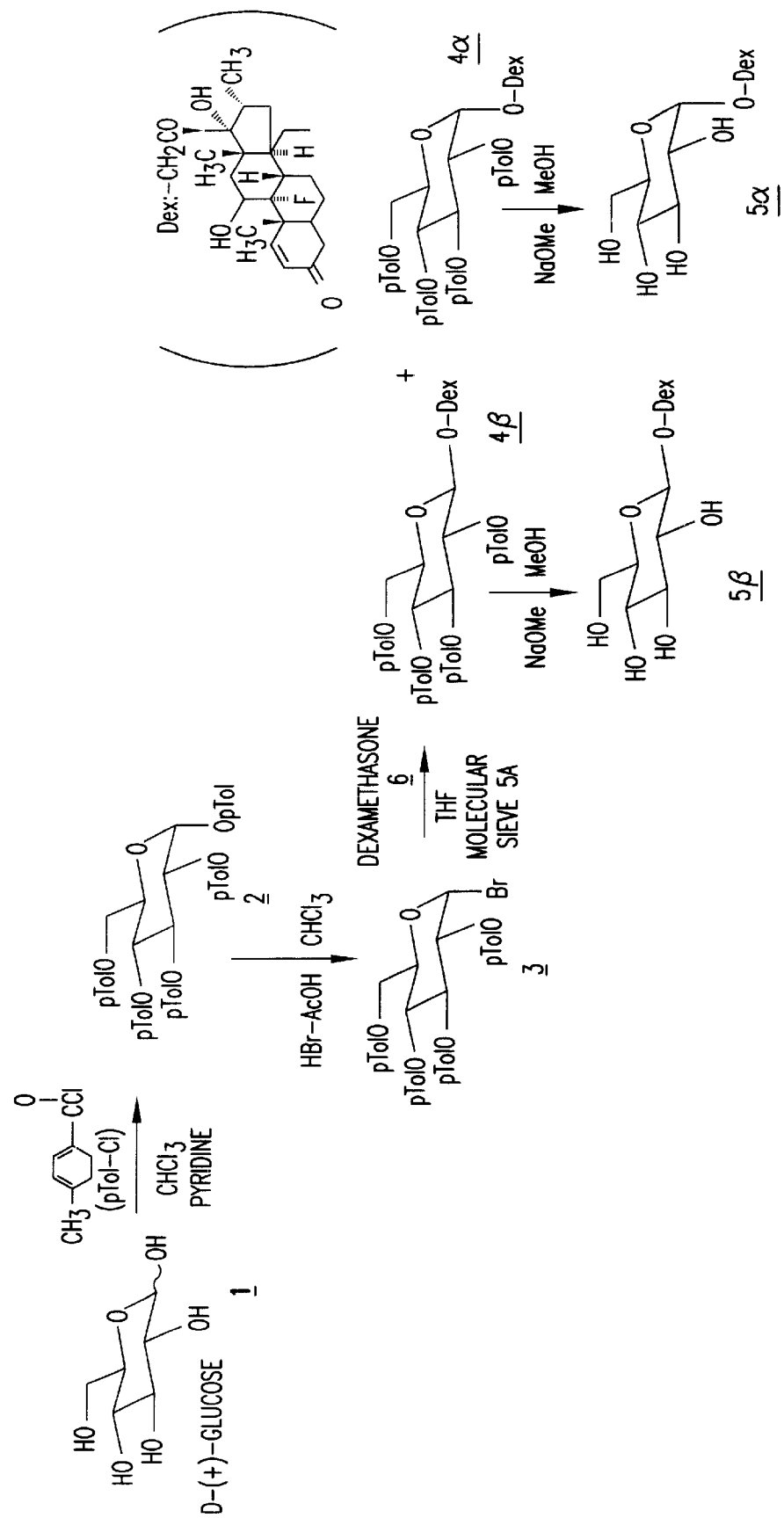
FIG. 1 is a flow-chart showing the synthesis route of glucosyldexamethasone.

Synthesis of glucosyldexamethasone (FIG. 1)
1) Toluoylation of glucose

D-(+)-glucose 1 (2 g) was dissolved in chloroform (40 ml), and to this solution were added p-toluoyl chloride (14.5 ml) and pyridine (8.9 ml) drop-wise at 0–5° C. While the reaction temperature was slowly raised to room temperature, the mixture was stirred for 6 h. The reaction solution was poured into ice-water and extracted with chloroform. The organic layer was washed successively with saturated solutions of copper sulfate, sodium bicarbonate, and sodium chloride. After the chloroform solution was dried over anhydrous magnesium sulfate, the solvent was distilled off in vacuo. A portion (5.33 g) of the residue thus obtained was purified by silica gel column chromatography (toluene:ethyl acetate=50:1) to give 2 (4.5 g) as white powder.

Compound 2

$C_{46}H_{42}O_{11}$ MW=770.831

$^1$H-NMR [500 MHz, CDCl$_3$, Ref=0.000 ppm(TMS)]

(CH$_3$C$_6$H$_4$CO—) X 5: 8.062, 7.910, 7.834, 7.780, 7.775 (each 2H, d, J=8.06) 7.341, 7.207, 7.156, 7.106, 7.101 (each 2H, d, J=8.06)

(CH$_3$C$_6$H$_4$CO—) x 5: 2.474, 2.408, 2.362, 2.315, 2.309 (each 3H, s)

2) Bromination of glucose 2 (4.5 g) was dissolved in chloroform (20 ml), and to this solution was added hydrobromic acid-acetic acid solution (8.8 ml) at 0–5° C. while the reaction temperature was slowly raised to room temperature, the mixture was stirred at room temperature overnight. After the unreacted bromine was removed with an argon stream, the solvent was distilled off in vacuo. The residue was dissolved in chloroform, and washed with cold saturated sodium bicarbonate solution. After the chloroform solution was dried over anhydrous magnesium sulfate, the solvent was distilled off in vacuo to yield 3 as pale yellow powder [2.5 g (yield 59.2%)].

Compound 3
C$_{38}$H$_{35}$O$_9$Br MW=715.593

$^1$H-NMR [500 MHz, CDCl$_3$, Ref=0.000 ppm(TMS)]

(CH$_3$C$_6$H$_4$CO—) x 4: 7.944, 7.881, 7.830, 7.761 (each 2H, d, J=8.06) 7.236, 7.191, 7.160, 7.094 (each 2H, d, J=8.06)

(CH$_3$C$_6$H$_4$CO—) x 4: 2.414, 2.365, 2.357, 2.299 (each 3H, s)

Position-1 of glucose: 6.849 (1H, d, J$_{1,2}$=4.03)

3) Synthesis of glucosyldexamethasone

Dexamethasone (6) (300 mg) was dissolved in tetrahydrofuran (20 ml), and to this solution were added molecular sieve 5A (400 mg) and silver triflate (390 mg). Then, to this mixture was added, under an argon atmosphere and at 0–5° C., a glucose bromide (3) (1.10 g) dissolved in tetrahydrofuran (10 ml). while the reaction temperature was slowly raised to room temperature, the resulting mixture was stirred for 2 h. After the reaction solution was filtered, the solvent of the mother liquor was evaporated in vacuo. The residue thus obtained was dissolved in chloroform, and washed with saturated sodium chloride solution. After the chloroform solution was dried over anhydrous magnesium sulfate, the solvent was distilled off in vacuo. The residue thus obtained was purified by silica gel column chromatography (toluene:ethyl acetate=3:1) to obtain 4 as white powder [441.2 mg (yield 55.7%)].

This product was further purified by HPLC using a reversed phase partition column (acetonitrile-water) to obtain β-anomer (4β) [248.16 mg (yield 32.3%)] and α-anomer (4α) [52.84 mg (yield 6.7%)], respectively, both as white powder.

Compound 4
C$_{60}$H$_{63}$FO$_{14}$ MW=1027.148
β-anomer (4β)

$^1$H-NMR [500 MHz, CDCl$_3$, Ref=0.000 ppm (TMS)]

1: 5.040 (1H, d, J$_{1,2}$=8.06)
2: 5.492 (1H, d, J$_{2,3}$=9.89)
3: 5.884 (1H, t, J$_{3,4}$=10.99)
4: 5.660 (1H, t)
5: 4.064–4.044 (1H, m)
6: 4.643 (2H, t)

(CH$_3$C$_6$H$_4$CO—) x 4: 2.405, 2.363, 2.351, 2.299 (each 3H, s)

(CH$_3$C$_6$H$_4$CO—) x 4: 7.873, 7.831, 7.808, 7.732 (each 2H, d, J=6.9 Hz)

IR $\nu^{KBr}$ cm$^{-1}$ 3508(O—H), 1734(C═O position-20), 1665(C═O position-3)

FAB(+)MS 1027(M+H)$^-$, 1009(M–OH)$^-$

MP: 152–155° C.

α-anomer (4α)

1: 5.302 (1H, d, J$_{1,2}$=3.67)
3: 6.215 (1H, t)
4: 5.727 (1H, t)
5: 4.631–4.605 (1H, m)
6: 4.867 (1H, dd, J$_{6,6'}$=12.46)
6': 4.276 (1H, dd)

(CH$_3$C$_6$H$_4$CO—) x 4: 2.410, 2.367, 2.348, 2.300 (each 3H, s)

(CH$_3$C$_6$H$_4$CO—) x 4: 7.899, 7.864, 7.853, 7.768 (each 2H, d)

IR $\nu^{KBr}$ cm$^{-1}$ 3438(O—H), 1731(C═O position-20), 1666(C═O position-3)

FAB(+)MS 1027(M+H)$^-$, 1009(M–OH)$^-$

MP: 150–153° C.

4) Deprotection of glucosyldexamethasone (β-anomer)

4β (144 mg) was dissolved in methanol (16 ml), and to this solution was added, at 0–5° C., 1 M sodium methoxide (107.6 μl). The resulting mixture was stirred for 5 h at room temperature. The reaction solution was applied to a gel filtration column of LH-20, and eluted with methanol. After the solvent of fractions containing product was distilled off in vacuo, the residue thus obtained was purified by HPLC using a reversed phase partition column (acetonitrile-water) to obtain 5β as white powder [67.8 mg (yield 88.5%)].

Compound 5β
C$_{29}$H$_{39}$FO$_{10}$ MW=554.608

$^1$H-NMR [(500 MHz, d6-DMSO, Ref=2.50 ppm (DMSO)]

1; 4.170 (1H, d, J$_{1,2}$=7.70)
5; 3.438 (1H, dd, J$_{5,6}$=12.09)
6; 3.696 (1H, dd, J$_{6,6'}$=1.83)

FAB(–)MS 553(M–H)$^-$

MP: 238–241° C.

5) Deprotection of glucosyldexamethasone (α-anomer)

4α (35 mg) was dissolved in methanol (10 ml), and to this solution was added 1 M sodium methoxide (62 μl) at 0–5° C. The resulting mixture was stirred for 5 h at room temperature. The reaction mixture was loaded onto a gel filtration column of LH-20, and eluted with methanol. After the solvent of fractions containing product was distilled off in vacuo, the residue thus obtained was purified by HPLC using a reversed phase partition column (acetonitrile-water) to obtain 5α as white powder [7.46 mg (yield 40.0%)].

Compound 5α
C$_{28}$H$_{39}$FO$_{10}$ MW=554.608

IR $\nu^{KBr}$ cm$^{-1}$ 3404(O—H), 1712(C═O position-20), 1661(C═O position-3)

FAB(–)MS 553(M–H)$^-$

MP: 173–176° C.

EXAMPLE 2

Figure 2:
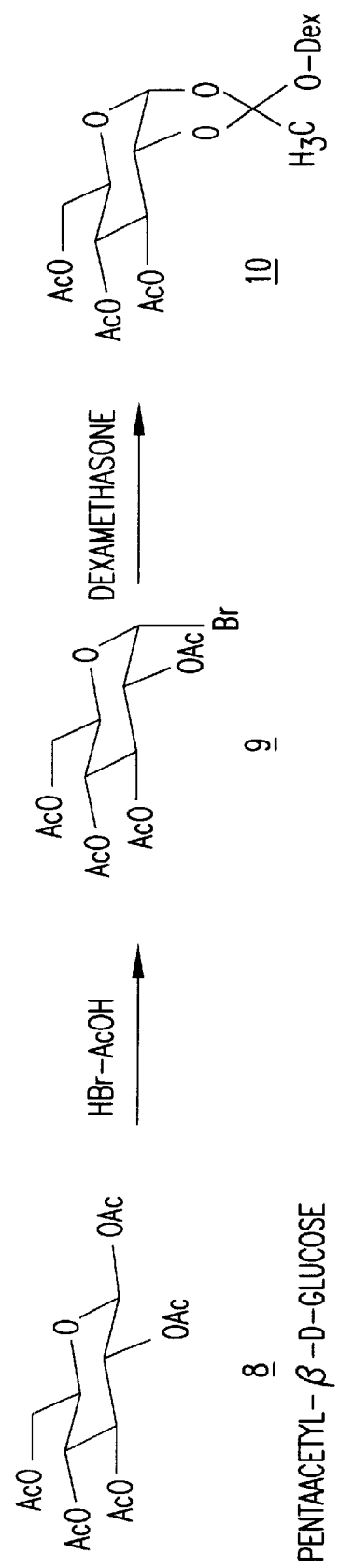
FIG. 2 is a flow-chart showing the synthesis route of glucosyldexamethasone (ortho ester derivative).

Synthesis of glucosyldexamethasone (ortho ester) (FIG. 2)

1) Bromination of glucose (per Ac derivative)
C$_{16}$H$_{22}$O$_{11}$ (8) → C$_{14}$H$_{19}$O$_9$Br (9)
(MW=390.34) (MW=411.20)

To hydrogen bromide-acetic acid solution (80 ml) precooled to 0–5° C. was added pentaacetyl-β-D-glucose (8) (20 g), and the mixture was stirred for 3 h at the same temperature. Then, after the solvent was distilled off in vacuo, the residue was dissolved in chloroform, and the solution was washed with saturated sodium bicarbonate solution. After the chloroform solution was dried over anhydrous magnesium sulfate, the solvent was evaporated in vacuo. The residue thus obtained was recrystallized from ethyl alcohol (60 ml) to obtain 9 as white powder [12.0 g (yield 56.7%)].

$^1$H-NMR [500 MHz, CDCl$_3$, Ref=0.000 ppm(TMS)]

1: 6.612 (1H, d, $J_{1,2}$=4.03)

2: 4.842 (1H, dd, $J_{2,3}$=9.89)

3: 5.562 (1H, t)

4: 5.163 (1H, t)

5: 4.292 (1H, dd, $J_{5,6}$=4.03)

6: 4.332 (1H, dd, $J_{6,6'}$=12.45)

6': 4.122 (1H, dd)

(—OCOCH$_3$) x 4: 2.103, 2.099, 2.082, 2.036 (each 3H, s)

2) Synthesis of glucosyldexamethasone (ortho ester)

$C_{14}H_{19}O_9Br$ (9)+dexamethasone (6)→$C_{36}H_{47}O_{11}F$ (10)
(MW=411.20) (MW=674.8)

Dexamethasone (6) (1.7 g) was dissolved in chloroform (300 ml), and to this solution were added molecular sieve 4A (5 g) and silver carbonate (5.5 g). To this solution was added, under a nitrogen atmosphere, a glucose bromide (9, 5 g) dissolved in chloroform (150 ml), and the mixture was stirred for 4 h. After the reaction solution was filtered, the filtrate was washed with saturated sodium chloride solution. After the chloroform solution was dried over anhydrous magnesium sulfate, the solvent was distilled off in vacuo. The residue thus obtained was purified by silica gel column chromatography first with a solvent system (chloroform:methanol=30:1), and then with another solvent system (toluene:ethyl acetate=2:1) to obtain (10) as white powder [193.8 mg (yield 43.5)].

Compound 10

Rf=0.56 (silica gel TLC, CHCl$_3$:CH$_3$OH=30:1)

$^1$H-NMR [500MHz, CDCl$_3$, Ref=0.000 ppm(TMS)]

1: 5.786 (1H, d, $J_{1,2}$=5.13)

(—OCOCH$_3$) x 4: 2.142, 2.115, 2.111 (12H, s)

EXAMPLE 3

Figure 3:
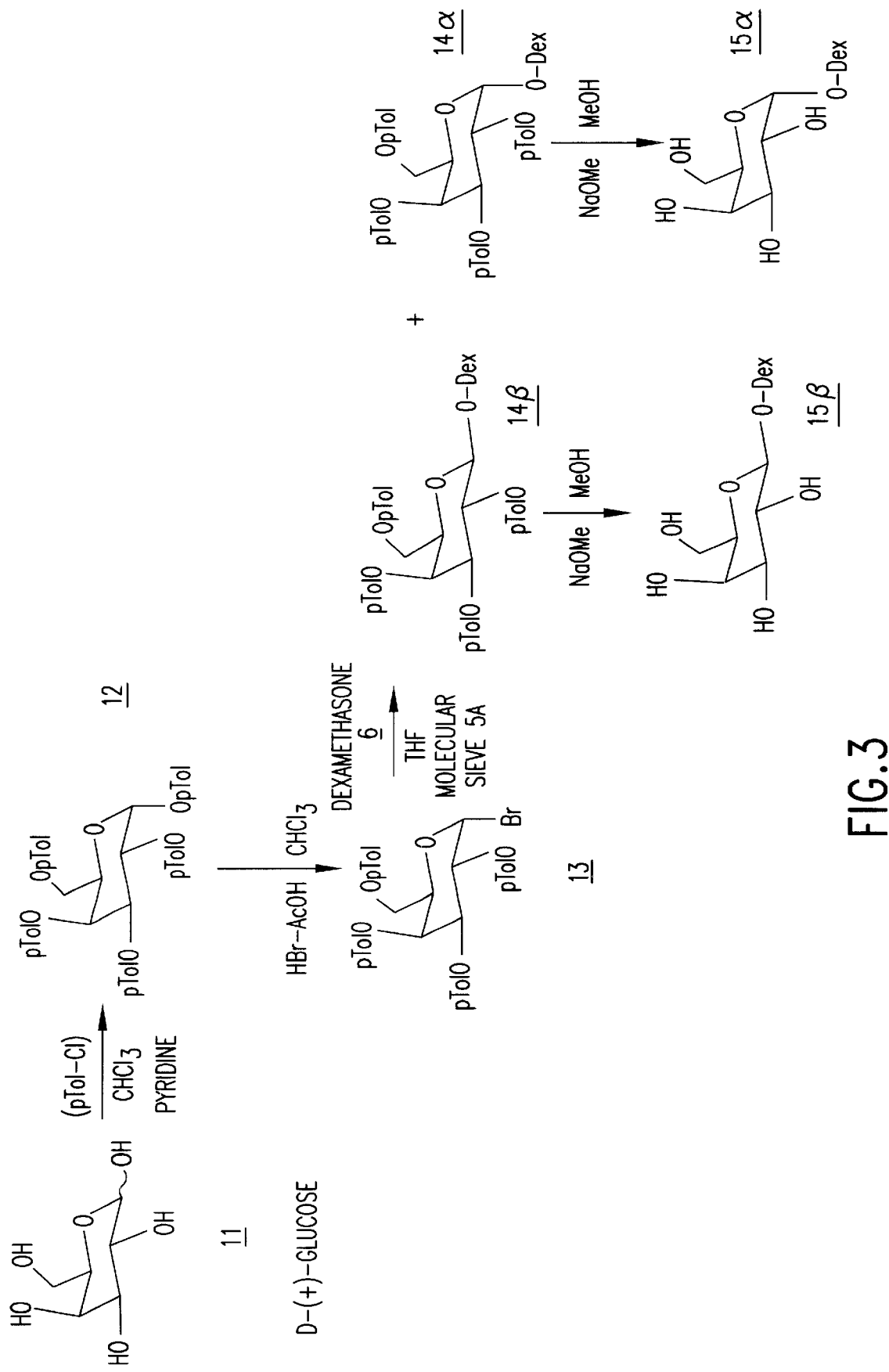
FIG. 3 is a flow-chart showing the synthesis of route of galactosyldexamethasone.

Synthesis of galactosyldexamethasone (FIG. 3)

1) Toluoylation of galactose (11→12)

D-(+)galactose (11) (2 g) was dissolved in chloroform (40 ml), and to this solution were added p-toluoyl chloride (14.5 ml) and pyridine (8.9 ml) drop-wise at 0–5° C. While the reaction temperature was raised slowly to room temperature, the mixture was stirred for 5 h. After the reaction solution was poured into ice-water and extracted with chloroform, the organic layer was washed successively with saturated solutions of copper sulfate, sodium bicarbonate and sodium chloride. After the chloroform solution was dried over anhydrous magnesium sulfate, the solvent was distilled off in vacuo. A portion (5 g) of the residue thus obtained was purified by silica gel column chromatography (toluene:ethyl acetate=40:1) to obtain 12 as white powder [2.4 g (yield 97.4%)].

Compound 12

$C_{46}H_{42}O_{11}$ MW=770.831

$^1$H-NMR [500 MHz, CDCl$_3$, Ref=0.000 ppm(TMS)]

CH$_3$C$_6$H$_4$CO—: 8.000, 7.985, 7.837, 7.740, 7.696 (each 2H, d, J=8.43)

CH$_3$C$_6$H$_4$CO—: 2.452, 2.449, 2.372, 2.305, 2.298 (each 3H, S)

2) Bromination of 12 (12→13)

12 (2.35 g) was dissolved in chloroform (10 ml), and to this solution was added hydrogen bromide-acetic acid solution (4.58 ml) at 0–5° C. while the reaction temperature was slowly raised to room temperature, the mixture was stirred overnight. After removing the unreacted bromine with an argon stream, the solvent was distilled off in vacuo. The residue was taken up into chloroform, and washed with cold saturated sodium bicarbonate solution. After dried over anhydrous magnesium sulfate, the solvent was distilled off in vacuo to obtain 13 as pale yellow powder [1.87 g (yield 83.7%)].

Compound 13

$C_{39}H_{35}O_9Br$ MW=715.593

$^1$H-NMR [500 MHz, CDCl$_3$, Ref=0.00 ppm (TMS)]

1: 6.963 (1H, d, $J_{1,2}$=4.03)

2: 5.614 (1H, dd, $J_{2,3}$=10.63)

3: 6.018 (1H, dd, $J_{3,4}$=3.29)

4: 6.068 (1H, dd)

5: 4.883 (1H, t)

6: 4.598 (1H, dd, $J_{6,6'}$=11.72)

6': 4.424 (1H, dd)

CH$_3$C$_6$H$_4$CO—: 7.946, 7.896, 7.880, 7.676 7.278, 7.213, 7.185, 7.050 (each 2H, d, J=8.06)

CH$_3$C$_6$H$_4$CO—: 2.444, 2.394, 2.360, 2.302 (each 3H, s)

3) Synthesis of galactosyldexamethasone

13+6→14α+14β

Dexamethasone 6 (456mg) was dissolved in tetrahydrofuran (20 ml), and to this solution were added molecular sieve 5A (700 mg) and silver triflate (598 mg). To this solution was added, under an argon atmosphere, a galactose bromide 13 (1.7 g) dissolved in tetrahydrofuran (20 ml), and the mixture was stirred at room temperature for 2–3 h. After the reaction solution was filtered, the solvent was distilled off from the mother liquor in vacuo. The residue was dissolved in ethyl acetate, washed with saturated sodium chloride solution, and dried over anhydrous magnesium sulfate. The solvent was distilled off in vacuo, and the residue thus obtained was first purified by silica gel chromatography (toluene:ethyl acetate=3:1). The product was further purified by HPLC using a reversed phase partition column (acetonitrile-water) to obtain β-anomer (14β) [232.2 mg (yield 31.2%)] and α-anomer (14α) [178.6 mg (yield 24.0%)], both as white powder.

Compound 14

$C_{60}H_{63}FO_{14}$ MW=1027.148

β-anomer (14β)

$^1$H-NMR (500 MHz, CDCl$_3$, Ref=0.00 ppm (TMS))

1: 4.947 (1H, d, $J_{1,2}$=8.06)

2: 5.829 (1H, dd, $J_{2,3}$=10.26)

3: 5.572 (1H, d, $J_{3,4}$=3.30)

4: 5.906 (1H, d)

CH$_3$C$_6$H$_4$CO—: 7.991, 7.879, 7.658, 7.292, 7.240, 7.168, 7.040 (each 2H, d, J=8.06)

CH$_3$C$_6$H$_4$CO—: 2.426, 2.414, 2.346, 2.292 (each 3H, s)

IR $\nu^{KBr}$ cm$^{-1}$ 3496(O—H), 1731(C=O position-20), 1666(C=O position-3)

FAB(+)MS 1027(M+H)$^-$, 1009(M–OH)$^-$

MP: 163–165° C.

α-anomer (14α)

1: 5.438 (1H, d, $J_{1,2}$=3.66)

2: 5.666 (1H, dd, $J_{2,3}$=10.26)

5: 4.548 (1H, dd, $J_{6,6}$=5.13, $J_{6,6'}$=7.69)

6: 4.695 (1H, dd, $J_{6,6\alpha}$=10.99)

6': 4.308 (1H, dd)

CH$_3$C$_6$H$_4$CO—: 8.002, 7.883, 7.835, 7.667, 7.295, 7.192, 7.157, 7.015 (each 2H, d, J=8.06)

CH$_3$C$_6$H$_4$CO—: 2.457, 2.387, 2.341, 2.294 (each 3H, s)

IR $\nu^{KBr}$ cm$^{-1}$ 3460(O—H), 1730(C=O position-20), 1666(C=O position-3)

FAB(+)MS 1027(M+H)$^+$, 1009(M−OH)$^+$

MP: 163–165° C.

4) Deprotection of galactosyldexamethasone (β) (14β→15β)

14β (160 mg) was dissolved in methanol (15 ml), and to this solution was added 1 M sodium methoxide (121 μl) at 0–5° C. The mixture was stirred for 3 h at room temperature. The reaction solution was loaded onto a gel filtration column of LH-20, and eluted with methanol. After the solvent was distilled off from fractions containing product in vacuo, the residue thus obtained was purified by HPLC using a reversed phase partition column (acetonitrile-water) to obtain 15β as white powder [67.9 mg (yield 78.6%)].

Compound 15

$C_{28}H_{39}FO_{10}$ MW=554.608

$^1$H-NMR [(500 MHz, CD$_8$OD, Ref=3.30 ppm (CH$_3$OD)]

1: 4.236 (1H, d, J$_{1,2}$=7.69)

2: 3.593, 3.424 (1H, dd, J$_{2,3}$=9.89)

3: 3.476, 3.456 (1H, dd, J$_{3,4}$=3.30)

4: 3.795 (1H)

5: 3.505, 3.492 (1H, dd, J$_{5,6}$=6.96, J$_{5,6}$=4.76)

6: 3.774, 3.752 (1H, dd, J$_{6,6'}$=11.35)

6': 3.719, 3.697 (1H, dd)

FAB(−)MS 553(M−H)$^-$

MP: 175–178° C.

5) Deprotection of galactosyldexamethasone (α) (14α→15α)

14α (127.05 mg) was dissolved in methanol (10 ml), and to this solution was added 1 M sodium methoxide (96 μl) at 0–5° C. The mixture was stirred at room temperature for 3 h. The reaction mixture was applied to a gel filtration column of LH-20, and eluted with methanol. After the solvent was distilled off from fractions containing product in vacuo, the residue thus obtained was purified by HPLC using a reversed phase partition column (acetonitrile-water) to obtain 15α as white powder [49.19 mg (yield 72.8%)].

Compound 15

$C_{29}H_{39}FO_{10}$ MW=554.608

$^1$H-NMR [(500 MHz, CD$_3$OD, Ref=3.30 ppm (CH$_3$OD)]

1: 3.885 (1H, d, J$_{1,2}$=2.93)

2–6: 3.6–3.8 ppm(6H, m)

IR ν$^{KBr}$ cm$^{-1}$ 3438(O—H), 1715(C=O position-20), 1662(C=O position-3)

FAB(−)MS 553(M+H)$^-$

MP: 225–228° C.

EXAMPLE 4

Figure 4:
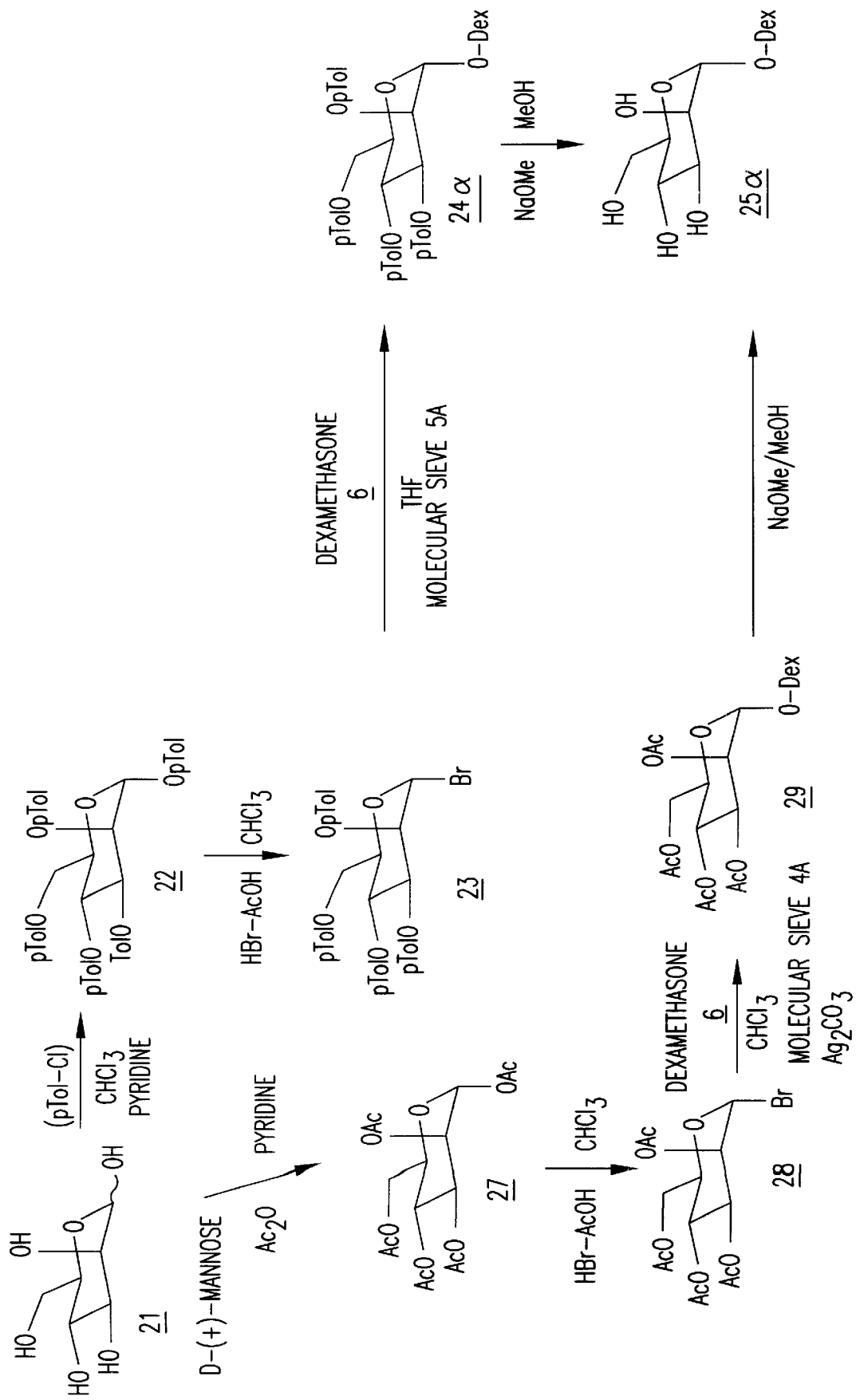
FIG. 4 is a flow-chart showing the synthesis route of mannosyldexamethasone.

Synthesis of mannosyldexamethasone (FIG. 4)

1) Toluoylation of mannose

D-(+)-Mannose 21 (2.3 g) was dissolved in chloroform (40 ml), and to this solution were added p-toluoyl chloride (14.5 ml) and pyridine (8.9 ml) drop-wise at 0–5° C. while the reaction temperature was slowly raised to room temperature, the mixture was stirred for 5 h. The reaction solution was poured into ice-water, and extracted with chloroform. The organic layer was washed successively with saturated solutions of copper sulfate, sodium bicarbonate, and sodium chloride. After the chloroform solution was dried over anhydrous magnesium sulfate, the solvent was distilled off in vacuo. A portion (6 g) of the residue thus obtained was purified by silica gel column chromatography (toluene:ethyl acetate=40:1) to give 22 as white powder [3.18 g (yield 88.7%)].

Compound 22

$C_{46}H_{42}O_{11}$ $^1$H-NMR [500MHz, CDCl$_3$, Ref=0.000 ppm(TMS)]

(CH$_3$C$_6$H$_4$CO—) x 5: 8.078, 7.961, 7.950, 7.834, 7.738, 7.345, 7.195, 7.178, 7.151, 7.077 (each 2H, d, J=8.06)

(CH$_3$C$_6$H$_4$CO—) x 5: 2.476, 2.449, 2.423, 2.350, 2.306 (each 3H, s)

Position-1 of mannose: 6.579 (1H, d, J$_{1,2}$=1.84)

2) Bromination of mannose derivative (22)

22 (3.14 g) was dissolved in chloroform (15 ml), and to this solution was added hydrogen bromide-acetic acid solution (6.12 ml) at 0–5° C. While the reaction temperature was slowly raised to room temperature, the mixture was stirred at room temperature overnight. After the unreacted bromine was removed with an argon stream, the solvent was distilled off in vacuo. The residue was dissolved in chloroform, and washed with cold saturated sodium bicarbonate solution. After the chloroform solution was dried over anhydrous magnesium sulfate, the solvent was distilled off in vacuo to give 23 as light yellow powder [2.61 g (yield 87.6%)].

Compound 23

$C_{39}H_{35}O_9Br$ MW=715.593

$^1$H-NMR [500 MHz, CDCl$_3$, Ref=0.000 ppm(TMS)]

(CH$_3$C$_6$H$_4$CO—) x 4: 7.972, 7.897, 7.858, 7.719 (each 2H, d, J=8.06)

(CH$_3$C$_6$H$_4$CO—) x 4: 2.430, 2.359, 2.294 (12H, s)

3) Synthesis of mannosyldexamethasone

Dexamethasone (6) (600 mg) was dissolved in tetrahydrofuran (20 ml), and to this solution were added molecular sieve 5A (600 mg) and silver triflate (783 mg). To this mixture was added, under an argon atmosphere, a mannose bromide 23 (2.3 g) dissolved in tetrahydrofuran (15 ml), and the reaction mixture was stirred for 4 h until the reaction temperature reached room temperature. The reaction solution was filtered, and the solvent of the mother liquor was distilled off in vacuo. The residue thus obtained was dissolved in ethyl acetate, washed with saturated sodium chloride solution, and then the organic layer was dried over anhydrous magnesium sulfate. After the solvent was distilled off in vacuo, the residue thus obtained was purified by silica gel column chromatography (toluene:ethyl acetate= 3:1) to obtain 647 mg of white powder.

The above product was further purified by HPLC using a reversed phase partition column (acetonitrile-water) to obtain α-anomer (24α) [462.3 mg (yield 29.2%)].

Compound 24α

$C_{60}H_{63}FO_{14}$ MW=1027.148

$^1$H-NMR [500 MHz, CD$_3$Cl$_3$, Ref=0.00 ppm (TMS)]

1: 5.216 (1H, s)

2: 5.954 (1H, dd, J$_{2,3}$=3.29)

3: 6.153 (1H, dd, J$_{3,4}$=10.25)

6': 4.456 (1H, dd, J$_{6,6'}$=12.09)

(CH$_3$C$_6$H$_4$CO—) x 4: 8.183, 8.099, 8.007, 7.935 (each 2H, d, J=8.06)

(CH$_3$C$_6$H$_4$CO—) x 4: 2.646, 2.612, 2.577, 2.508 (each 3H, s)

IR ν$^{KBr}$ cm$^{-1}$ 3498(O—H), 1730(C=O position-20), 1667(C=O position-3)

FAB(+)MS 1027(M+H)$^-$, 1009(M−OH)$^-$

MP: 155–158° C.

4) Deprotection of mannosyldexamethasone (α)

24α (150 mg) was dissolved in methanol (10 ml), and to this solution was added 1 M sodium methoxide (113 μl) at 0–5° C. The mixture was stirred at room temperature for 2 h. The reaction solution was applied to a gel filtration column of LH-20, and eluted with methanol. After evaporation of the solvent from fractions containing product in vacuo, the residue was purified by HPLC using a reversed phase partition column (acetonitrile-water) to obtain 25α as white powder [57.67 mg (yield 72.3%)].

Compound 25α
$C_{29}H_{39}FO_{10}$ MW=554.608
$^1$H-NMR [500 MHz, DMSO, Ref=2.50 ppm (DMSO)]
1: 4.625 (1H, d, $J_{1,2}$=1.83)
2: 3.707 (1H, d, $J_{2,3}$=3.30)
4: 3.403 (1H)
6: 3.647 (1H, dd, $J_{6,6'}$=11.73)
IR $\nu^{KBr}$ cm$^{-1}$ 3438(O—H), 1715(C=O position-20), 1662(C=O position-3)
FAB(-)MS 553(M+H)$^-$
MP: 189–192° C.

5) Acetylation of mannose
$C_6H_{12}O_6$ (21)→$C_{16}H_{22}O_{11}$ (27)
(MW=180.16) (MW=390.34)

D-(+)Mannose 21 (15 g) was suspended in acetic anhydride (180 ml), and to this suspension was added pyridine (46.5 ml) drop-wise at 0–5° C. the mixture was stirred at room temperature for about 5 h. The reaction solution was poured into ice-water, extracted with chloroform, and the organic layer was washed with 5% copper sulfate solution. After the chloroform solution was dried over anhydrous magnesium sulfate, the solvent was evaporated in vacuo to give 27 as pale yellow oily product (36.9 g).

$^1$H-NMR [500 MHz, CDCl$_3$, Ref=0.000 ppm(TMS)]
1: 6.091 (1H, d, $J_{1,2}$=1.83)
6: 4.332 (1H, dd, $J_{6,6'}$=12.46)
6': 4.122 (1H, dd, $J_{5,6'}$=2.57)
(—OCOCH$_3$) x 5: 2.181, 2.171, 2.096, 2.057, 2.011 (each 3H, s)

6) Bromination of mannose
27 28
$C_{16}H_{22}O_{11}$→$C_{14}H_{19}O_9Br$
(MW=390.34) (MW=411.20)

27 (5.8 g) was dissolved in chloroform (11 ml), and to this solution was added a hydrobromide-acetic acid solution (11 ml) at 0–5° C. The mixture was stirred for about 4 h. The reaction solution was washed with saturated sodium bicarbonate solution, dried over anhydrous magnesium sulfate. Evaporation of the solvent in vacuo gave 28 as pale yellow oily product [5.9 g (yield 95.9%)].

$^1$H-NMR [500 MHz, CDCl$_3$, Ref=0.000 ppm(TMS)]
1: 6.298 (1H, d, $J_{1,2}$=1.10)
2: 5.451 (1H, dd, $J_{2,3}$=3.30)
3: 5.720 (1H, dd, $J_{3,4}$=10.26)
4: 5.372 (1H, t)
5: 4.226 (1H, ddd, $J_{5,6}$=4.76)
6: 4.332 (1H, dd, $J_{6,6'}$=12.45)
6': 4.144 (1H, dd, $J_{5,6'}$=2.20)
(—OCOCH$_3$) x 4: 2.178, 2.108, 2.077, 2.012 (each 3H, s)

7) Synthesis of mannosyldexamethasone (per Ac derivative)
$C_{14}H_{19}O_9Br$ (28)+dexamethasone (6)→$C_{36}H_{47}FO_{14}$ (29)
(MW=411.20) (MW=722.76)

Dexamethasone 6 (1.7 g) was dissolved in chloroform (300 ml), and to this solution were added molecular sieve 4A (5 g) and silver carbonate (5.5 g). To this mixture was added, under a nitrogen atmosphere, a mannose bromide 28 (5.8 g) dissolved in chloroform (150 ml), and stirred at room temperature overnight. After the reaction solution was filtered, the mother liquor was washed with saturated sodium chloride solution and dried over anhydrous magnesium sulfate. After the solvent was distilled off in vacuo, the residue thus obtained was purified by silica gel column chromatography first with (chloroform:methanol=30:1) and further purified by the same system with (toluene:ethyl acetate=2:1) to obtain 29 as white powder [453.7 mg (yield 49.6%)].

$^1$H-NMR [500 MHz, CDCl$_3$, Ref=0.000 ppm(TMS)]
1: 5.529 (1H, d, $J_{1,2}$=2.93)
2: 4.860 (1H, dd, $J_{2,3}$=4.40)
3: 5.034 (1H, dd, $J_{3,4}$=9.90)
4: 5.295 (1H, t, $J_{4,5}$=9.52)
5: 3.709 (1H, ddd, $J_{5,6}$=5.47)
6: 4.309 (1H, dd, $J_{6,6'}$32 12.45)
6': 4.122 (1H, dd, $J_{6,6'}$=2.57)
(—OCOCH$_3$) x 4: 2.110, 2.077, 2.072, 1.801 (each 3H, s)
FAB(+)MS 723(M+H)$^+$ 8) Deacetylation of mannosyldexamethasone
$C_{36}H_{47}FO_{14}$ (29)→$C_{28}H_{39}FO_{10}$ (25α)
(MW=722.76) (MW=554.61)

5 (108.24 mg) was dissolved in methanol (25 ml), and to this solution was added 1 M sodium methoxide (1.25 ml) at 0–5° C. The mixture was stirred at room temperature for 6 h. The reaction solution was applied to a gel filtration column of LH-20 and eluted with methanol. The solvent was distilled off from fractions containing product in vacuo to give 25α as white powder [81.4 mg (yield 97.8%)].

EXAMPLE 5

Figure 5:
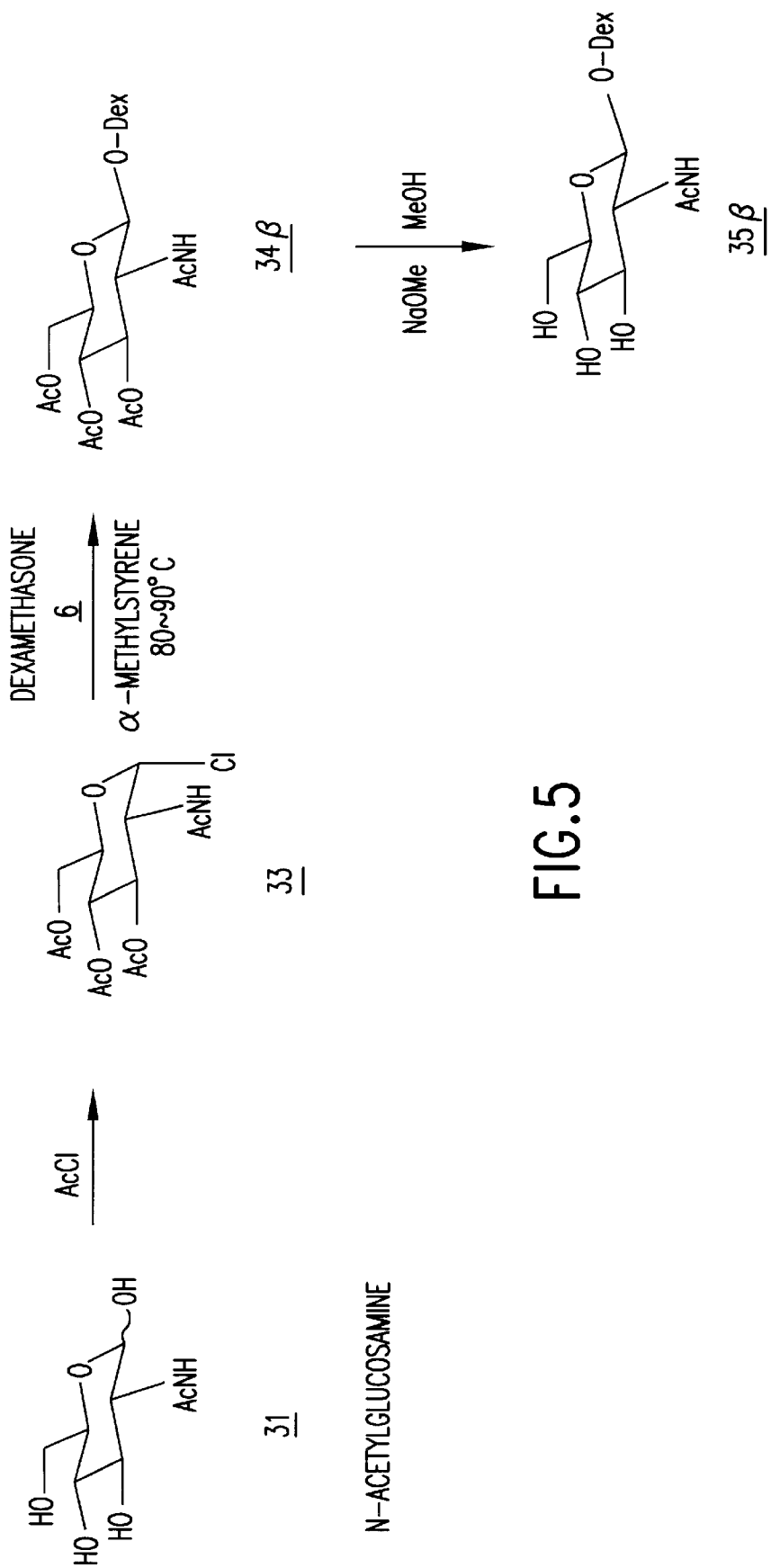
FIG. 5 is a flow-chart showing the synthesis route of β-N-acetylglucosaminyldexamethasone.

Synthesis of β-N-acetylglucosaminyldexamethasone (FIG. 5)

1) Synthesis of N-acetylglucosaminyl chloride (31→33)

N-Acetylglucosamine 31 [10 g (45.2 mmol)] was suspended in acetyl chloride (20 ml), and stirred at room temperature overnight. The reaction solution was diluted with chloroform (100 ml), and poured into ice-water. The chloroform layer was washed with saturated sodium bicarbonate solution, dried over anhydrous magnesium sulfate, and the solvent was distilled off in vacuo. The residue thus obtained was dissolved in diethyl ether (about 10 ml), and allowed to stand at −30° C. overnight. Pale yellow powder (33) which precipitated was collected by filtration [12.7 g(yield 76.8%)].

Compound 33
$C_{14}H_{20}ClNO_9$ MW=365.77
MP: 123–126° C. (decomp.)
FAB(+)MS 364(M−H)$^+$, 366(M+H)$^+$
$^1$H-NMR (500 MHz, CDCl$_3$, Ref=0.000 ppm (TMS)
δ; 1.991, 2.058, 2.060, 2.110 (each 3H, 3 OAc+NHAc) 4.141 (1H, dd, J=1.8, 12.1 Hz, H-6) 4.307 −4.254 (2H, m, H-5,6') 4.538 (1H, ddd, J=3.7, 8.8, 10.6 Hz, H-2) 5.221 (1H, t, J=9.9 Hz, H-4) 5.325 (1H, t, J=10.6 Hz, H-3) 5.811 (1H, d, J=8.8 Hz, N$\underline{H}$Ac) 6.193 (1H, d, J=3.7 Hz, H-1)
IR $\nu^{Kbr}$ cm$^{-1}$: 3245(NH), 1742(O$\underline{C}$OCH$_3$) 1644(NH $\underline{C}$OCH$_3$)

2) Synthesis of a protected derivative of N-acetylglucosaminyldexamethasone

33+dexamethasone(6)→34

An N-acetylglucosamine chloride 33 [2.8 g (7.66 mmol)] and dexamethasone 6 [(1.6 g (2.55 mmol)] were suspended in α-methylstyrene, and the suspension was stirred at 80–90° C. for 5 h. The reaction solution was diluted with chloroform, filtered to remove insoluble materials, and the filtrate was evaporated to dryness in vacuo. The residue thus obtained was purified by silica gel column chromatography, eluted first with (chloroform:methanol=20:1) and then with (toluene:ethyl acetate=1:3) to give 34 as pale yellow powder [114.2 mg (yield 6.2%)]. The powder was dissolved in a small amount of ethyl acetate, and allowed to stand at −30° C. for 3 days. Precipitated crystals were collected by filtration, weighing 81.4 mg (white powder).

Compound 34

$C_{36}H_{48}FNO_{13}$ MW=721.77

MP: 251° C.

FAB(+)MS 704 (M−$H_2$O)$^+$, 722 (M+H)$^+$, 744 (M+Na)$^−$

IR $\nu^{KBr}$ cm$^{-1}$: 3350(OH), 1750(O$\underline{C}$O$\underline{C}$H$_3$) 1730, 1662 (C=O), 1620, 1603(C=C)

$^1$H-NMR (500 MHz, CDCl$_3$, Ref=0.000 ppm(TMS))

δ; 0.883 (3H, d, J=7.3 Hz, 16—CH$_3$) 0.964 (3H, s, CH$_2$) 1.560 (3H, s, CH$_3$) 1.949, 2.041, 2.043, 2.106 (3H, 4 s, 2 OAc+NHAc) 3.713 (1H, ddd, J=2.9, 4.8, 9.5 Hz, H-5$_{GlcNAc}$) 3.818 (1H, dd, J=8.4, 10.3 Hz, H-2$_{GlcNAc}$) 4.160 (1H, dd, J=2.9, 12.1 Hz, H-6$_{GlcNAc}$) 4.329 (1H, dd, J=4.8, 12.1 Hz, H'-6$_{GlcNAc}$) 4.480 (1H, d, J=18.0 Hz, H-21) 4.735 (1H, d, J=18.0 Hz, H'-21) 4.840 (1H, d, J=8.4 Hz, H-1$_{GlcNAc}$) 5.046 (1H, t, J=9.5 Hz, H-4$_{GlcNAc}$) 5.304 (1H, dd, J=9.5, 10.3 Hz, H-3$_{GlcNAc}$) 6.116 (1H, s, H-4) 6.340 (1H, dd, J=1.8, 9.9 Hz, H-1) 7.283 (1H, d, J=9.9 Hz, H-2)

3) Synthesis of a deprotected derivative of N-acetylglucosaminyldexamethasone

34→35β

A protected derivative of N-acetylglucosaminyldexamethasone 34 [56.0 mg (77.6 μmol)] was suspended in methanol (1 ml), and to this suspension was added 1M sodium methoxide (16 μl) at room temperature. The mixture was stirred at room temperature for 50 min. The reaction solution which turned yellow was applied to a gel filtration column of LH-20, and eluted with methanol. Evaporation of the solvent was distilled off from fractions containing product in vacuo to give 35β as white powder [46.6 mg (yield 100%)].

Compound 35β

$C_{30}H_{42}FNO_{10}$ MW=595.66

MP: 208–211° C. (decomp.)

FAB(+)MS 596 (M+H)$^−$, 618 (M+Na)$^−$

IR $\nu^{KBr}$ cm$^{-1}$: 3420(OH), 1718, 1660(C=O), 1620 (C=C)

$^1$H-NMR [500 MHz, CD$_3$CN, Ref=1.950 ppm(CH$_3$CN)]

δ; 0.832 (3H, d, J=7.3 Hz, 16—CH$_3$) 0.949 (3H, s, CH$_3$) 1.530 (3H, s, CH$_3$) 3.214–3.270 (2H, m, H-4$_{GlcNAc}$+H-5$_{GlcNAc}$) 3.400 (1H, dd, J=8.1, 9.9 Hz, H-3$_{GlcNAc}$) 3.548 (1H, dd, J=8.4, 9.9 Hz, H-2$_{GlcNac}$) 3.596 (1H, dd, J=6.2, 12.2 Hz, H-6$_{GlcNAc}$) 3.816 (1H, dd, J=1.5, 12.2 Hz, H'-6$_{GlcNAc}$) 4.383 (1H, d, J=8.4 Hz, H-1$_{GlcNAc}$) 6.029 (1H, s, H-4) 6.239 (1H, dd, J=1.8, 10.3 Hz, H-1) 7.284 (1H, d, J=10.3 Hz, H-2)

EXAMPLE 6

Figure 6:
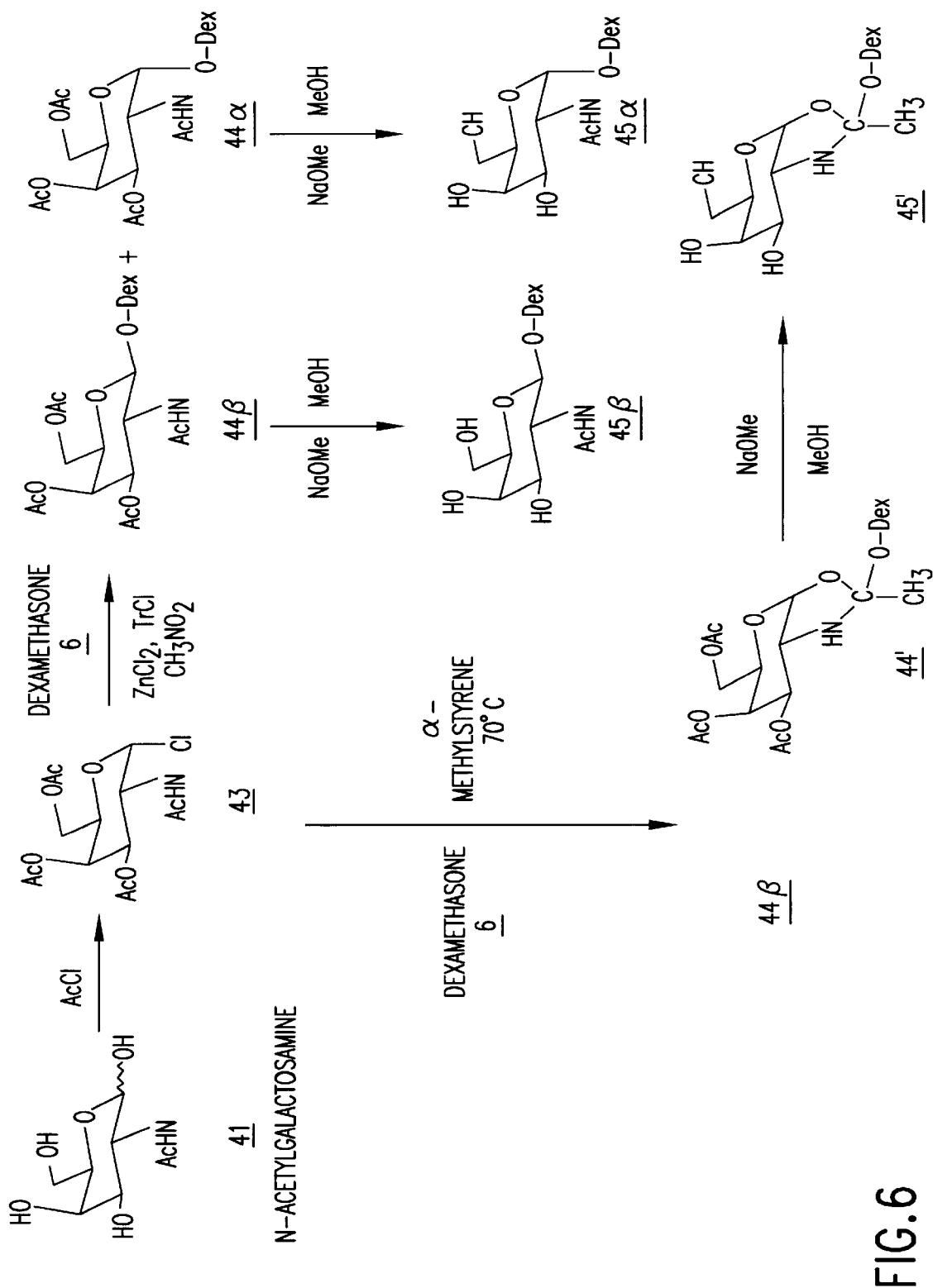
FIG. 6 is a flow-chart showing the synthesis route of N-acetylgalactosaminyldexamethasone.

Synthesis of N-acetylgalactosaminyldexamethasone (FIG. 6)

1) Synthesis of a protected derivative of N-acetylgalactosaminyldexamethasone

41→43

43÷6→44α÷44β

N-Acetylgalactosamine 41 [3.0 g (13.56 mmol)] was suspended in acetyl chloride (6 ml), and stirred at room temperature overnight. The reaction mixture was diluted with chloroform (24 ml), poured into ice-water, and the chloroform layer was washed with saturated sodium bicarbonate. The organic layer dried over anhydrous magnesium sulfate, and the solvent was evaporated in vacuo to give an N-acetylgalactosamine chloride 43 (4.35 g). To a mixture of dexamethasone 6 [5.95 g (15.17 mmol)], the N-acetylgalactosamine chloride 43 [5.55 g (15.17 m mol)], trityl chloride [4.23 g (15.17 mmol)] and zinc chloride [2.07 g (15.17 mmol)] was added nitromethane (130 ml), and the resulting mixture was stirred under an argon atmosphere at room temperature overnight. The reaction solution was diluted with chloroform, and filtered to remove insoluble materials. The filtrate was washed successively with saturated solutions of sodium bicarbonate and sodium chloride. After drying the organic layer over anhydrous magnesium sulfate, the solvent was distilled off in vacuo, and the residue thus obtained was purified by silica gel column chromatography (acetone:toluene =2:3) to give fractions containing the desired product (950.8 mg). This fraction was further purified by HPLC using a reversed phase partition column (acetonitrile-water) to give α-anomer 44α [98.0 mg (yield 0.9%)] and β-anomer 44β [569.5 mg (yield 5.2%)], respectively, both as white powder.

Compound 44α

$C_{36}H_{48}FNO_{14}$ MW=721.77

MP: 165–167° C.

FAB(÷) MS; 722(M+H)$^+$

IR $\nu_{max}^{KBr}$ cm$^{-1}$: 3440(O—H), 1755(COCH$_3$), 1669 (C=O), 1620(C=C)

$^1$H-NMR [500 MHz, CDCl$_3$, Ref=0.000 ppm(TMS)]

δ; 0.917(3H, d, J$_{16CH3,16}$=7.3, 16—CH$_3$) 1.014(3H, s, H-18) 1.565(3H, s, H-19) 1.997, 2.008, 2.092, 2.196(3H×4, each s, COCH$_3$×4) 3.918(1H, dd, J$_{6',6}$=11.0, J$_{6',5}$=8.8, H-6'$_{GalNAc}$) 4.066(1H, dd, J$_{5,6}$=5.1, H-5$_{GalNAc}$) 4.350(1H, dd, H-6$_{GalNAc}$) 4.498(1H, d, J$_{gem}$=18.7, H-21') 4.547(1H, d, H-21) 4.623(1H, ddd, J$_{2,1}$=3.7, J$_{2,NH}$=9.9, J$_{2,3}$=11.4, H-2$_{GalNAc}$) 4.849(1H, d, H-1$_{GalNAc}$) 5.256(1H, dd, J$_{3,4}$=2.9, H-3$_{GalNAc}$) 5.383(1H, d, H-4$_{GalNAc}$) 6.113(1H, d, J$_{4,1}$=2.2, H-4) 6.325(1H, dd, J$_{1,2}$=9.9, H-1) 6.480(1H, d, N$\underline{H}$Ac) 7.235(1H, d, H-2)

Compound 44β

$C_{36}H_{48}FNO_{14}$ MW=721.77

MP: 174–177° C. (decomp.)

FAB(+)MS; 722(M+H)$^−$, 744(M+Na)$^−$

IR $\nu_{max}^{KBr}$ cm$^{-1}$: 3450(O—H), 1750(COCH$_3$), 1660 (C=O position-3), 1622 and 1604(C=C)

$^1$H-NMR [500 MHz, CDCl$_3$, Ref=0.000 ppm(TMS)]

δ; 0.903(3H, d, J$_{16CH3,16}$=7.3, 16—CH$_3$) 0.993(3H, s, H-18) 1.564(3H, s, H-19) 2.000, 2.012, 2,090, 2.186 (3H×4, each s, COCH$_3$×4) 3.850(1H, dd, J$_{5,6}$=5.9, J$_{5,6'}$=7.0, H-5$_{GalNAc}$) 3.978(1H, dd, J$_{6',6}$=11.0, H-6'$_{GalNAc}$) 4.108(1H, ddd, J$_{2,L}$=8.4, J$_{2,NH}$=8.8, J$_{2,3}$=11.0, H-2$_{GalNAc}$) 4.383(1H, dd, H-6$_{GalNAc}$) 4.630(1H, d, J$_{gem}$=18.3, H-21') 4.677(1H, d, H-1$_{GalNAc}$) 4.682(1H, d, H-21) 5.174(1H, dd, J$_{3,4}$=3.3, H-3$_{GalNAc}$) 5.338(1H, d, H-4$_{GalNAc}$) 6.070(12H, d, N$\underline{H}$Ac) 6.112(1H, d, J$_{4,1}$=1.8, H-4) 6.328(1H, dd, J$_{1,2}$=9.9, H-1) 7.235(1H, d, H-2)

2) Synthesis of a deprotected derivative of N-acetylgalactosaminyldexamethasone (α)

44α→45α

A protected derivative of N-acetylgalactosaminyldexamethasone (α-anomer) 44α [70.0 mg (0.097 mmol)] was dissolved in methanol (3 ml), and to this solution was added 1M CH$_3$ONa/MeOH (0.1 ml). The mixture was stirred at room temperature for 3 h. The reaction solution was applied to a gel filtration column of LH-20, eluted with methanol, and the solvent of fractions containing product was evaporated in vacuo to give 45α as white powder [54.9 mg (yield 95.0%)].

Compound 45α
 $C_{30}H_{42}FNO_{10}$ MW=595.66
 MP: 189–191° C.
 FAB(+MS; 596(M+H)⁻, 618(M+Na)⁻
 IR $\nu_{max}^{KBr}$cm⁻¹: 3426(O—H), 1715(C=O 20-position), 1665(C=O 3-position), 1620 and 1605(C=C)
 ¹H-NMR [500 HMz, CD₃OD, Ref–0.000 ppm(TMS)]
 δ; 0.864(3H, d, $J_{16ch3,16}$=7.3, 16—CH₃) 1.008(3H, s, H-18) 1.583(3H, s, H-19) 2.018(3H, s, COCH₃) 3.692–3.721 (1H, m, H-6'$_{GalNAc}$) 3.748–3.778 (2H, m, H-5$_{GalNAc}$, H-6$_{GalNAc}$) 3.819(1H, dd, $J_{3,2}$=11.0, $J_{3,4}$=2.9, H-3$_{GalNAc}$) 3.888(1H, d, H-4$_{GalNAc}$) 4.316(1H, dd, $J_{2,1}$=3.7, H-2$_{GalNAc}$) 4.527(1H, d, $J_{gem}$=18.7, H-21') 4.580(1H, d, H-21) 4.801(1H, d, H-1$_{GalNAc}$) 6.076(1H, d, $J_{4,1}$=1.8, H-4) 6.283(1H, dd, $J_{1,2}$=10.3, H-1) 7.395(1H, d, H-2)

3) Synthesis of a deprotected derivative of N-acetylgalactosaminyldexamethasone (β)

44β→45β

A protected derivative of N-aceylgalactosaminyldexamethasone (β) 44β[84.5 mg (0.117 mmol)] was dissolved in methanol (0.5 ml), and to this solution was added 1M CH₃ONa/MeOH (24 μl), and the mixture was stirred at room temperature for 3 h. The reaction solution was applied to a gel filtration column, eluted with methanol, and the solvent of fractions containing product was evaporated in vacuo to give 45β [63.9 mg (yield 91.7%)] as white powder.
Compound 45β
 $C_{30}H_{42}FNO_{10}$ MW=595.66
 MP: 201–203° C.
 FAB(÷)MS; 596(M+H)⁻, 618(M+Na)⁻
 IR $\nu_{max}^{KBr}$ cm⁻¹: 3420(O—H), 1720(C=O position-20), 1660(C=O position-3), 1620 and 1602(C=C)
 ¹H-NMR [500 HMz, CD₃OD, Ref=3.300 ppm(CH₃OD)]
 δ; 0.845(3H, d, $J_{16CH3,16}$=7.3, 16—CH₃) 0.986(3H, s, H-18) 1.575(3H, s, H-19) 2.018(3H, s, COCH₃) 3.472(1H, dd, $J_{5,6}$=7.3, $J_{5,6'}$=4.8, H-5$_{GalNAc}$) 3.636(1H, dd, $J_{3,2}$=10.6, $J_{3,4}$=2.9, H-3$_{GalNAc}$) 3.726(1H, dd, $J_{6'6}$=11.4, H-6'$_{GalNAc}$) 3.797(1H, d, H-4$_{GalNAc}$) 3.806(1H, dd, H-6$_{GalNAc}$) 3.912(1H, dd, $J_{2,1}$=8.4, H-2$_{GalNAc}$) 4.441(1H, d, H-1$_{GalNAc}$) 4.593(1H, d, $J_{gem}$=18.3, H-21') 4.702(1H, d, H-21) 6.069(1H, d, $J_{4,1}$=1.8, H-4) 6.277(1H, dd, $J_{1,2}$=10.3, H-1) 7.396(1H, d, H-2)

4) N-Acetylgalactosaminyldexamethasone (modified method)

43+6→44β÷44'

An N-acetylgalactosamine chloride (43) (2.8 g) and dexamethasone (6) [1.00 g (2.55 mmol)] were suspended in α-methylstyrene, and stirred at 70° C. for 4.5 h. The reaction solution was diluted with chloroform, filtered to remove insoluble materials, and the solvent of the filtrate was evaporated in vacuo. The residue thus obtained was purified by silica gel column chromatography (chloroform:methanol=20:1) to give fractions containing β-anomer (281.0 mg) and those containing oxazoline derivative (365.3 mg), respectively. The β-anomer containing fraction was further purified by silica gel column chromatography (ethyl acetate) to obtain pale yellow powder 44β [157.7 mg (yield 8.6%)], which was recrystallized from ethyl acetate (1 ml) to yield white powder (153.8 mg). The oxazoline derivative containing fraction was similarly purified by silica gel chromatography (ethyl acetate) to give an oxazoline derivative (44') as white powder [184.8 mg (yield 10.0%)].

Compound 44' (oxazoline derivative)
 $C_{36}H_{48}FNO_{14}$ MW=721.77
 MP: 213–215° C. (decomp.)
 FAB(÷)MS; 722(M+H)⁻, 744 (M+Na)⁻
 IR $\nu_{max}^{KBr}$ cm⁻¹: 3400(O—H), 1750(COCH₃), 1722 (C=O position-20), 1660(C=O position-3), 1618 and 1602 (C=C)
 ¹H-NMR [500 MHz, CDCl₃, Ref=0.000 ppm(TMS)]
 δ; 0.917(3H, d, $J_{16CH3,16}$=7.0, 16—CH₃) 1.080(3H, s, H-18) 1.562(3H, s, H-19) 2.019, 2.089, 2.123, 2.149 (3H×4, each s, COCH₃×4) 4.225(1H, dd, $J_{6',6}$=11.4, $J_{6',5}$=6.6, H-6'$_{GalNAc}$) 4.250(1H, dd, $J_{6',5}$=4.4, H-6$_{GalNAc}$) 4.312(1H, ddd, $J_{2,1}$=1.1, $J_{2,NH}$=6.6, $J_{2,3}$=3.7, H-2$_{GalNAc}$) 4.418(1H, dd, $J_{4,3}$=6.2, $J_{4,5}$=3.7, H-4$_{GalNAc}$) 4.427(1H, d, $J_{gem}$=17.2, H-21') 4.515(1H, d, H-21) 4.787(1H, dd, H-3$_{GalNAc}$) 5.064 (1H, d, H-1$_{GalNAc}$) 5.424–5.454 (1H, m, H-5$_{GalNAc}$) 6.111 (1H, d, $J_{4,1}$=1.8, H-4) 6.159(1H, d, NHAc) 6.333(1H, dd, $J_{1,2}$=10.3, H-1) 7.261(1H, d, H-2)

5) Synthesis of a deprotected oxazoline derivative of N-acetylgalactosaminyldexamethasone

44'→45'

A protected oxazoline derivative of N-acetylgalactosaminyldexamethasone (44') [89.0 mg (0.123 mmol)] was dissolved in methanol (1 ml), and to this solution was added 1M CH₃ONa/MeOH (25 μl). The resulting mixture was stirred at room temperature for 2 h. The reaction solution was applied to a gel filtration column of LH-20, and eluted with methanol. The solvent of fractions containing product were evaporated in vacuo to give 45' as white powder [67.9 mg (yield 92.7%)].
Compound 45' (oxazoline derivative)
 $C_{30}H_{42}FNO_{10}$ MW=595.66
 MP: 169–172° C.
 FAB(÷)MS; 596(M+H)⁻, 618(M+Na)⁻
 IR $\nu_{max}^{KBr}$ cm⁻¹: 3400(O—H), 1718(C=O position-20), 1660(C=O position-3), 1620 and 1602(C=C)
 ¹H -NMR [500 MHz, CD₃OD, Ref=3.300 ppm(CH₃OD)]
 δ; 0.853(3H, d, $J_{16CH3,16}$=7.3, 16—CH₃) 1.006(3H, s, H-18) 1.579(3H, s, H-19) 1.960(3H, s, COCH₃) 3.601(2H, d, $J_{6,5}$=6.6, H-6$_{GalNAc}$) 3.745(1H, dd, $J_{5,4}$=2.6, H-5$_{GalNAc}$) 4.027(1H, d, $J_{4,3}$=5.9, H-4$_{GalNAc}$) 4.058(1H, dd, $J_{3,2}$=3.7, H-3$_{GalNAc}$) 4.228(1H, d, H-2$_{GalNAc}$) 4.383(1H, d, $J_{gem}$=18.3, H-21') 4.693(1H, d, H-21) 4.950(1H, s, H-1$_{GalNAc}$) 6.070 (1H, d, $J_{4,1}$=1.8, H-4) 6.278(1H, dd, $J_{1,2}$=9.9, H-1) 7.400 (1H, d, H-2)

EXAMPLE 7

Figure 7:
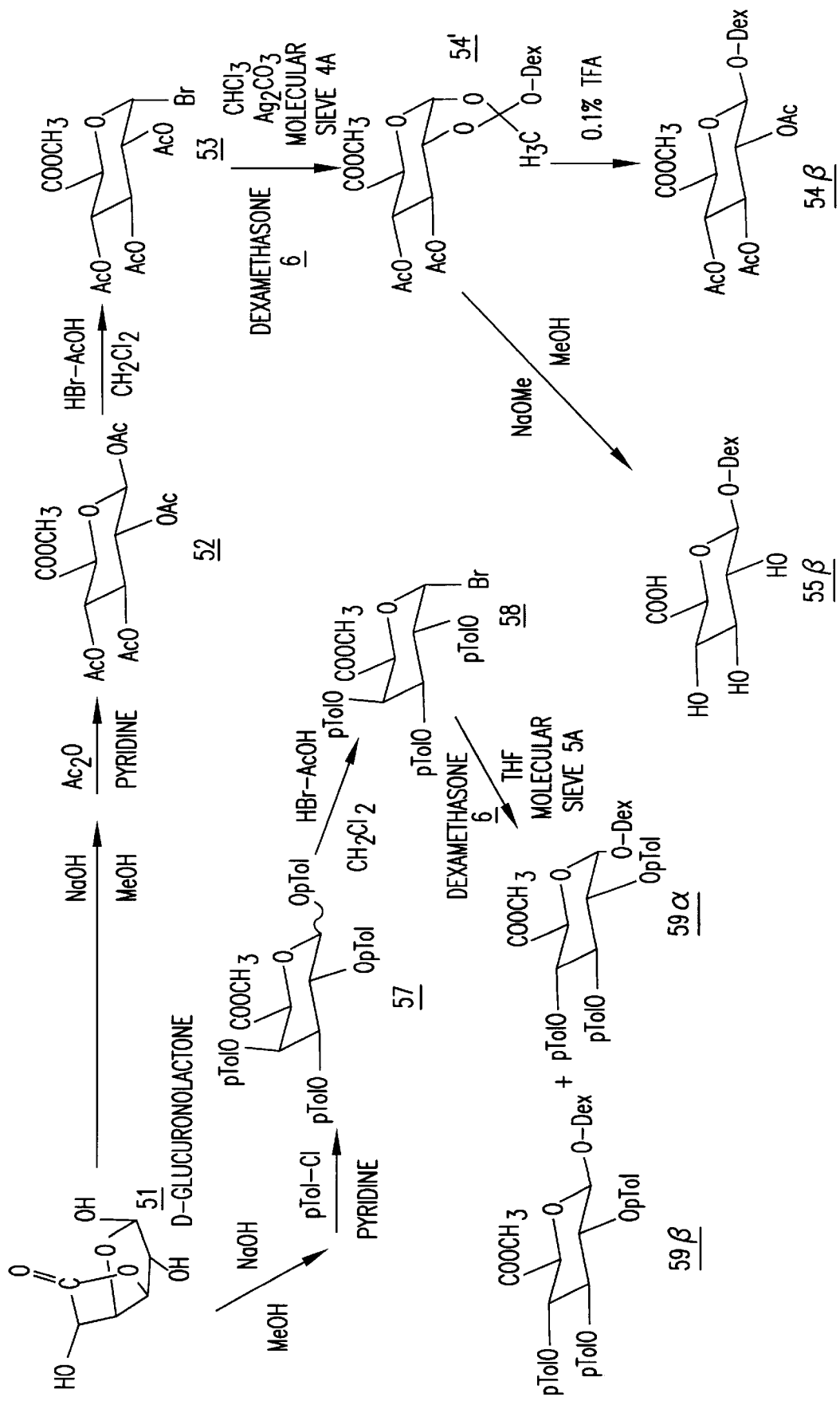
FIG. 7 is a flow-chart showing the synthesis route of β-glucuronyldexamethasone and Tol-protected derivative of β-glucuronyldexamethasone.

Synthesis of β-glucuronyldexamethasone and toluoyl-protected derivative of β-glucuronyldexamethasone (FIG. 7)

1. Synthesis of β-glucuronyldexamethasone

1) D-Glucuronolactone 51 (6.30 g) was suspended in methanol (100 ml), and to this suspension was added sodium hydroxide (12.6 mg). The compounds were completely solubilized by ultrasonication. After the solvent was distilled off from the mixture in vacuo, pyridine (6.0 ml) and acetic anhydride (12.0 ml) were added to the residue under ice-cooling. While the reaction temperature was slowly raised to room temperature, the resulting mixture was continuously stirred for 12 h. Under ice-cooling, methanol was added to the reaction mixture to precipitate 52 as white powder, which was collected by filtration [5.69 g (yield 42.3%)].

51 52

$C_6H_8O_5$=176.13→$C_{15}H_{20}O_{11}$=376.14
Compound 52
 MW: $C_{15}H_{20}O_{11}$=376.14

MP: 182–183° C.
FD-MS: m/z=376 (M)⁻
IR ν$^{KBr}$ cm$^{-1}$: 1763(C=O), 1374(CH$_3$), 1231, 1208(C—C(=O)—O)
$^1$H-NMR (ppm, 500 MHz, CDCl$_3$, Ref=0.000 ppm (TMS))

1  5.770 (1H, d, J$_{1,2}$=7.70 Hz)
2  5.146 (1H, dd, J$_{2,1}$=7.70, J$_{2,3}$=9.16)
3  5.311 (1H, t, J$_{3,2}$=J$_{3,4}$=9.16)
4  5.250 (1H, t, J$_{4,3}$=9.16, J$_{4,5}$=9.52)
5  4.181 (1H, d, J$_{5,4}$=9.52)
—COOCH$_3$ 3.747 (3H, s)
—COCH$_3$ 2.118, 2.031 (3H, s)×2
—COCH$_3$ 2.039 (6H, s)

2) 52 (2.26 g) was dissolved in dichloromethane (20 ml) was added, and to this solution, under ice-cooling, a hydrobromide-acetic acid solution (10.0 ml). The mixture was stirred at room temperature for 12 h. After the reaction solution was washed with saturated sodium bicarbonate solution, the organic layer was dried over anhydrous magnesium sulfate, and the solvent was evaporated in vacuo. The residue thus obtained was purified by silica gel column chromatography (toluene:ethyl acetate=4:1) to give 53 as white powder [1.57 g (yield 65.8%)].

52→53

Compound 53
MS: C$_{13}$H$_{17}$O$_9$Br=397.17
MP: 111–113° C.
FAB(+)MS: m/z=397, 399 (M+H)⁻,
IR ν$^{KBr}$ cm$^{-1}$ : 1767, 1750(C=O), 1379(CH$_3$), 1252, 1229, 1215(C—C(=O)—O)
$^1$H-NMR (ppm, 500 MHz, CDCl$_3$, Ref=0.000 ppm (TMS))

1  6.643 (1H, d, J$_{2,2}$=4.03 Hz)
2  4.859 (1H, dd, J$_{2,1}$=4.03, J$_{2,3}$=9.89)
3  5.616 (1H, t, J$_{3,2}$=9.89, J$_{3,4}$=9.52)
4  5.246 (1H, dd, J$_{4,3}$=9.52, J$_{4,5}$=10.62)
5  4.584 (1H, d, J$_{5,4}$=10.62)
—COOCH$_3$ 3.766 (3H, s)
—COCH$_3$ 2.100, 2.056, 2.052 (3H, s)×3

3) Dexamethasone 6 (1.54 g) was suspended in chloroform (150 ml), and to this solution were added, under an argon atmosphere, molecular shieve 4A (1.50 g) and silver carbonate (1.60 g) and 53 (1.53 g). The resulting mixture was stirred at room temperature for 4 days. After the reaction solution was filtered, the solvent of the filtrate was evaporated in vacuo to give crude 54'(2.80 g). Purification of the crude 54' (580 mg) by silica gel column chromatography (toluene:ethyl acetate=2:1→1:1) gave 54' was white powder [220.6 mg (yield 38.0%)].

53+6→54'

Compound 54'
MW: C$_{35}$H$_{45}$O$_{14}$F=708.73
MP: 133–135° C.
FAB(+)MS: m/z=709 (M+H)⁻, 731 (M+Na)⁻
IR ν$^{KBr}$ cm$^{-1}$ : 3396(O—H), 2944 (C—H), 1757, 1665 (C=O), 1222(C—C(=O)—O)
$^1$H-NMR (ppm, 500 MHz, CDCl$_3$, Ref=0.000 ppm (TMS))

1  5.863 (1H, d, J$_{1,2}$=5.13 Hz)
2  4.253 (1H, dd, J$_{2,1}$=5.13, J$_{2,3}$=2.57)
3  5.154 (1H, dd, J$_{3,2}$=J$_{3,4}$=2.57)
4  5.191 (1H, dd, J$_{4,3}$=2.57, J$_{4,5}$=8.42)
5  4.256 (1H, d, J$_{5,4}$=8.42)
—COOCH$_3$ 3.788 (3H, s)
—COCH$_3$ 2.129, 2.121 (3H, s)×2
CH$_3$ (ortho ester) 1.754 (3H, s)

4) 54' (441.4 mg) was dissolved in acetonitrile/water mixture [140 ml(4/96, containing 0.1% TFA)], and this solution was applied in 20 ml portions to a HPLC column [μ-Bondasphere C$_{18}$-100 Å, flow-rate 23.0 ml/min, detection wave length 254 nm (UV), eluent A/B=water/95% acetonitrile (both containing 0.1% TFA)=94/6→80/20→38/62], and eluted with the gradient for 30 min). Fractions containing product were evaporated in vacuo, and then lyophilized to give 54β as white powder [41.4 mg (yield 9.40)].

54'→54β

Compound 54β
MW: C$_{35}$H$_{45}$O$_{14}$F=708.73
MP: 140–142° C.
FAB(+)MS: m/z=709 (M+H)⁻, 731 (M+Na)⁻
IR ν$^{KBr}$ cm$^{-1}$: 3414(O—O), 2946 (C—H), 1759, 1664 (C=O), 1222(C—C(=O)—O)
$^1$H-NMR (ppm, 500 HMz, CDCl$_3$, Ref=0.000 ppm (TMS))

1  4.844 (1H, d, J$_{1,2}$=7.70 Hz)
2  5.066 (1H, dd, J$_{2,1}$=7.70, J$_{2,3}$=9.52)
3  5.293 (1H, t, J$_{3,2}$=9.52)
4  5.213 (1H, t, J$_{4,3}$=J$_{4,5}$=9.52)
5  4.037 (1H, d, J$_{5,4}$=9.52)
—COOCH$_3$ 3.767 (3H, s)
—COCH$_3$ 2.092, 2.038, 2.027 (3H, s)×3

5) 54' (823.1 mg) was dissolved in methanol (10 ml), and to this solution was added 1M sodium methoxide (0.3 ml) at 0° C. The mixture was stirred at room temperature for 3 h. To this mixture were further added water (1 ml) and 1M sodium methoxide (0.3 ml), and the resulting mixture was stirred at room temperature for 2 h. After the solvent of the reaction solution was evaporated in vacuo, water (10 ml) was added to the residue, and the mixture was filtered. The filtrate was lyophilized to give crude 55β (580.0 mg). This crude product was purified by HPLC under similar conditions as in 4). Fractions containing the product were evaporated in vacuo, and then lyophilized to give 55β as white powder [54.5 mg (yield 8.2%)].

54'→55β

Compound 55β
MW: C$_{28}$H$_{37}$O$_{11}$F=568.59
MP: 188–190° C.
FAB(+)MS: m/z=569 (M+H)⁻, 591 (M+Na)⁻
IR ν$^{KBr}$ cm$^{-1}$: 3410(O—H), 2938 (C—H), 1716, 1662 (C=O), 1607(C—C)
$^1$H-NMR ppm, 500 MHz (CD$_3$OD, Ref=3.300 ppm (CH$_3$OD))

1  4.523 (1H, d, J$_{1,2}$=7.74 Hz)
2  3.482 (1H, dd, J$_{2,1}$=7.74, J$_{2,3}$=9.29)
3  3.554 (1H, t, J$_{3,2}$=J$_{3,4}$=9.29)
4  3.702 (1H, t, J$_{4,3}$=9.29, J$_{4,5}$=9.51)
5  3.954 (1H, d, J$_{5,4}$=9.73)

2. Synthesis of a toluoyl-protected derivative of β-glucuronyldexamethasone (toluoyl derivative)

1) D-Glucuronolactone 51 (4.86 g) was suspended in methanol (100 ml), and to this suspension was added sodium hydroxide (9.8 mg). The compounds were completely solubilized by ultrasonication. After the solvent of the reaction solution was evaporated in vacuo, pyridine (50 ml), p-toluoyl chloride and chloroform (20 ml) were added to the residue under ice-cooling, and, while the reaction temperature was slowly raised to room temperature, the mixture was stirred for 12 h. Water was added to the reaction mixture under ice-cooling, and the chloroform layer was washed successively with water, and saturated solutions of sodium bicarbonate and copper sulfate. After the chloroform solution was dried over anhydrous magnesium sulfate, the solvent was distilled off in vacuo. The residue thus obtained was purified by silica gel column chromatography (toluene:ethyl acetate=30/1→20/1) to give white powder [14.7 g (yield 78.2%)] consisting of 57α and 57β in a ratio of 1:1.5.

51→57
Compound 57

57α MS: $C_{39}H_{36}O_{11}$=680.706 MP: 83–85° C.
FAB(-)MS: m/a=679 (M—H)$^+$
IR $v^{KBr}$ cm$^{-1}$: 1736, 1613(C=O) 1265(C—C(=O)—O) 1100(O—C—C)
$^1$H-NMR (ppm, 500 MHz, CDCl$_3$, Ref=0.000 ppm (TMS))

1 6.874 (1H, d, $J_{1,2}$=3.66 Hz)
2 5.654 (1H, dd, $J_{2,1}$=3.66, $J_{2,3}$=9.89)
3 6.280 (1H, t, $J_{3,2}$=$J_{3,4}$=9.89)
4 5.721 (1H, t, $J_{4,3}$=$J_{4,5}$=9.89)
5 4.727 (1H, d, $J_{5,4}$=9.89)
—COOC$\underline{H}_3$ 3.669 (3H, s)
—C$_6$H$_4$C$\underline{H}_3$ 2.461, 2.372, 2.310, 2.304 (3H, s)×4
—C$_6$$\underline{H}_4$CH$_3$ 8.028, 7.866, 7.792, 7.754, 7.327, 7.191, 7.118, 7.084 (2H, d, J=8.06)×8

57β MW: $C_{39}H_{36}O_{11}$=680.706 MP: 92–95° C.
FAB(-)MS: m/z=679 (M—H)$^+$
IR $v^{KBr}$ cm$^{-1}$: 1734, 1613(C=O) 1266(C—C(=O)—O) 1094(O—C—C)
$^1$H-NMR (ppm, 500 MHz, CDCl$_3$, Ref=0.000 ppm (TMS))

1 6.627 (1H, d, $J_{1,2}$=7.33 Hz)
2 5.794 (1H, dd, $J_{2,1}$=7.33, $J_{2,3}$=8.79)
3 5.970 (1H, t, $J_{3,2}$=$J_{3,4}$=8.79)
4 5.767 (1H, t, $J_{4,3}$=$J_{4,5}$=8.79)
5 4.568 (1H, d, $J_{5,4}$=8.79)
—COOC$\underline{H}_3$ 3.606 (3H, s)
—C$_5$H$_4$C$\underline{H}_3$ 2.377, 2.326 (6H, s)×4
—C$_6$$\underline{H}_4$CH$_3$ 7.909, 7.850, 7.127, 7.116 (2H, d, J=8.06)×4 7.797, 7.185 (4H, d, J=8.06)×2.

2) 57 (6.22 g) was dissolved in dichloromethane (100 ml), and to this solution was added, under ice-cooling, a hydrobromide-acetic acid solution (40 ml). The mixture was stirred at room temperature for 12 h. After the reaction solution was washed with saturated sodium bicarbonate solution, the organic layer was dried over anhydrous magnesium sulfate. The solvent was evaporated in vacuo to give 58 as white powder [5.54 g (yield 96.3%)].

57→58
Compound 58

MS: $C_{31}H_{29}O_9Br$=625.468
MP: 83–84° C.
FAB(÷)MS: m/z=625, 627 (M+H)$^-$
IR $v^{KBr}$ cm$^{-1}$: 1733, 1613(C=O) 1266(C—C(=O)—O) 1106(O—C—C)

$^1$H-NMR (ppm, 500 MHz, CDCl$_3$, Ref=0.000 ppm (TMS))

1 6.884 (1H, d, $J_{1,2}$=4.03 Hz)
2 5.308 (1H, dd, $J_{2,1}$=4.03, $J_{2,3}$=9.89)
3 6.241 (1H, t, $J_{3,2}$=$J_{3,4}$=9.89)
4 5.692 (1H, t, $J_{4,3}$=$J_{4,5}$=9.89)
5 4.835 (1H, d, $J_{5,4}$=9.89)
—COOC$\underline{H}_3$ 3.677 (3H, s)
—C$_5$H$_4$C$\underline{H}_3$ 2.370, 2.358, 2.299 93H, s)×3
—C$_6$$\underline{H}_4$CH$_3$ 7.872, 7.864, 7.784, 7.196, 7.186, 7.107 (2H, d, $\overline{J}$=8.06)×6

3) Dexamethasone 6 (0.94 g) was dissolved in dehydrated tetrahydrofuran (100 ml), and to this solution were added, under an argon atmosphere, molecular sieve 5A (1.0 g) and 58 (1.98 g). To the resulting mixture was added, under ice-cooling, a solution (0.6 ml) of silver triflate (1.27 g) and tetramethylurea in dehydrated tetrahydrofuran, and, while the reaction temperature was slowly raised to room temperature, the resulting mixture was stirred for 1 h. After the reaction solution was filtered, the solvent was evaporated from the filtrate in vacuo, and the residue thus obtained was taken up in ethyl acetate (200 ml). After this solution was dried over anhydrous magnesium sulfate, the solvent was evaporated in vacuo. The residue thus obtained was purified by silica gel column chromatography (chloroform:methanol=60/1) followed by HPLC (column μ-Bondasphere C$_{18}$-100 Å, flow rate 23.0 ml/min, detection wave length 254 nm (UV), eluent A/B=water/95% acetonitrile (both containing 0.1% TFA)=30/70→0/100, eluted with the gradient 30 min). Fractions containing product were evaporated in vacuo, and then lyophilized to give 59α [50.0 mg (yield 2.2%)] and 58β[163.3 mg (yield 7.3%)], both as white powder.

58+6→59
Compound 59

59α MW: $C_{53}H_{57}O_{14}F$=937.23 MP: 146–150° C.
FAB(+)MS: m/z=937 (M+H)$^-$, 919 (M—OH)$^-$
IR $v^{KBr}$ cm$^{-1}$: 3414(O—H), 2948(C—H) 1732, 1660, 1613(C=O) 1267(C—C(=O)—O) 1106(0—C—C)
$^1$H-NMR (ppm, 500 MHz, CDCl$_3$, Ref=0.000 ppm (TMS))

1 5.465 (1H, d, $J_{1,2}$=4.03 Hz)
2 5.287 (1H, dd, $J_{2,1}$=4.03, $J_{2,3}$=9.89)
3 6.245 (1H, t, $J_{3,2}$=$J_{3,4}$=9.89)
4 5.370 (1H, t, $J_{4,3}$=$J_{4,5}$=9.89)
5 5.465 (1H, d, $J_{5,4}$=9.89)
—COOC$\underline{H}_3$ 3.623 (3H, s)
—C$_6$H$_4$C$\underline{H}_3$ 2.373, 2.355, 2.306 (3H, s)×3
—C$_5$H$_4$C$\underline{H}_3$ 7.862, 7.850, 7.784, 7.178, 7.165, 7.099 (2H, d, $\overline{J}$=8.06)×6

59β MW: $C_{53}H_{57}O_{14}F$=937.23 MP: 155–160° C.
FAB(+)MS: m/z=937 (M+H)$^-$, 919 (M—OH)$^-$
IR $v^{KBr}$ cm$^{-1}$ : 3440(O—H), 2950(C—H) 1733, 1667, 1613(C=O) 1280, 1265(C—C(=O)—O) 1097 (O—C—C)
$^1$H-NMR (ppm, 500 MHz, CDCl$_3$, Ref=0.000 ppm (TMS))

1 5.147 (1H, d, $J_{1,2}$=7.70 Hz)
2 5.533 (1H, dd, $J_{2,1}$=7.70, $J_{2,3}$=9.16)
3 5.911 (1H, t, $J_{3,2}$=9.16, $J_{3,4}$=9.52)
4 5.598 (1H, t, $J_{4,3}$=$J_{4,5}$=9.52)
5 4.317 (1H, d, $J_{5,4}$=9.52)
—COOC$\underline{H}_3$ 3.644 (3H, S)

—C$_6$H$_4$CH$_3$ 2.373, 2.359, 2.308 (3H, S)×3
—C$_6$H$_4$CH$_3$ 7.857, 7.811, 7.768, 7.187, 7.171, 7.106 (2H, d, J=8.06)×6

EXAMPLE 8

Figure 8:
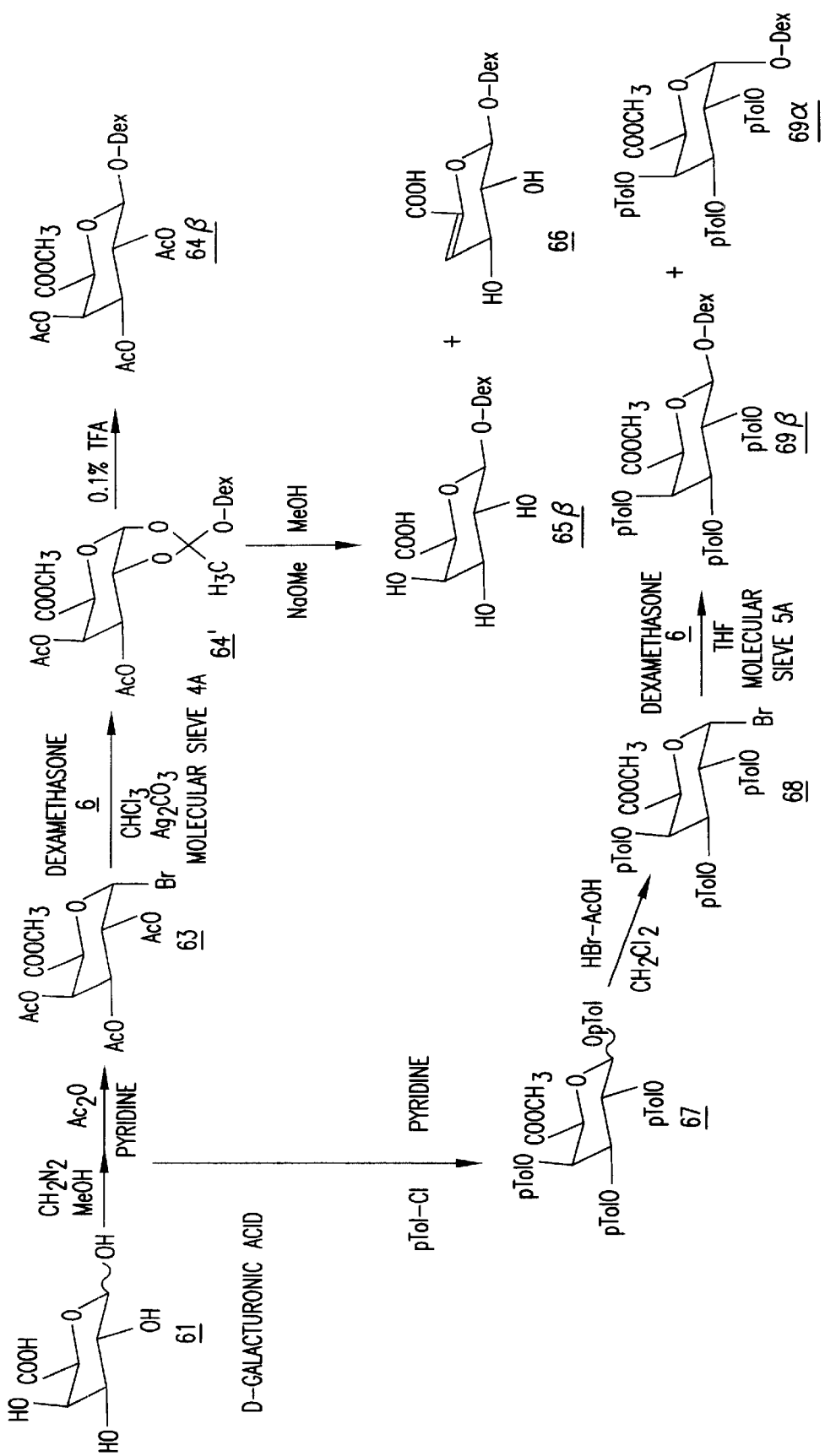
FIG. 8 is a flow-chart showing the synthesis route of β-galacturonyldexamethasone and Tol-protected derivative of β-galacturonyldexamethasone.

Synthesis of β-galacturonyldexamethasone and the toluoyl-protected derivative of β-galacturonyldexamethasone (FIG. 8)

1. Synthesis of β-galacturonyldexamethasone 1)
D-Galacturonic acid 61 (1.98 g) was dissolved in dehydrated methanol (100 ml), and to this solution was added a solution of diazomethane in ether in small portions under stirring until bubbling ceased. After the solvent was distilled off in vacuo, pyridine (4 ml) and acetic anhydride (8 ml) were added to the residue those obtained under ice-cooling, and, while the reaction temperature was slowly raised to room temperature, the resulting mixture was stirred for 24 h. Then, after the addition of methanol under ice-cooling, the solvent was distilled off in vacuo. The residue was dissolved in chloroform, washed with copper sulfate solution, and then the chloroform layer was evaporated in vacuo. After the residue was dissolved in chloroform (4 ml), a hydrogenebromide-acetic acid solution (10.0 ml) was added under ice-cooling, and the resulting mixture was stirred for 3.5 h. Then, to this mixture was added hydrogenbromide-acetic acid solution (2.0 ml) under ice-cooling, and the resulting mixture was stirred for 1 h. After the reaction solution was evaporated in vacuo, the residue was dissolved in chloroform (80 ml), washed with saturated sodium bicarbonate solution, and dried over anhydrous magnesium sulfate. The solvent was distilled off in vacuo, and the residue thus obtained was purified by silica gel column chromaography (toluene:ethyl acetate=4:1) to give 63 as white powder [1.17 g (yield 28.8%)].

61→63

Compound 63
MW: C$_{13}$H$_{17}$O$_9$Br=197.17
MP: 131–134° C.
FAB(+)MS: m/z=395, 397 (M+H⁻
IR ν$^{KBr}$ cm$^{-1}$: 1769, 1748(C=O), 1375(CH$_3$) 1232, 1218 (C—C(=O)—O)
$^1$H-NMR (ppm, 500 MHz, CDCl$_3$, Ref=0.000 ppm (TMS))
1 6.772 (1H, d, J$_{1,2}$=4.03 Hz)
2 5.108 (1H, dd, J$_{2,1}$=4.03, J$_{2,3}$=10.62)
3 5.456 (1H, dd, J$_{3,2}$=10.62, J$_{3,4}$=3.30)
4 5.833 91H, dd, J$_{4,3}$=3.30, J$_{4,5}$=1.1)
5 4.879 (1H, d, J$_{5,4}$=1.1)
—COOCH$_3$ 3.777 (3H, s)
—COCH$_3$ 2.111 (3H, s)
—COC$_3$2.024 (6H, s)

2) Dexamethasone 6 (0.82 g) was dissolved in chloroform (100 ml), and to this solution were added, under an argon atmosphere, molecular sieve 4A (1.57 g), silver carbonate (1.62 g) and 63 (1.02 g). The resulting mixture was stirred at room temperature for 2 days. After the reaction solution was filtered, the filtrate was washed with saturated sodium chloride solution, and dried over anhydrous magnesium sulfate. Evaporation of the solvent in vacuo gave crude 64'(1.86 g). Purification of crude 64' (0.16 g) by silica gel PLC plate (chloroform/methanol=20/1) gave 64' [0.041 g (yield 26.0%)] as white powder.

63+6→64'

Compound 64'
MW: C$_{35}$H$_{45}$O$_{14}$F=708.73
MP: 141–142° C.
FAB(+)MS: m/z=709(M+H)⁻
IR ν$^{KBr}$ cm$^{-1}$: 3454(O—H) 2950(C—H) 1757, 1665 (C=O) 1237(C—C(=O)—O)
$^1$H-NMR (ppm, 500 MHz, CDCl$_3$, Ref=0.000 ppm (TMS))
1 5.791 (1H, d, J$_{1,2}$=4.40 Hz)
2 4.273 (1H, dd, J$_{2,1}$=4.40, J$_{2,3}$=5.86)
3 5.260 (1H, dd, J$_{3,2}$=5.86, J$_{3,4}$=2.93)
4 5.791 (1H, dd, J$_{4,3}$=2.93, J$_{4,5}$=4.39)
5 4.867 (1H, d, J$_{5,4}$=4.39)
—COOCH$_3$ 3.753 (3H, s)
—COCH$_3$ 2.091, 2.074 (3H, s)
—CH$_3$ (ortho ester) 1.660 (3H, s)

3) 64' (277.4 mg) was dissolved in a mixture of acetonitrile/water [100 ml(4/96, containing 0.1% TFA)], and this solution was applied in 20 ml-portions to HPLC column (μ-Bondasphere C$_{18}$-100 Å, flow rate 23.0 ml/min, detection wave length 254 nm (UV), eluent A/B=water/95% acetonitrile (both containing 0.1% TFA)=94/6→80/20→38/62, eluted with the gradient for 30 min). Fractions containing product were evaporated in vacuo, and then lyophilized to give 64β as white powder [67.5 mg (yield 24.3%)].

64'→64β

Compound 64β
MW: C$_{35}$H$_{45}$O$_{14}$F=708.73
MP: 155–158° C.
FAB(+)MS: m/z=709 (M+H)⁻, 731 (M+Na)⁻
IR ν$^{KBr}$ cm$^{-1}$: 3406(O—H), 1754, 1665(C=O) 1225(C—C(=O)—O)
$^1$H-NMR (ppm, 500 HMz, CDCl$_3$, Ref=0.000 ppm (TMS))
1 4.893 (1H, d, J$_{1,2}$=8.06 Hz)
2 5.277 (1H, dd, J$_{2,1}$=8.06, J$_{2,3}$=10.26)
3 5.100 (1H, dd, J$_{3,2}$=10.26, J$_{3,4}$=3.29)
4 5.689 (1H, dd, J$_{4,3}$=3.29, J$_{4,5}$=1.46)
5 4.297 (1H, d, J$_{5,4}$=1.46)
—COOCH$_3$ 3.764 (3H, s)
—COCH$_3$ 2.144, 2.096, 2.001 (3H, s)×3

4) 64' (103.3 mg) was dissolved in methanol (5 ml), and to this solution was added 1M sodium methoxide (0.5 ml) at 0° C. The resulting solution was stirred at room temperature for 3 h. After the reaction solution was evaporated in vacuo, 1M sodium methoxide (0.5 ml) and water (1 ml) were added to the residue at 0° C., and stirred at room temperature for 2 h. The reaction solution was evaporated in vacuo, and then lyophilized, was purified by HPLC under similar conditions as in 3). Fractions containing the product were evaporated in vacuo, and then lyophilized to give 65β (29.5 mg (yield 35.5%)] and 66 [31.3 mg (yield 39.0%)], both as white powder.

64'→65β+66

Compound 65β
MW: C$_{28}$H$_{37}$O$_{11}$F=568.59
MP: 187°189° C.
FAB(+)MS: m/z=569 (M+H)⁻, 591 (M+Na)⁺
IR ν$^{KBr}$ cm$^{-1}$: 3414 (O—H), 1713, 1662(C=O) 1617, 1605(C—C)
$^1$H-NMR (ppm, 500 MHz, CD$_3$OD, Ref=3.300 ppm (CH$_3$OD))
1 4.134 (1H, d, J$_{1,2}$=7.70 Hz)
2 3.617 (1H, dd, J$_{2,1}$=7.70, J$_{2,3}$=9.89)

3 3.558 (1H, dd, $J_{3,2}$=9.89, $J_{3,4}$=3.30)

4 4.157 (1H, dd, $J_{4,3}$=3.30, $J_{4,5}$=1.10)

5 4.217 (1H, d, $J_{5,4}$=1.10)

Compound 66
MS: $C_{28}H_{35}O_{10}F$=550.58
MP: 183–184° C.
FAB(+)MS: m/z=551 (M+H)⁻, 573 (M+Na)⁻
IR $v^{KBr}$ cm⁻¹: 3414(O—H), 1713, 1662(C=O) 1617, 1605 (C—C), 1242(C—C(=O)—O)
¹H-NMR (ppm, 500 MHz, CD₃OD, REF=3.300 ppm (CH₃OD))

1 6.151 (1H, d, $J_{1,2}$=4.03 Hz)

2 4.012 (1H, t, $J_{2,1}$=$J_{2,3}$=4.03)

3 3.868 (1H, t, $J_{3,2}$=$J_{3,4}$=4.03)

4 5.098 (1H, d, $J_{4,3}$=4.40)

2. Synthesis of Toluyl-protected Derivative of β-galacturonyldexamethasone

1) D-Galacturonic acid 61 (1.12 g) was dissolved in dehydrated methanol (30 ml), and to this solution was added, under stirring, diazomethane in ether in small portions until bubbling ceased. After removal of the solvent in vacuo, pyridine (5 ml), p-toluoyl chloride (5 ml) and chloroform (10 ml) were added to the residue under ice-cooing, and the resulting mixture was stirred for 4 h, while the reaction temperature was slowly raised to room temperature. Then, to the reaction mixture was added water under ice-cooling, and the chloroform layer was washed successively with water, saturated solutions of sodium bicarbonate and copper sulfate. After the solution was dried over anhydrous magnesium sulfate, the solvent was distilled off in vacuo. Purification of the residue thus obtained by silica gel column chromatography (toluene:ethyl acetate=40/1→30/1) gave 67 as white powder [782.7 mg (yield 20.2%)].

61→67

Compound 67β
MW: $C_{39}H_{36}O_{11}$=680.706
MP: 180–182° C.
FAB(-)MS: m/z=679 (M—H)⁻
IR$v^{KBr}$ cm⁻¹: 1771, 1733, 1613(C=O) 1267(C—C(=O)—O), 1093(O—C—C)
¹H-NMR(ppm, 500 MHz, CDCl₃, Ref=0.000 ppm(TMS))

1 6.215 (1H, d, $J_{1,2}$=8.06 Hz)

2 6.065 (1H, dd, $J_{2,1}$=8.06, $J_{2,3}$=10.26)

3 5.733 (1H, dd, $J_{3,2}$=10.26, $J_{3,4}$=3.30)

4 6.207 (1H)

5 4.809 (1H, d, $J_{5,4}$=1.47)

—COOCH₃ 3.700 (3H, s)

—C₆H₄CH₃ 2.434, 2.378, 2.310, 2.296 (3H, s)×4

—C₆H₄CH₃ 7.953, 7.951, 7.769, 7.710, 7.266, 7.205, 7.101, 7.072 (2H, d, J=8.06)×8

2) 67 (70.3 mg) was dissolved in dichloromethane (5 ml), and to this solution was added, under ice-cooling, a hydrogenbromide-acetic acid solution (2 ml). The mixture was stirred at room temperature for 2 h. The reaction solution was washed with saturated sodium bicarbonate solution, and then dried over anhydrous magnesium sulfate. Evaporation of the solvent in vacuo gave 68 [44.6 mg (yield 69.2%)] as white powder.

67→68

Compound 68
MW: $C_{31}H_{29}O_9Br$=625.468
FAB(+)MS: m/z=625, 627 (M+H)⁻
¹H-NMR(ppm, 500 MHz, CDCl₃, Ref=0.000 ppm(TMS))

1 7.003 (1H, d, $J_{1,2}$=4.03 Hz)

2 5.612 (1H, dd, $J_{2,1}$=4.03, $J_{2,3}$10.26)

3 6.006 (1H, dd, $J_{3,2}$=10.26, $J_{3,4}$=3.30)

4 6.255 (1H, dd, $J_{4,3}$=3.30, $J_{4,5}$=1.46)

5 5.132 (1H, d, $J_{5,4}$=1.46)

—COOCH₃ 3.724 (3H, s)

—C₆H₄CH₃ 2.429, 2.359, 2.316 (3H, s)×3

—C₆H₄CH₃ 7.895, 7.866, 7.695, 7.710, 7.254, 7.183, 7.073 (2H, d, J=8.06)×6

3) Dexamethasone 6 (88.0 mg) was dissolved in dehydrated tetrahydrofuran (10 ml), and to this solution were added, under an argon atmosphere, molecular sieve 5A (1.0 g) and 68 (100.8 mg) dissolved in dehydrated tetrahydrofuran (10 ml). Then, to the resulting mixture were added, under ice-cooling, silver triflate (82.2 mg) dissolved in dehydrated tetrahydrofuran (2 ml) and tetramethylurea (0.25 ml), and, while the reaction temperature was slowly raised to room temperature, the resulting mixture was stirred for 2 h. The reaction solution was filtered, and the solvent of the filrate was evaporated in vacuo. The residue thus obtained was dissolved in ethyl acetate (100 ml), washed with saturated sodium chloride solution. The solvent of the solution was evaporated in vacuo. The residue thus obtained was purifed by HPLC (column: μ-Bondasphere $C_{18}$-100 Å, flow rate 23.0 ml/min, detection wave length 254 nm (UV), eluent A/B=water/95% acetonitrile (both containing 0.1% TFA)=30/70→0/100, eluted with gradient for 30 min). Fractions containing product were evaporated in vacuo, and lyophilized to give 69 α [9.5 mg (yield 4.6%)] and 69β [38.1 mg (yield 18.5%)], both as white powder.

68+6→E

Compound 69
69α
MW: $C_{53}H_{57}O_{14}F$=937.023
MP: 161–167° C.
FAB(+)MS: m/z=937 (M+H)⁻, 919 (M—OH)⁺
IR $v^{KBr}$ cm⁻¹: 3414(O—H), 2928(C—H) 1731, 1667, 1612 (C=O), 1283, 1267(C—C(=O)—O), 1095(O—C—C)
¹H-NMR(ppm, 500 MHz, CDCl₃, Ref=0.000 ppm(TMS))

1 5.542 (1H, d, $J_{1,2}$=4.03 Hz)

2 5.634 (1H, dd, $J_{2,1}$=4.03, $J_{2,3}$=10.63)

3 6.065 (1H, dd, $J_{3,2}$=10.63, $J_{3,4}$=3.30)

4 6.251 (1H, dd, $J_{4,3}$=3.30, $J_{4,5}$=1.46)

5 5.231 (1H, d, $J_{5,4}$=1.46)

—COOCH₃ 3.678 (3H, s)

—C₆H₄CH₃ 2.424, 2.347, 2.310 (3H, s)×3

—C₆H₄CH₃ 7.894, 7.858, 7.696, 7.244, 7.156, 7.061 (2H, d, J=8.06)×6

69β
MW: $C_{53}H_{57}O_{14}F$=937.023
MP: 161–165° C.
FAB(+)MS: 937 (M+H)⁻, 919 (M—OH)⁻
IR $v^{KBr}$ cm⁻¹: 3412(O—H), 2930(C—H), 1733, 1666, 1612 (C=O), 1283, 1266(C—C(=O)—O), 1095(O—C—C)
¹H-NMR(ppm, 500 MHz, CDCl₃, Ref=0.000 ppm(TMS))

1 5.151 (1H, d, $J_{1,2}$=8.42 Hz)

2 5.904 (1H, dd, $J_{2,1}$=8.42, $J_{2,3}$=10.26)

3 5.632 (1H, dd, $J_{3,2}$=10.26, $J_{3,4}$=3.30)

4 6.029 (1H, dd, $J_{4,3}$=3.30, $J_{4,5}$=1.10)

5 5.565 (1H, d, $J_{5,4}$=1.10)

—COOCH$_3$ 3.760 (3H, s)

—C$_6$H$_4$CH$_3$ 2.373, 2.361, 2.299 (3H, s)×4

—C$_6$H$_4$CH$_3$ 7.975, 7.852, 7.706, 7.285, 7.178, 7.071 (3H, d, J=8.06)×6

EXAMPLE 9

Figure 9:
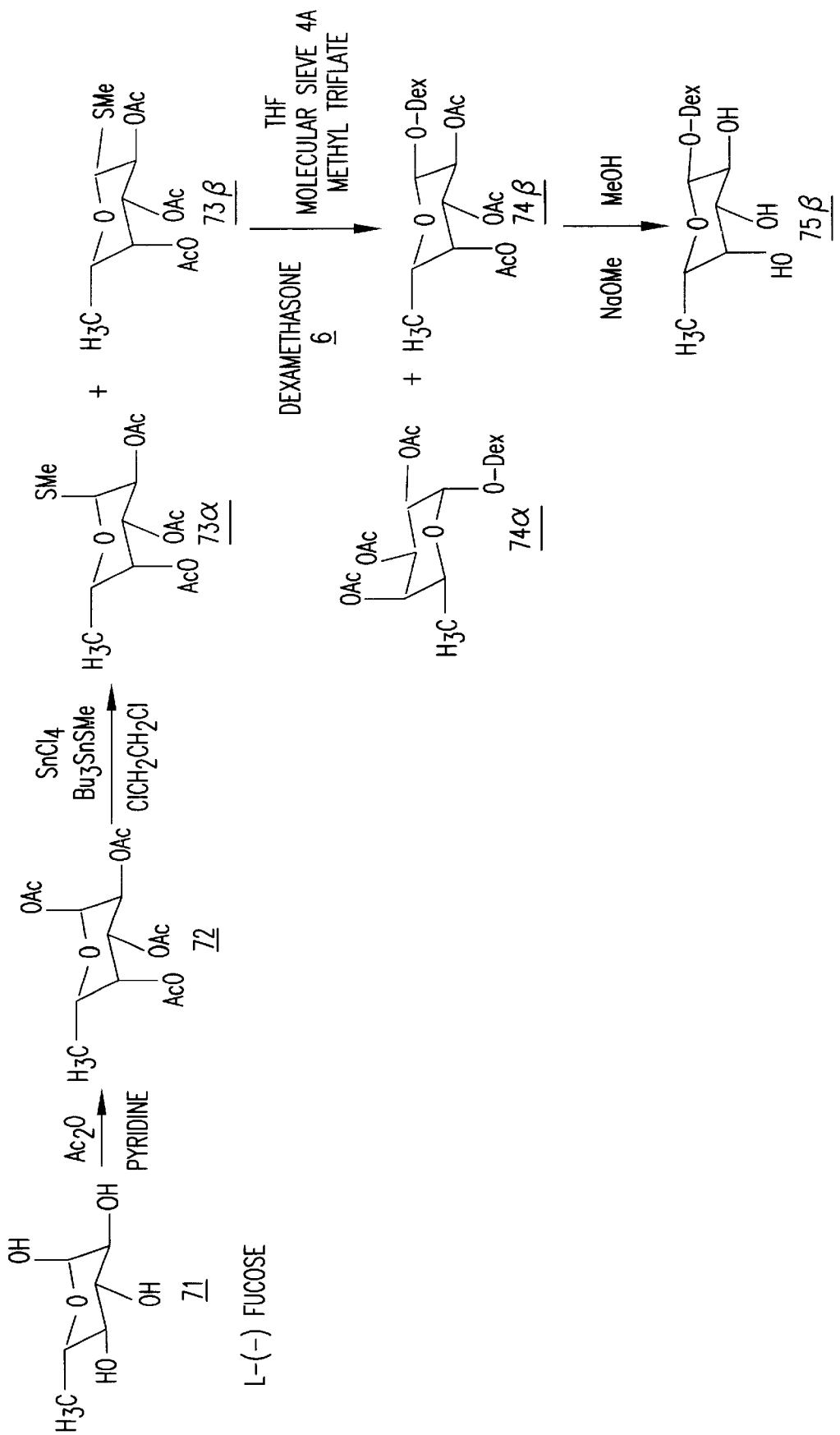
FIG. 9 is a flow-chart showing the synthesis route of β-fucosyldexamethasone.

Synthesis of β-fucosyldexamethasone (FIG. 9)

1) Synthesis of SMe derivative of fucose (71→72→73α+73β)

L-(−)Fucose 71 [3.0 g (18.27 mmol)] was suspended in acetic anhydride (30 ml), and to this solution was added, at 0° C., pyridine (7.1 ml) drop-wise. The mixture was stirred at room temperature overnight. The reaction solution was poured into ice-water, and extracted with chloroform four times. After the chloroform layer was washed successively with copper sulfate solution, water three times, and saturated sodium chloride solution. After the organic layer was dried over anhydrous magnesium sulfate, the solvent was distilled off in vacuo. The residue thus obtained was dissolved in ethyl acetate, and allwed to stand at 30° C. for 2 days. Precipitated crystals were collected by filtration, weighing 2.98 g (yield 51.6%) of 72 as white powder. The product thus obtained [2.0 g (6.32 mmol)] and Bu$_3$SnSMe [3.20 g (9.48 mmol)] were dissolved in dichloroethane (20 ml), and to this solution was added at 0° C. tin (IV) chloride [0.96 ml (8.22 mmol)] drop-wise. The mixture was stirred at room temperature overnight. The reaction solution was diluted with chloroform, and to this mixture was added potassium fluoride. After stirring, the mixture was filtered through celite. The chloroform layer of the filtrate was washed with saturated sodium bicarbonate, water and saturated sodium chloride solution, dried over anhydrous magnesium sulfate, and the solvent was distilled off in vacuo. Purification of the residue thus obtained by silica gel column chromatorgraphy (ethyl acetate: toluene=1:6) gave α-anomer (73α) [164.2 mg (yield 8.1%)] and β-anomer (73β) [1.483 g (yield 73.2%)], both as white powder.

Compound 73α
C$_{13}$H$_{20}$O$_7$S
MW: 320.36
MP: 78–80° C.
FAB(+)MS: 321 (M+H)$^-$, 641 (2M+H)$^+$
IRν$^{KBr}$ cm$^{-1}$: 1755, 1742(OCOCH$_3$)
$^1$H-NMR [500 MHz, CDCl$_3$, Ref=0.000 ppm(TMS)]
δ; 1.169 (3H, d, J=6.6 Hz, H-6)

1.991, 20.53, 2.071, 2.170 (each 3H, 4s, SCH$_3$+3Ac)

4.449 (1H, q, J=6.6 Hz, H-5)

5.239 (1H, dd, J=3.3, 10.6 Hz, H-3)

5.291 (1H, dd, J=5.5, 10.6 Hz, H-2)

5.299 (1H, dd, J=0.7, 3.3 Hz, H-4)

5.568 (1H, d, J=5.5 Hz, H-1)

Compound 73β
C$_{13}$H$_{20}$O$_7$S
MW: 320.36
MP: 146–147° C.
FAB(+)MS: 321 (M+H)$^-$, 641 (2M+H)$^-$
IR ν$^{KBr}$ cm$^{-1}$: 1746(OCOCH$_3$)
$^1$H-NMR [500 MHz, CDCl$_3$, Ref=0.000 ppm(TMS)]
δ; 1.224 (3H, d, J=6.2 Hz, CH$_3$-6)

1.990, 2.074, 2.178, 2.200 (each 3H, 4s, SCH$_3$+3Ac)

3.850 (1H, dq, J=1.1, 6.2 Hz, H-5)

4.361 (1H, d, J=9.9 Hz, H-1)

5.057 (1H, dd, J=3.3, 9.9 Hz, H-3)

5.248 (1H, t, J=9.9 Hz, H-2)

5.282 (1H, dd, J=1.1, 3.3 Hz H-4)

2) Synthesis of a protected derivative of fucosyldexamethasone

To a mixture of dexamethasone (6) [51 mg (0.130 mmol)], β-anomer (73β) of fucose SMe-derivative [50 mg (0.156 mmol)] and molecular sieve 4A (100 mg) was added tetrahydrofuran (about 1 ml), and then, under an argon atmoshere at −20° C., methyl triflate (36 μl) was added. After stirring at room temperature for 2.5 h, the reaction mixture was neutralized with Et$_3$N, diluted with ethyl acetate, and filtered. The filtrate was washed successively with saturated solutions of sodium bicarbonate and sodium chloride. After the solution was dried over anhydrous magnesium sulfate, the solvent was evaporated in vacuo. Purification of the residue thus obtained by silica gel column chromatography (ethyl acetate:toluene=1:1) gave α-anomer (74α) [6.5 mg (yield 7.5%)] and β-anomer (74β) [20.9 mg (yield 24.2%)], both as white powder.

73β+dexamethasone (6)→74α+74β

Compound 74α (fuc(OAc)dexa(α))
C$_{34}$H$_{45}$FO$_{12}$ MW=664.72
MP: 120–121° C.
FAB(+)MS 655 (M+H)$^-$
IR ν$^{KBr}$ cm$^{-1}$ 3470(O—H), 1750(C=O of OAc), 1662 (C=O at position-3) 1622, 1604(C=C), 1070, 1058 (C—O of OH)
$^1$H-NMR(500 MHz, CDCl$_3$, Ref=0.000 ppm(TMS))
δ: 0.896 (3H, d, J=6.6 Hz, 16-CH$_3$)

1.028 (3H, s, CH$_3$)

1.150 (3H, d, J=6.6 Hz, H$_3$-6$_{fuc}$)

1.543 (3H, s, CH$_3$)

2.000 (3H, s, Ac)

2.171 (6H, s, 2Ac)

4.253 (1H, q, J=6.6 Hz, H-5$_{fuc}$)

4.386 (1H, d, J=17.2 Hz, H-21)

4.516 (1H, d, J=17.2 Hz, H'-21)

5.028 (1H, d, J=3.7 Hz, H-1$_{fuc}$)

5.171 (1H, dd, J=3.7, 11.0 Hz, H-2$_{fuc}$)

5.310 (1H, dd, J=1.1, 3.3 Hz, H-4$_{fuc}$)

5.436 (1H, dd, J=3.3, 11.0 Hz, H-3$_{fuc}$)

6.112 (1H, s, H-4)

6.331 (1H, dd, J=1.8, 10.3 Hz, H-1)

7.189 (1H, dd, J=10.3 Hz, H-2)

Compound 74β (fuc(OAc)dexa(β))
C$_{34}$H$_{45}$FO$_{12}$ MW=664.72
MP: 134–137° C.
FAB(+)MS 665 (M+H)$^-$
IRν$^{KBr}$ cm$^{-1}$ 3494(O—H), 1754(OCOCH$_3$) 1666(C=O), 1623, 1604(C=C), 1075, 1035(C—O)
$^1$H-NMR (500 MHz, CDCl$_3$, Ref=0.000 ppm(TMS))
δ: 0.905 (3H, d, J=7.3 Hz, 16-CH$_3$)

0.993 (3H, s, CH$_3$)

1.220 [3H, d, J=6.6 Hz, H$_3$-6(fuc)]

1.549 (3H, s, CH$_3$)

1.998, 2.113, 2.167 (each 3H, 3s, 3OAc)

3.806 [1H, d, J=0.7, 6.6 Hz, H-5(fuc)]

4.484 (1H, d, J=16.5 Hz, H-21)

4.562 (1H, d, J=16.5 Hz, H'-21)

5.564 [1H, d, J=7.7 Hz, H-1(fuc)]

5.040 [1H, dd, J=3.3, 10.6 Hz, H-3(fuc)]

5.227 [1H, dd, J=7.7, 10.6 Hz, H-2(fuc)]

5.240 [1H, dd, J=3.3, 0.7 Hz, H-4(fuc)]

6.110 (1H, s, H-4)

6.325 (1H, dd, J=2.2, 9.9 Hz, H-1)

7.237 (1H, d, J=9.9 Hz, H-2)

3) Synthesis of deprotected derivative of fucosyldexamethasone (74β→75β)

A protected derivative of fucosyldexamethasone (74β) [112.4 mg (0.169 mmol)] was dissolved in methanol (1 ml), and to this solution was added 1M sodium methoxide (35 μl). The mixture was stirred at room temperature for 1 h. The reaction solution was applied to a gel filtration column of LH-20, and eluted with methanol. Evaporation of the solvent of fractions containing the product in vacuo gave 75β [79.4 mg (yield 87.2%) as white powder.

Compound 75β

$C_{28}H_{39}FO_9$ MW=538.61

MP: 161–164° C.

FAB(+)MS 539 (M+H)$^-$

IR$\nu^{KBr}$ cm$^{-1}$ 3418 (OH) 1717, 1665 (C=O), 1622, 1602 (C=C)

$^1$H-NMR (500 MHz, CD$_3$OD, Ref=3.350 ppm (CH$_3$OD)

δ: 0.906 (3H, d, J=7.3 Hz, 16-CH$_3$)

1.054 (3H, s, CH$_3$)

1.318 (3H, s, J=6.6 Hz, H$_3$-6$_{fuc}$)

1.628 (3H, s, CH$_3$)

3.516 (1H, dd, J=3.3, 9.9 Hz, H-3$_{fuc}$)

3.604 (1H, dd, J=7.3, 9.9 Hz, H-2$_{fuc}$)

3.631 (1H, d, J=3.3 Hz, H-4$_{fuc}$)

3.682 (1H, q, J=6.6 Hz, H-5$_{fuc}$)

4.239 (1H, d, J=7.3 Hz, H-1$_{fuc}$)

4.683 (2H, s, H$_2$-21)

6.120 (1H, s, H-4)

6.329 (1H, dd, J=1.8, 10.3 Hz, H-1)

7.445 (1H, d, J=10.3 Hz, H-2)

EXAMPLE 10

Figure 10:
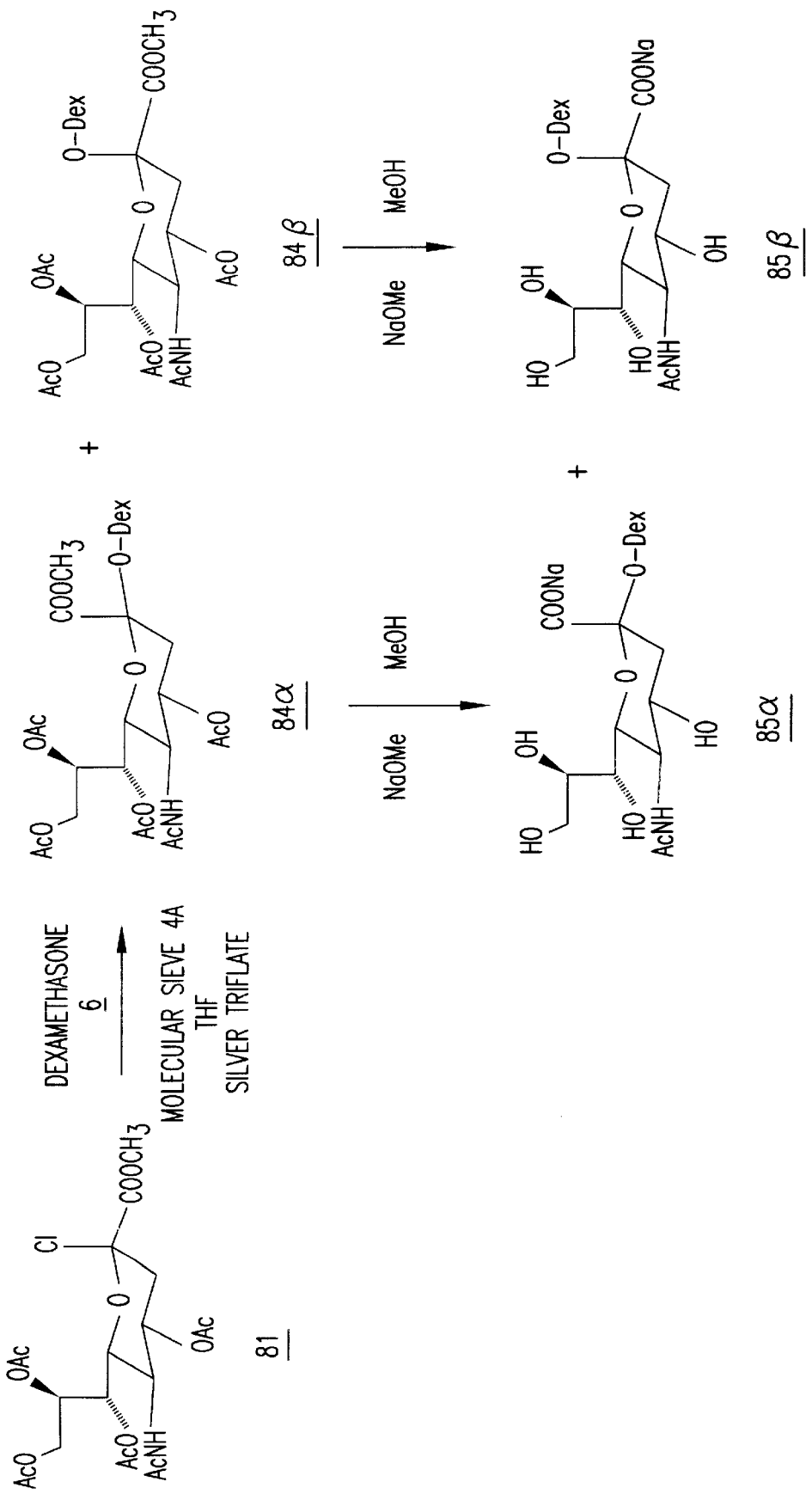
FIG. 10 is a flow-chart showing the synthesis route of sodium salt of sialyldexamethasone.

Synthesis of sodium salt of sialydexamethasone (FIG. 10)

1) Synthesis of a protected derivative of sialyl dexamethasone

Methyl 2-chloro-4,7,8,9-tetra-O-acetyl-N-acetylneuraminate (81) was synthesized by the method described in Carbohy. Res. 158 (1986), 35–51.

Dexamethasone (6) [7.0 g (18.0 mmol)] was dissolved in tetrahydofuran (130 ml), and to this solution were added molecular sieve 4A (70 g) and methyl 2-chloro-4,7,8,9-tetra-O-acetyl-N-acetylneuraminate (81) [11.08 g (21.6 mmol)]. To this mixture was added, under an argon atmosphere, a solution of silver triflate [5.60 g (21.6 mmol)] in tetrahydrofuran at −40° C. Wile the reaction temperature was slowly raised to room temeprature, the mixture was stirred for 1.5 h. To this mixture was further added 81 [4.63 g (9.0 mmol)], and the resulting mixture was stirred at room temperature overnight. After the reaction solution was filtered, the solvent of the filtrate was evaporated in vacuo. The residue was dissolved in ethyl acetate (200 ml), washed with saturated sodium chloride solution and dried over anhydrous magnesium sulfate. After the solvent was distiled off in vacuo, the residue thus obstasined was purified by silica gel column chromatography (chloroform:methanol=20:1) to give (84α) [9.26 g (yield 59.4%)] as white powder, yellow powder (3.99 g) and the starting material (6) recovered [1.72 g (24.6% recovery)]. Recrystallization of 84α from ethyl acetate gave 84α as white crystals (5.89 g). Purification of yellow powder (3.9 g) by HPLC (silica gel cartridge colun, eluent chloroform: methanol=100:1→50:1) gave 84β as white powder [1.80 g (yield 11.67%)].

Compound 84α (crystals)

$C_{42}H_{56}FNO_{17}$

MW=865.90

MP=156° C.

FAB(+)MS 866 (M+H)$^-$

IR$\nu^{KBr}$ cm$^{-1}$: 3520 (OH,NH), 1749, 1666 (C=O), 1624 (C=C), 1540 (NH), 1039 (C—O)

$^1$H-NMR [500 MHz, CDCl$_3$, Ref=0.000 ppm (TMS)]

δ:0.926 (3H, d, J-7.3 Hz, 16-CH$_3$)

1.015 (3H, s, CH$_3$)

1.537 (3H, s, CH$_3$)

1.877, 2.029, 2.044, 2.148, 2.159 (each 3H, 5s, 5Ac)

2.794 (1H, dd, J=4.8, 12.8 Hz, H-3$_{eq\ NeuNAc}$)

3.748 (1H, dd, J=2.2, 10.6 Hz, H-6$_{NeuNAc}$)

3.788 (1H, s, COOCH$_3$)

4.022 (1H, dd, J=5.9, 12.5 Hz, H-9$_{NeuNAc}$)

4.029 (1H, t, J=10.6 Hz, H-5$_{NeuNAc}$)

4.261 (1H, dd, J=2.6, 12.5 Hz, H'-9$_{NeuNAc}$)

4.278 (1H, d, J=18.7 Hz, H-21)

4.920 (1H, ddd, J=4.8, 10.6, 12.1 Hz, H-4$_{NeuNAc}$)

5.105 (1H, d, J=18.7 Hz, H'-21)

5.121 (1H, d, J=9.9 Hz, NH)

5.285 (1H, dd, J=2.2, 9.5 Hz, H-7$_{NeuNAc}$)

5.474 (1H, ddd, J=2.6, 5.9, 9.5 Hz, H-8$_{NeuNAc}$)

6.106 (1H, s, H-4)

6.324 (1H, dd, J=1.8, 10.3 Hz, H-1)

7.212 (1H, d, J=10.3 Hz, H-2)

81+6→84α+84β

Compound 84β (crystals)

$C_{42}H_{56}FNO_{17}$

MW=865.90

MP=194–197° C.

FAB (+) MS 866 (M+H)$^-$, 888 (M+Na)$^-$ $^1$H-NMR [500 MHz, CDCl$_3$, Ref=0.000 ppm (TMS)]

δ; 0.857 (3H, d, J=7.3 Hz, 16-CH$_3$)

1.031 (3H, s, CH$_3$)

1.547 (3H, s, CH$_3$)

1.896, 1.995, 2.027, 2.044, 2.153 (each 3H, 5s, 5Ac)

2.553 (1H, dd, J=5.1, 12.8 Hz, H-3$_{eq\ NeuNAc}$)

3.885 (1H, dd, J=10.3, 12.8 Hz, H-9$_{NeuNAc}$)

4.093 (1H, q, J=10.3 Hz, H-5$_{NeuNAc}$)

4.378 (1H, dd, J=2.2, 10.3 Hz, H-5$_{NeuNAc}$)

4.498 (1H, d, J=17.6 Hz, H-21)

4.796 (1H, d, J=17.6 Hz, H'-21)

5.114–5.156 (2H, m, H-8$_{NeuNAc}$+H'-9$_{NeuNAc}$)

5.379 (1H, s, J=2.2 Hz, H-7$_{NeuNAc}$)

5.399 (1H, dt, J=5.1, 10.3 Hz, H-4$_{NeuNAc}$)

5.520 (1H, d, J=10.3 Hz, NH)

6.113 (1H, s, H-4)

6.331 (1H, dd, J=1.8, 10.3 Hz, H-1)

7.211 (1H, d, J=10.3 Hz, H-2)

IR $\nu^{KBr}$ cm$^{-1}$: 3572, 3494 (OH,NH) 1767, 1755, 1735, 1663(C=O), 1625, 1605 (C=C)

2) Synthesis of a deprotected derivative of sialyldexamethasone (α)

84α [2.98 g (3.45 mmol)] was dissolved in methanol (20 ml), and to this solution was added 1M sodium methoxide (0.7 ml) at 0° C. The mixture was stirred at room temperature for 2 h. The solvent was distilled off from the reaction mixture in vacuo, and to the residual material were added water (10 ml) and 1M sodium methoxide (3.4 ml). The mixture was stirred at room temperature for 30 min. Then the reaction solution was applied to a gel filtration column of LH-20, and eluted with methanol. The solvent was distilled off from fractions containing product in vacuo to give 85α as white powder [2.30 g (94.7%)]. 85α was further recrystallized from methanol to give colorless crystals (1.20 g).

Compound 85α (crystals)
$C_{33}H_{45}FNO_{13}Na$
MW=705.71
MP=214° C. (decomp.)
FAB (+) MS 706 (M+H)$^-$, 728 (M+Na)$^-$
IR $v^{KBr}$ cm$^{-1}$: 3374 (OH,NH), 1727, 1664 (C=O), 1615 (COONa), 1559 (NH), 1069, 1041 (C—O)
$^1$H-NMR [500 MHz, CD$_3$OD, Ref=0.000 ppm(TMS)]
δ; 0.839 (3H, d, J=7.3 Hz, 16-CH$_3$)
    1.008 (3H, s, CH$_3$)
    1.583 (3H, s, CH$_3$)
    1.705 (1H, t, J=12.1 Hz, H-3$_{ax\ NeuNAc}$)
    2.010 (3H, s, Ac)
    2.880 (1H, dd, J=4.4, 12.1 Hz, H-3$_{eq\ NeuNAc}$)
    3.442 (1H, dd, J=2.2, 9.2 Hz, H-7$_{NeuNAc}$)
    3.597 (1H, dd, J≦6.6, 11.4 Hz, H-9$_{NeuNAc}$)
    3.836 (1H, dd, J=2.2, 11.4 Hz, H'-9$_{NeuNAc}$)
    3.905 (1H, ddd, J=2.2, 6.6, 9.2 Hz, H-8$_{NeuNAc}$)
    4.595 (1H, d, J=18.7 Hz, H-21)
    4.683 (1H, d, J=18.7 Hz, H'-21)
    6.068 (1H, s, H-4$_{NeuNAc}$)
    6.281 (1H, dd, J=1.8, 10.3 Hz, H-1)
    7.408 (1H, d, J=10.3 Hz, H-2)

84α→85α

3) Synthesis of a deprotected derivative of sialyldexamethasone (β)

84β [506.1 mg (0.584 mmol)] was dissolved in methanol (50 ml), and to this solution was added 1M sodium methoxide (0.7 ml). The mixture was stirred at room temperature for 2 h. The solvent was distilled off from the reaction solution in vacuo, and to the residue were added water (3ml), 1M sodium methoxide (0.58 ml) and methanol (1 ml). The resulting mixture was stirred at room temperature for 1 h. Then the reaction solution was applied to a gel filtration column of LH-20, and eluted with methanol. The solvent was distilled off from fractions containing product in vacuo to give 85β as white powder [389.3 mg (yield 94.5%)].

Compound 85β
$C_{33}H_{45}FNO_{13}Na$
MW=705.71
MP=228–229° C. (decomp.)
FAB (+) MS 706 (M—H)$^-$, 728 (M+Na)$^-$
$^1$H-NMR [500 MHz, CD$_3$OD, Ref=0.000 ppm (TMS)]
δ; 0.826 (3H, d, J=7.3 Hz, 16-CH$_3$)
    1.001 (3H, s, CH$_3$)
    1.587 (3H, s, CH$_3$)
    1.979 (3H, s, Ac)
    2.448 (1H, dd, J=5.1, 12.8 Hz, H-3$_{eq\ NeuNAc}$)
    3.408 (1H, d, J=10.3 Hz, H-6$_{NeuNAc}$)
    3.643 (1H, dd, J=5.1, 11.4 Hz, H-9$_{NeuNAc}$)
    3.714 (1H, d, J=10.3 Hz, H-7$_{NeuNAc}$)
    3.787 (1H, dd, J=2.9, 11.4 Hz, H'-9$_{NeuNAc}$)
    3.950 (1H, t, J=10.3 Hz, H-5$_{NeuNAc}$)
    4.109 (1H, dt, J=5.1, 10.3 Hz, H-4$_{NeuNAc}$)
    4.300 (1H, d, J=18.3 Hz, H-21)
    4.611 (1H, d, J=18.3 Hz, H'-21)
    6.068 (1H, s, H-4)
    6.289 (1H, dd, J=1.8, 9.9 Hz, H-1)
    7.419 (1H, d, J=9.9 Hz, H-2)
IR $v^{KBr}$ cm$^{-1}$: 3400 (OH, NH), 1721, 1633(C=O), 1623 (COONa), 1560(NH), 1067, 1023(C—O),

84β→85β

EXAMPLE 11

Figure 11:
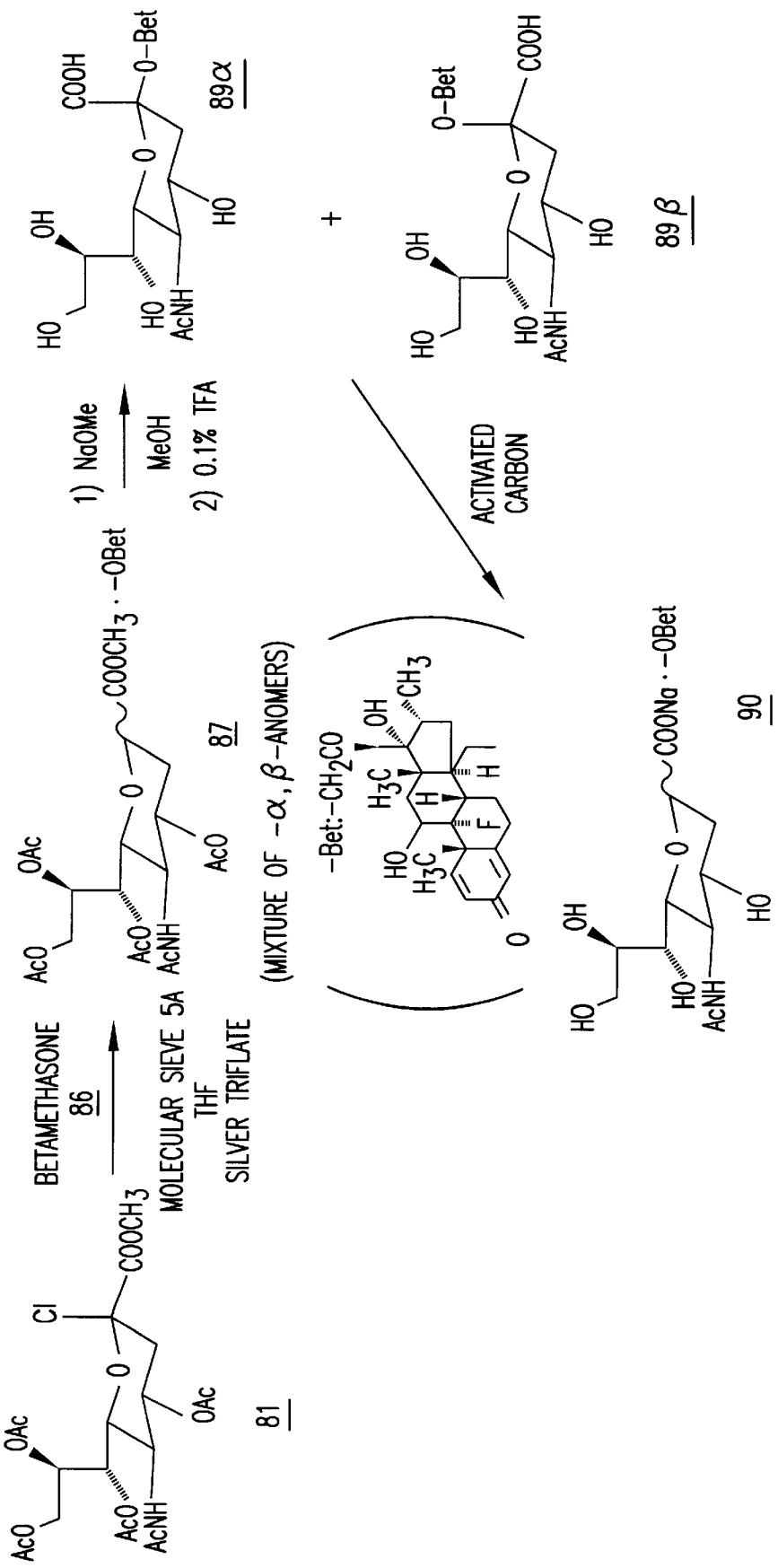
FIG. 11 is a flow-chart showing the synthesis route of sialylbetamethasone.

Synthesis of sialylbetamethasone (FIG. 11)

1) Sialylbetamethasone (glycosulation)

Betamethasone (86) (1.0 g) was dissolved in tetrahydrofuran (20 ml), and to this soultion were added silver triflate (1.31 g) and molecular sieve 5A (1.0 g). To this mixture was added, under an argon atmosphere and at −40° C., a solution of methyl 2-chloro-4,7,8,9-tetra-O-acetyl-N-acetylneuraminate (81) (2.08 g) in terahydrofuran. While the reaction temperature was slowly raised to room temperature, the mixture was stirred for 5 h. The reaction solution was filtered, and the solvent was distilled off from the filtrate in vacuo. The residue was dssolved in chloroform, and the solution was washed with satuerated sodium chloride solution. After the chloroform solution was dried over anhydrous magnesium sulfate, the solvent was distilled off in vacuo. The residue thus obtained was purified by silica gel column chromatography (chloroform:methanol=15:1), and further purified by Lobar column using silica gel column (diisopropyl ether:methanol=5:1) to give 87 as white powder [953.9 mg (yield 43.4%)].

81+86→87

Compound 87
$C_{42}H_{56}FNO_{17}$ MW=865.90
$^1$H-NMR [500 MHz, CDCl$_3$, Ref 0.00 ppm (TMS)]
NeuAc
    3 eq 2.813 (1H, dd, J$_{3ax,3eq}$=4.76, J$_{3eq,4}$=12.46)
    4 4.896 (1H, ddd, J$_{4,5}$=10.26)
    5 4.058 (1H, t, J$_{5,6}$=10.63)
    6 3.727 (1H, dd, J$_{6,7}$=2.19)
    7 5.302 (1H, dd, J$_{7,8}$=9.90)
    8 5.483 (1H, ddd, J$_{8,9}$=2.93)
    9 4.251 (1H, dd, J$_{9,9'}$=12.45)
    9' 4.014 (1H, dd, J$_{9,9'}$=6.22)
OAc×5 2.151, 2.044, 2.025, 1.868 (15H, s)
COOCH$_3$ 3.822 (3H, s)
IR $v^{KBr}$ cm$^{-1}$ 3500(O—H), 1748(C=O position-20), 1663 (C=O position-3)
FAB (+) MS 866(M+H)$^-$, 806(M—COOCH$_3$)$^-$
MP: 145–148° C.

2) Deprotection of a protected derivative of sialylbetamethasone

87 (402 mg) was dissolved in methanol (4 ml), and to this solution was added 1M sodium methoxide (0.45 ml) at 0–5° C. The mixture was stirred at room temperature for 3 h. After the solvent of the reaction solution was evaporated in vacuo, water (2 ml) and 1M sodium methoxide (0.46 ml) were added to the residue, and the resulting mixture was stirred at room temperature for 30 min. The reaction solution was applied to to a gel filtration column of LH-20, and eluted with methanol. The solvent was distilled off fro mfractions containing product in vacuo to give pale yellow powder (329.4 mg). A portion of the yellow powder (269 mg) was purified by HPLC using a reversed phase partition column (acetonitrile-water) to give 89β [32.4 mg (yield 12.5%)] and 89α [134 mg (yield 51.7%)], respectively, both as white powder.

Furthermore, a remaining portion of the product (60 mg) was treated with activated carbon to give 90 [38.0 mg (yield 67.7%)] as yellowish white powder.

Compounds 89β, 89α and 90
Compounds 89β and 89α $C_{33}H_{46}FNO_{13}$ MW=683.723
Compound 90 $C_{33}H_{16}FNO_{13}Na$ MW=705.704
Compound 89β
$^1$H-NMR [500 MHz, $CD_3OD$, Ref=3.30 ppm ($CH_3OD$)]
  $3_{ax}$ 1.689 (1H, dd, $J_{3ax.4}$=11.36, $J_{3ax.3eq}$=12.82)
  $3_{eq}$ 2.432 (1H, dd, $J_{3eq.4}$=5.12)
  4 4.164 (1H, ddd, $J_{4,5}$=10.99)
  5 3.832 (1H, t, $J_{5,6}$=10.25)
  6 3.602 (1H, dd, $J_{6,7}$=11.36)
  9 3.745 (1H, dd, $J_{9,8}$=5.50, $J_{9,9'}$=9.53)
  9' 3.462 (1H, dd, $J_{9,9'}$=9.53)
  Ac 2.004 (3H, s)
FAB(−)MS 682(M—H)$^-$
Compound 89α
$^1$H-NMR [500 MHz, DMSO, Ref=2.50 ppm (DMSO)]
  $3_{ax}$ 1.530 (1H, d, $J_{3ax.3eq}$=12.46)
  $3_{eq}$ 2.561 (1H, dd, $J_{3eq.4}$=4.40)
FAB(−)MS 682 (M—H)$^-$
MP: 156–159° C.
Compound 90
FAB(−)MS 704 (M—H)$^-$
$^1$H-NMR [500 MHz, $CD_3OD$, Ref=3.30 ppm ($CH_3OD$)]
  1: 6.066 (1H, s)
  3ax: 1.711 (1H, t, J=12.09)
  3eq: 2.378 (1H, t, J=4.03)

EXAMPLE 12

Figure 12:
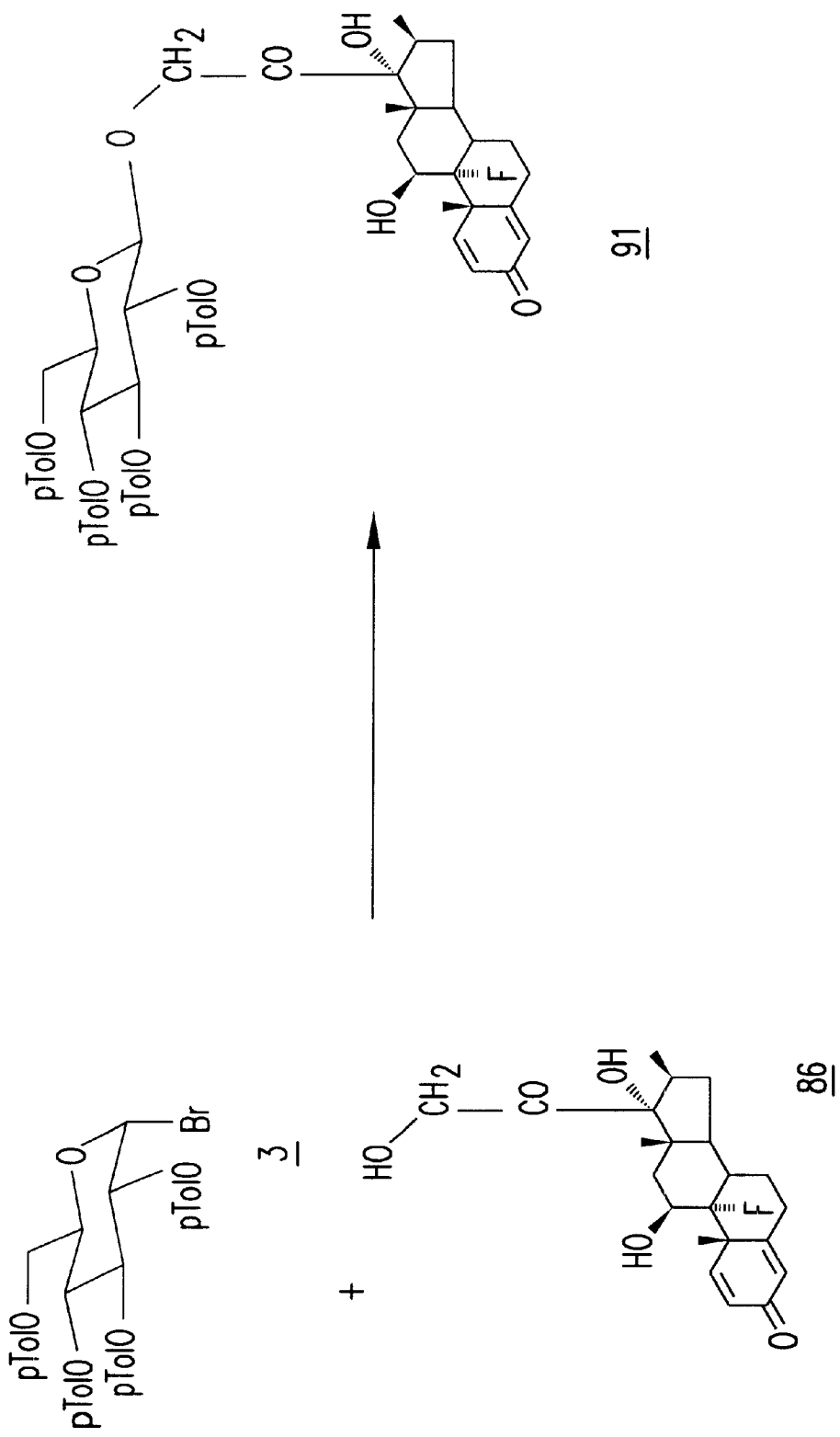
FIG. 12 is a flow-chart showing the synthesis route of per-Tol-protected derivative of glucosylbetamethasone.

Synthesis of glucosylbetamethasone (protected derivative: per-Tol) (FIG. 12)

3+86→91 (glucosylation)

Betamethasone (86) (3.69 g) was dissolved in tetrahydrofuran (200 ml), and to this solution were added molecular sieve 5A (4.90 g) and silver triflate (4.83 g). To this mixture was added, under an argon atmosphere and at 0–5° C., a solution of a glucose bromide (protected derivative: per-Tol) (3) (13.45 g) dissolved in tetrahydrofuran (70 ml). While the reaction temperature was raised slowly to room temperature, the mixture was stirred for 6 h. To this mixture was further added silver triflate (4.83 g), and the reuslting mixture was stirred overnight. The reaction solution was filtered, and the solvent was distilled off from the filtrate in vacuo. The residue was dissolved in chloroform, and the chloroform solution was washed saturated sodium chloride solution. After the chloroform solution was dried over anhydrous magnesium sulfate, the solvent was distilled off in vacuo. The residue thus obtained was purified by silica gel chromatography (toluene:ethyl acetate=3:1) to give white powder [2.87 g(yield 29.7%)]. This product was further purified by HPLC using a reversed phase partition column to give 91β [1.46 g (yield 15.1%)] and 91α [0.17 g (yield 1.8%)], respectively both as white powder.
Compound 91 [glucosylbetamethasone (protected derivative: per Tol)]

Molecular formula $C_{60}H_{63}FO_{14}$
MW 1027.148
Glucosylbetamethasone (per Tol) β-anomer (91β)
$^1$H-NMR [500 MHz, $CDCl_3$, Ref=0.000 ppm(TMS)]
  1: 5.012 (1H, d, $J_{1,2}$=8.06)
  2: 5.516 (1H, t, $J_{2,3}$=9.89)
  3: 5.872 (1H, t)
  4: 5.642 (1H, t)
  5: 4.097 (1H, t)
  ($CH_3C_5H_4CO$—)×4: 7.865, 7.830, 7.782, 7.716 (each 2H, d)
  ($CH_3C_6H_4CO$—)×4: 2.380, 2.347, 2.286 (12H, s)
IR ν$^{KBr}$ cm$^{-1}$ 3472(O—H), 1732(C=O position-20), 1665 (C=O position-3)
FAB(+)MS 1027(M+H)$^-$, 1009(M—OH)$^+$
MP: 154–157° C.
Glucosylbetamethasone (per Tol) α-anomer (91α)
$^1$H-NMR [500 MHz, $CDCl_3$, Ref=0.000 ppm(TMS)]
  1: 5.254 (1H, d, $J_{1,2}$=4.03)
  2: 5.205 (1H, dd, $J_{2,3}$=10.25)
  3: 6.120 (1H, t)
  4: 5.741 (1H, t)
  6: 4.926 (1H, dd, $J_{6,6'}$=12.46)
  6': 4.223 (1H, dd, $J_{6,6'}$=2.56)
  ($CH_3C_6H_4CO$—)×4: 7.946, 7.872, 7.835, 7.764 (each 2H, d)
  ($CH_3C_6H_4CO$—)×4: 2.419, 2.366, 2.334, 2.294 (each 3H, s)
IR ν$^{KBr}$ cm$^{-1}$ 3478(O—H), 1731(C=O position-20), 1666 (C=O position-3)
FAB(+)MS 1027(M+H)$^-$, 1009(M—OH)$^+$
MP: 159–162° C.

(II) Evaluation of Pharmacological Activity

Ointment to be tested was prepared usign white soft paraffin as the base and containing dexamethasone at 0.1% concentration.

1. Inhibitory Effects on Granuloma Growth (Paper Disk Method)

1) Experimental method

Groups of 5 male Sprague-Dawley rats each weighing 150–170 g were used. Under ether anesthesia, the dorsum of animals was closely clipped, and medianly incised. After each one pre-weighed paper disk (8-mm diameter, 1-mm thick, weighing about 30 mg; Toyo-Roshi filter paper) was inserted subcutaneously into both sides of the dorsal incision, the incision was sutured. In order to prevent bacterial infection, penicillin G potassium salt (2,000 units) per rat was intramascularly injected after the surgery. Base or ointment to be tested (50 mg each) was rubbed carefully into the skin over the paper disk inserted site, for 30 seconds once a day for the duration of 7 days. Rats were slipped plastic cangs on to prevent them from licking the drug applied sites. On the 8th day of the test, rats were sacrificed under ether anesthesia, and granulomas were carefully excised. Granulomas were dried at 40° C. for 24 h, and their dry weights were recorded.

2) Results

Inhibitory effects of dexamethasone derivatives on the weight increase of granuloma of experimental animals as compared with those of control animals are shown as per cent of inhibition ov er the control in Table 1. Figures wihth asterisks in the table indicate signfiicant difference. The same will be applied to the following other tables.

TABLE 1

Effects of dexamethasone derivatives on growth of granuloma

| Test compound | Weight of granuloma |
|---|---|
| Control | 0.0 ± 5.8 |
| White soft paraffin (base) | −0.6 ± 6.1 |
| Betamethasone valerate | −22.5 ± 5.7* |
| Dexamethasone | −42.2 ± 2.6** |
| 4α | −0.6 ± 5.1 |
| 4β | −7.9 ± 5.0 |
| 5β | −47.4 ± 2.9** |
| 10 | −38.3 ± 5.3** |
| 14α | 5.7 ± 1.9 |
| 14β | −8.7 ± 7.2 |
| 15α | −39.5 ± 1.8** |
| 15β | −41.0 ± 2.6** |
| 24α | −3.7 ± 4.5 |
| 25α | −18.0 ± 4.8* |
| 29 | −35.7 ± 5.6** |
| 34β | −21.3 ± 3.9* |
| 35β | −21.9 ± 4.2* |
| 44β | −16.5 ± 3.0* |
| 44' | 3.3 ± 4.7 |
| 45β | −28.1 ± 3.5** |
| 45' | −11.8 ± 10.1 |
| 54β | −35.1 ± 2.8** |
| 54' | −44.8 ± 2.4** |
| 55β | −37.4 ± 7.1** |
| 59β | −7.7 ± 6.8 |
| 64β | −32.5 ± 0.5** |
| 64' | −41.3 ± 2.3** |
| 65β | −33.0 ± 3.3** |
| 66 | −29.3 ± 6.3** |
| 69β | 0.7 ± 2.4 |
| 74β | 1.6 ± 16.2 |
| 75β | −10.0 ± 8.8 |
| 84α | −16.0 ± 2.9 |
| 84β | −7.3 ± 3.8 |
| 85α | −31.1 ± 2.2** |
| 85β | −7.8 ± 5.2 |
| 87 | 1.2 ± 6.1 |
| 89α | −22.1 ± 6.0* |
| 89β | −26.4 ± 2.2** |
| 90 | −13.1 ± 4.7 |
| Control | 0.0 ± 5.1 |
| White soft paraffin (base) | −0.7 ± 7.1 |
| Betamethasone valerate | −19.4 ± 4.8 |
| Dexamethasone | −55.4 ± 5.7 |
| 105β | −1.2 ± 5.7 |
| 107β | −6.3 ± 5.5 |
| 109β | −0.2 ± 3.7 |

Figures indicate the per cent of change of the controls on granuloma weights.

2. Croton Oil-induced Granuloma

1) Experimental method

Groups of 5 male Sprague-Dawley rats each weighing 160–180 g were used. Under ether anesthesia, the dorsum of animals was closely clipped, and air sac was formed by injecting air (20 ml) subcutaneously. Next day cotton seed oil containing 1% croton oil was injected into the air sac. Drugs to be tested were suspended in the cotton seed oil containing 1% croton oil, and administered. After 7 days, the blood was taken from the animal under ether anesthesia. Then, the granuloma pouch fluid (exudate) was collected, and the fluid volume was measured. The pouch wall formed around granuloma and thymus were also excised and weighed.

2) Results

Per cent of inhibition over the volume of pouch fluid, and wet weight of granuloma pouch as well as thymus of the control are shown in Tables 2–4.

TABLE 2

Effects of dexamethasone derivatives on croton oil-induced granuloma
Effects on pouch fluid (exudate) volume

| Test compound | 0.01 mg/rat | 0.1 mg/rat | 1.0 mg/rat |
|---|---|---|---|
| Betamethasone valerate | 21.3 ± 10.8 | 1.3 ± 6.3 | 23.9 ± 12.1 |
| 91β | 25.3 ± 5.3 | 18.4 ± 6.1 | 18.9 ± 8.8 |
| 100β | 20.8 ± 11.7 | 17.5 ± 5.9 | 69.4 ± 6.7 |
| 103β | 32.8 ± 9.6 | 24.8 ± 4.8 | 43.2 ± 6.9 |
| Betamethasone valerate | −6.4 ± 16.1 | 14.0 ± 6.5 | 41.0 ± 9.9 |
| Diflupredonate | 17.4 ± 13.5 | 65.3 ± 12.1 | 96.2 ± 1.2 |
| Diflurasone acetate | −20.9 ± 13.8 | −14.5 ± 11.6 | 14.3 ± 15.1 |
| Diflucortolone valerate | 27.3 ± 6.7 | 48.9 ± 2.9 | 90.8 ± 3.3 |
| 105β | −8.1 ± 9.4 | 24.8 ± 8.8 | 76.4 ± 4.3 |
| 107β | −28.5 ± 18.8 | −30.9 ± 20.9 | 28.8 ± 15.2 |
| 109β | −13.1 ± 16.7 | 14.6 ± 9.4 | 37.5 ± 11.9 |
| Betamethasone valerate | 14.3 ± 7.6 | 46.2 ± 5.8 | — |
| Betamethasone acetate propionate | 27.6 ± 8.1 | 43.6 ± 4.7 | — |
| Diflucortolone valerate | 48.3 ± 6.1 | 92.4 ± 2.1 | — |
| 109β | 26.6 ± 4.2 | 61.3 ± 2.9 | 90.8 ± 1.6 |
| 110β | 34.4 ± 8.9 | 79.6 ± 8.5 | 97.2 ± 0.5 |
| 112β | 36.1 ± 9.2 | 43.7 ± 2.5 | 93.1 ± 1.6 |
| 113β | 90.5 ± 6.6 | 97.1 ± 0.5 | 97.5 ± 0.7 |

Figures indicate the per cent of inhibition over the pouch fluid volume of the control.

TABLE 3

Effects of dexamethasone derivatives on croton oil-induced granuloma
Effects on gramuloma weight

| Test compound | 0.01 mg/rat | 0.1 mg/rat | 1.0 mg/rat |
|---|---|---|---|
| Betamethasone valerate | 25.0 ± 5.1 | 10.2 ± 5.2 | 18.7 ± 11.7 |
| 91β | 17.1 ± 6.7 | 6.9 ± 5.1 | 4.3 ± 8.2 |
| 100β | 11.0 ± 6.5 | 4.1 ± 11.3 | 60.5 ± 5.8 |
| 103β | 25.9 ± 8.6 | 15.0 ± 7.0 | 34.5 ± 6.4 |
| Betamethasone valerate | −7.0 ± 14.3 | 0.4 ± 9.4 | 23.6 ± 10.1 |
| Diflupredonate | −11.0 ± 23.1 | 35.0 ± 10.3 | 78.8 ± 5.0 |
| Diflurasone acetate | −13.1 ± 13.3 | 4.0 ± 10.5 | 11.7 ± 12.4 |
| Diflucortolone valerate | 12.8 ± 5.1 | 22.1 ± 3.6 | 66.0 ± 7.1 |
| 105β | −5.9 ± 10.9 | 22.1 ± 3.7 | 53.0 ± 6.2 |
| 107β | −21.2 ± 19.2 | −23.3 ± 21.4 | 28.1 ± 12.5 |
| 109β | −21.3 ± 13.5 | 6.0 ± 9.3 | 36.5 ± 10.2 |
| Betamethasone valerate | 8.1 ± 7.0 | 36.4 ± 4.4 | — |
| Betamethasone acetate propionate | 21.2 ± 6.4 | 26.0 ± 6.9 | — |
| Diflucortolone valerate | 25.1 ± 5.0 | 66.4 ± 3.3 | — |
| 109β | 13.5 ± 4.4 | 44.7 ± 3.6 | 58.0 ± 1.9 |
| 110β | 16.8 ± 7.1 | 58.7 ± 1.4 | 70.3 ± 1.9 |
| 112β | 15.9 ± 6.9 | 27.1 ± 2.4 | 61.3 ± 2.2 |
| 113β | 47.4 ± 11.0 | 60.8 ± 9.3 | 90.5 ± 0.6 |

Figures indicate the per cent of inhibition over the granuloma weight of the control.

TABLE 4

Effects of dexamethasone derivatives on croton oil induced granuloma Effects on thymus weight

| Test compound | 0.01 mg/rat | 0.1 mg/rat | 1.0 mg/rat |
|---|---|---|---|
| Betamethasone valerate | −0.5 ± 5.8 | 7.3 ± 4.1 | 37.0 ± 3.0 |
| 91β | 2.1 ± 3.7 | 7.4 ± 2.8 | 4.7 ± 9.7 |
| 100β | 6.3 ± 4.8 | 0.1 ± 4.5 | 1.8 ± 6.2 |
| 103β | 21.5 ± 5.7 | 11.2 ± 3.1 | 4.3 ± 3.9 |
| Betamethasone valerate | 1.7 ± 6.3 | 13.5 ± 5.8 | 58.9 ± 3.3 |
| Diflupredonate | 14.7 ± 10.4 | 71.2 ± 2.9 | 71.8 ± 3.2 |
| Diflurasone acetate | 3.9 ± 9.0 | 32.4 ± 4.5 | 55.5 ± 7.7 |
| Diflucortolone valerate | 31.6 ± 6.4 | 70.6 ± 3.4 | 77.3 ± 3.8 |
| 105β | −1.9 ± 7.8 | −2.0 ± 8.6 | −5.0 ± 5.2 |
| 107β | −4.2 ± 5.5 | 3.9 ± 5.9 | −4.9 ± 7.2 |
| 109β | −2.7 ± 7.5 | −6.0 ± 9.6 | 3.4 ± 8.6 |
| Betamethasone valerate | 22.3 ± 1.6 | 50.1 ± 6.0 | — |
| Betamethasone acetate propionate | 16.7 ± 14.1 | 56.3 ± 3.6 | — |
| Diflucortolone valerate | 30.1 ± 2.5 | 81.4 ± 2.4 | — |
| 109β | 10.9 ± 8.6 | 17.7 ± 4.6 | 15.9 ± 3.3 |
| 110β | 20.9 ± 6.3 | 22.9 ± 8.4 | 19.5 ± 8.3 |
| 112β | 13.7 ± 7.3 | 20.5 ± 5.7 | 15.7 ± 9.2 |
| 113β | 78.9 ± 3.2 | 95.8 ± 0.8 | 94.8 ± 0.6 |

Figures indicate the per cent of inhibition over the control thymus weight.

Results shown in Tables 2–4 confirmed that the compounds of the present invention have inhibitory effects on the growth of granuloma in rats.

That is, results in Tables 2–4 indicate that the compounds of the present invention have the following pharmacological properties.

1) Effects on thymus weight are significantly reduced with the glucosyl derivatives as compared with the non-glucosylated original compounds or the conventional anti-inflammatory drugs.

2) Reducing effects on the thymus atrophy were clearly observed with the glucosylated derivatives protected with toluoyl, benzoyl and chlorobenzoyl groups, but not with those protected with acetyl group.

3) Suppression effects of glucosyl derivatives on granuloma weights and pouch exudate volumes were lower than those of the non-glycosylated compounds, but more highly effective than those of the conventional drugs.

3. Inhibitory Effects on Croton oil-indiced Ear Lobe Edema

12) Experimental method

Groups of 10 male ddY mice each weighing about 25 g were used. Ointment to be tested (20 mg) was rubbed in the right-side ear lobe, and, 30 min later, a drop of 4 % croton oil dissolved in either was applied to it. Thirty minute after that treatment, mice were sacrificed. Ear lobes on both sides were punched out in the size of 5-mm diameter, and weighed. Results were expressed by calculating the per cent of weight change of the right edema ear as compared with that of the untreated left ear, and compared with that of the control.

2) Results

Per cent of inhibition of edema formation in experimental mice as compared with those of controls are shown in Tables 5 and 6.

TABLE 5

Effects of dexamethasone derivatives on croton oil-induced ear edema

| Test compound | Percent of inhibition of ear edema (%) |
|---|---|
| Control | 0.0 ± 5.3 |
| White soft paraffin (base) | 1.6 ± 4.9 |
| Betamethasone valerate | 29.1 ± 5.9** |
| Dexamethasone | 32.9 ± 3.5** |
| 4α | 24.1 ± 4.9** |
| 4β | 23.5 ± 4.1** |
| 5β | 19.6 ± 3.3** |
| 10 | 27.5 ± 5.9** |
| 14α | 9.0 ± 4.9 |
| 14β | 11.9 ± 3.5 |
| 15α | 27.5 ± 3.6** |
| 15β | 34.0 ± 4.1** |
| 24α | 6.8 ± 2.9 |
| 25α | 24.9 ± 5.5** |
| 29 | 22.1 ± 4.7** |
| 34β | 9.1 ± 5.0 |
| 35β | 29.0 ± 3.0** |
| 44' | 7.9 ± 7.2 |
| 44β | 9.2 ± 4.5 |
| 45' | 21.0 ± 6.4* |
| 45β | 24.6 ± 6.3** |
| 54' | 25.7 ± 4.1** |
| 54β | 13.2 ± 5.1 |
| 55β | 21.6 ± 5.9* |
| 59β | 13.6 ± 4.0 |
| 64' | 18.4 ± 4.5* |
| 64β | 17.7 ± 2.8** |
| 65β | 26.5 ± 3.2** |
| 66 | 18.3 ± 3.6* |
| 69β | 17.8 ± 3.8* |
| 75β | 22.0 ± 4.7** |
| 74β | 14.1 ± 4.5 |
| 84α | 13.6 ± 3.6* |
| 84β | 11.0 ± 4.8 |
| 85α | 26.5 ± 4.4** |
| 85β | 19.2 ± 3.7** |
| 87 | 8.8 ± 5.0 |
| 89α | 22.5 ± 5.2** |
| 89β | 22.2 ± 5.3** |
| 90 | 15.6 ± 6.6 |

Figures indicate the per cent of inhibition over the edema formation in the control.

TABLE 6

Effects of dexamethasone derivatives on croton oil-induced ear edema

| Test compound | Percent of inhibition of ear edema (%) |
|---|---|
| Control | 0.0 ± 7.3 |
| White soft paraffin (base) | 7.4 ± 6.3 |
| Betamethasone valerate | 24.9 ± 3.5 |
| Dexamethasone | 32.9 ± 3.5 |
| 91β | 32.9 ± 7.8 |
| 94β | 35.1 ± 4.1 |
| 97β | 36.6 ± 5.1 |
| 100β | 40.5 ± 4.7 |
| 105β | 42.0 ± 2.9 |
| 107β | 41.4 ± 6.1 |
| 109β | 38.6 ± 9.2 |
| 114β | 49.8 ± 9.7 |
| 115β | 23.3 ± 2.1 |
| 117β | 24.2 ± 6.3 |

Figures indicate the per cent of inhibition to the edema formation in controls.

Results in Tables 5 and 6 confirmed that the compounds of the present invention have inhibitory effects on the croton oil-induced ear edema in mice.

4. Effects of 7-day Ointment Rubbing on Organ Weights

1) Experimental method

Groups of 5 male Sprague-Dawley rats each weighing 150–170 g were used. Under ether anesthesia, the dorsum of animals were closely clipped, and test drug (100 mg) was carefully rubbed in the clipped dorsal area for 30 seconds. Rats were slipped on plastic cang to prevent them from licking the drug-applied area. After the drug rubbing once daily for 7 days, on the 8th day rats were anesthetized with ether. Blood samples were collected, and thymus, spleen, and adrenal were excised and measured their wet weights. Furthermore, leukocyte number was counted with the blood samples collected. Results were expressed as the per cent of change of body weight on the 8th day as compared with that on the 1st day of rubbing. Similarly, the per cent of change in weights of thymus, spleen and adrenal on the 8th day as compared with that of the control animlas were shown.

2) Results

Effects of 7-day ointment rubbing on weights of body, thymus, spleen and adrenal, and leukocyte counts are shown in Tables 7 and 8.

TABLE 7

Effects of 7-day rubbing dexamethasone derivatives on body weight, organ weight and leukocyte count

| Test | Body weight | Adrenal weight | Thymus weight | Spleen weight | Leukocyte count |
|---|---|---|---|---|---|
| Normal animal | 23.2 ± 1.7 | 0.0 ± 5.6 | 0.0 ± 2.2 | 0.0 ± 3.4 | 0.0 ± 6.3 |
| White soft paraffin (base) | 22.2 ± 0.6 | −1.8 ± 4.5 | −6.0 ± 7.5 | 13.2 ± 5.5 | −20.3 ± 11.9 |
| Betamethasone valerate | 23.8 ± 2.7 | −12.8 ± 2.2** | −23.3 ± 3.4** | −10.9 ± 5.8 | 1.6 ± 3.0 |
| Dexamethasone | −8.7 ± 1.4** | −48.5 ± 1.4** | −91.5 ± 0.6** | −70.0 ± 3.5** | −46.6 ± 12.1** |
| 4α | 27.2 ± 0.9* | −13.8 ± 2.3* | 3.1 ± 8.9 | 9.9 ± 6.0 | 3.2 ± 4.5 |
| 4β | 21.4 ± 1.8** | −15.3 ± 3.0* | 0.6 ± 5.9 | 1.9 ± 4.3 | 19.0 ± 4.7 |
| 5β | 0.7 ± 1.4** | −49.6 ± 3.2** | −85.7 ± 2.6** | −56.0 ± 1.6** | −46.6 ± 8.2** |
| 10 | −2.7 ± 2.6** | −53.8 ± 3.5** | −85.5 ± 3.8** | −68.5 ± 2.8** | −54.9 ± 4.3** |
| 14α | 25.2 ± 0.8** | −11.0 ± 5.7 | −10.7 ± 8.5 | −5.5 ± 7.1 | −21.8 ± 10.5 |
| 14β | 25.3 ± 1.6* | −9.5 ± 4.8 | −12.0 ± 2.2 | 0.5 ± 5.1 | −0.6 ± 6.1 |
| 15α | 8.3 ± 1.0** | −48.3 ± 2.9** | −82.2 ± 3.3** | −35.7 ± 2.3** | −22.6 ± 7.4* |
| 15β | 4.6 ± 0.9** | −47.1 ± 1.9** | −86.0 ± 1.4** | −43.2 ± 2.1** | −37.0 ± 6.9** |
| 24α | 22.7 ± 1.9** | −7.8 ± 3.8 | −15.1 ± 11.4 | −2.0 ± 7.3 | −4.3 ± 9.4 |
| 25α | 16.1 ± 1.7* | −24.4 ± 3.4** | −32.6 ± 7.4** | −18.2 ± 2.2** | −0.7 ± 9.0 |
| 29 | −1.1 ± 2.0** | −46.0 ± 2.4** | −88.8 ± 2.2** | −59.5 ± 1.6** | −55.5 ± 4.9** |
| 34β | 11.9 ± 1.0** | −37.4 ± 3.9** | −66.4 ± 1.1** | −37.2 ± 1.8** | −43.7 ± 6.7** |
| 35β | 10.5 ± 2.8** | −29.9 ± 5.0** | −61.9 ± 3.1** | −28.7 ± 5.5** | −36.4 ± 4.7** |
| 44' | 22.7 ± 1.1** | −19.6 ± 5.5* | −17.9 ± 3.3* | −11.5 ± 4.8 | −23.0 ± 5.1 |
| 44β | 12.4 ± 2.7** | −33.0 ± 4.6** | −57.2 ± 9.5** | −35.4 ± 4.9** | −20.7 ± 7.0 |
| 45' | 22.9 ± 1.7 | −15.4 ± 3.2* | −6.8 ± 4.0 | −0.1 ± 5.1 | 6.6 ± 15.1 |
| 45β | 13.3 ± 3.1* | −37.6 ± 2.8** | −55.1 ± 7.9** | −24.2 ± 5.3** | −22.3 ± 4.5* |
| 54' | −0.8 ± 1.6** | −50.1 ± 3.0** | −87.6 ± 3.0** | −63.2 ± 3.1** | −57.2 ± 6.0** |
| 54β | 13.6 ± 1.6** | −41.7 ± 5.1** | −64.6 ± 6.3** | −41.3 ± 1.7** | −35.1 ± 4.8* |
| 55β | 12.4 ± 2.7* | −42.5 ± 3.7** | −69.9 ± 6.5** | −26.8 ± 11.0* | −43.3 ± 4.4** |
| 59β | 24.4 ± 1.2** | −17.4 ± 3.9* | −17.5 ± 10.3 | 0.0 ± 6.6 | 11.8 ± 5.7 |
| 64' | −0.9 ± 2.0** | −50.1 ± 2.3** | −89.6 ± 2.0** | −61.9 ± 2.6** | −57.2 ± 2.9** |
| 64β | 7.8 ± 1.5** | −46.0 ± 4.1** | −86.5 ± 1.4** | −47.6 ± 2.0** | −48.3 ± 4.8** |
| 65β | 13.9 ± 2.1** | −32.0 ± 2.9** | −47.1 ± 9.9** | −21.3 ± 4.0** | −20.3 ± 19.7 |
| 66 | 14.3 ± 1.6** | −28.0 ± 3.0** | −39.0 ± 5.2** | −19.4 ± 2.2** | −25.9 ± 13.8 |
| 69β | 26.3 ± 2.0 | −3.9 ± 3.9 | −16.5 ± 8.6 | −4.4 ± 4.7 | 6.9 ± 9.3 |
| 74β | 19.4 ± 2.1** | −24.6 ± 3.7** | −26.3 ± 5.6* | −9.1 ± 4.6 | 6.6 ± 8.4 |
| 75β | 22.5 ± 2.5 | −48.9 ± 10.6** | −21.3 ± 8.9** | 3.5 ± 4.2 | 19.3 ± 9.5 |
| 84α | 24.8 ± 1.7* | −19.7 ± 3.5** | −16.4 ± 6.2 | −15.2 ± 3.6* | −5.5 ± 13.5 |
| 84β | 26.6 ± 3.1 | −17.6 ± 2.1** | −13.5 ± 4.9 | −5.0 ± 11.1 | 2.3 ± 13.3 |
| 85α | 12.9 ± 2.7* | −40.9 ± 2.0** | −58.2 ± 6.7** | −27.8 ± 3.5** | −25.2 ± 3.3** |
| 85β | 14.1 ± 2.3* | −33.4 ± 5.2** | −53.1 ± 7.5** | −16.1 ± 8.9 | −32.5 ± 9.4* |
| 87 | 23.5 ± 1.5** | −12.1 ± 3.5* | −10.8 ± 5.8 | −1.3 ± 4.6 | −10.3 ± 12.5 |
| 89α | 19.6 ± 1.5 | −22.7 ± 1.8** | −18.5 ± 6.8* | −7.2 ± 2.9 | 18.7 ± 8.7 |
| 89β | 16.7 ± 1.8* | −21.7 ± 3.1** | −33.1 ± 8.8** | −13.6 ± 2.7* | −6.6 ± 6.8 |
| 90 | 21.7 ± 1.6 | −22.9 ± 3.7** | −9.2 ± 6.3 | 0.1 ± 4.4 | 12.8 ± 8.8 |

TABLE 8

Effects of 7-day rubbing of dexamethasone derivatives on body weight, organ weight and leukocyte count

| Test compound | Body weight | Adrenal weight | Thymus weight | Spleen weight | Leukocyte count |
|---|---|---|---|---|---|
| Normal animal | 30.5 ± 1.3 | 0.0 ± 2.4 | 0.0 ± 4.1 | 0.0 ± 5.4 | 0.0 ± 8.6 |
| White soft paraffin (base) | 28.2 ± 0.6 | −1.8 ± 4.5 | −6.0 ± 7.5 | 13.1 ± 5.5 | −20.3 ± 11.9 |
| Betamethasone valerate | 18.1 ± 1.6 | −26.9 ± 5.5 | −57.2 ± 5.1 | −28.8 ± 3.7 | −44.7 ± 3.8 |
| Dexamethasone | −8.8 ± 3.4 | −49.2 ± 3.7 | −91.9 ± 0.9 | −71.6 ± 2.1 | −61.1 ± 3.3 |
| 105β | 22.4 ± 1.0 | 0.7 ± 4.5 | 0.6 ± 4.4 | 6.7 ± 2.6 | −10.6 ± 6.2 |
| 107β | 27.6 ± 2.2 | −5.7 ± 2.6 | 2.8 ± 6.7 | 8.8 ± 3.6 | −20.3 ± 14.4 |
| 109β | 27.6 ± 3.2 | −0.8 ± 1.8 | 14.1 ± 5.9 | −0.9 ± 5.7 | −29.2 ± 9.9 |

Results shown in Tables 7 and 8 confirmed that the compounds of the present invention are less toxic and pharmacologically more safe than dexamethasone.

As aforementioned, a series of steroid comounds of the present invention have the pharmacological effects shown in Tables 2–8, respectively. Among them, particularly, glycosyl steroid derivatives with Tol-protecting group including gulcosyl dexamethasone protected with Tol group and β-galacturonyldexamethasone protected with Tol group not only have suppressing effects on granuloma growth and croton oil-induced ear edema, but also they are less toxic and highly more safe.

EXAMPLE 13

Figure 13:
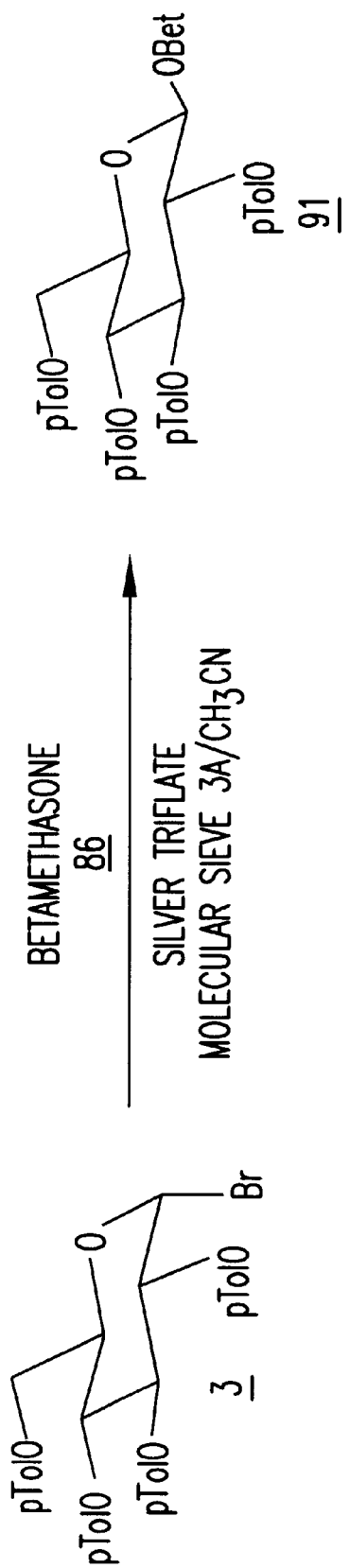
FIG. 13 is a flow-chart showing the synthesis route of glucosylbetamethasone (p-toluoyl derivative).

Synthesis of glucosylbetamethasone (p-toluoyl derivative) (modified method) (FIG. 13)

1) Synthesis of glucosylbetamethasone (p-toluoyl derivative) (91) 3+86→91

Betamethasone (86) (1.28 g) was dissolved in acetonitrile (85 ml), and to this solution were added molecular sieve 3A (1.80 g) and silver triflate (1.62 g). To this mixture was added, under an argon atmospehre and at 0–5° C., a solution of a glucose bromide (3) (4.65 g) dissolved in acetonitrile (45 ml). While the reaction temperature was slowly raised to room temperature, the resuling mixture was stirred for 6 h. To this mixture was further added silver triflate (1.62 g), and the resulting mixture was stirred at room temperature for 19 h. The reaction solution was filtered, and the solvent was distilled off from the filtrate in vacuo. The residue was dissolved in chloroform, and the solution was washed with saturated sodium chloride solution. After the chloroform solution was dried over anhydrous magnesium sulfate, the solvent was evaporated in vacuo. The residue thus obtained was purified by silica gel column chromatography (hexane:ethyl acetate=5:4) to give white powder (2.62 g). This powder was further purified by HPLC using a reversed phase partition column (acetonitrile-water) to give β-anomer (91β) as white powder [2.05 g (yield 61.1%)].

EXAMPLE 14

Figure 14:
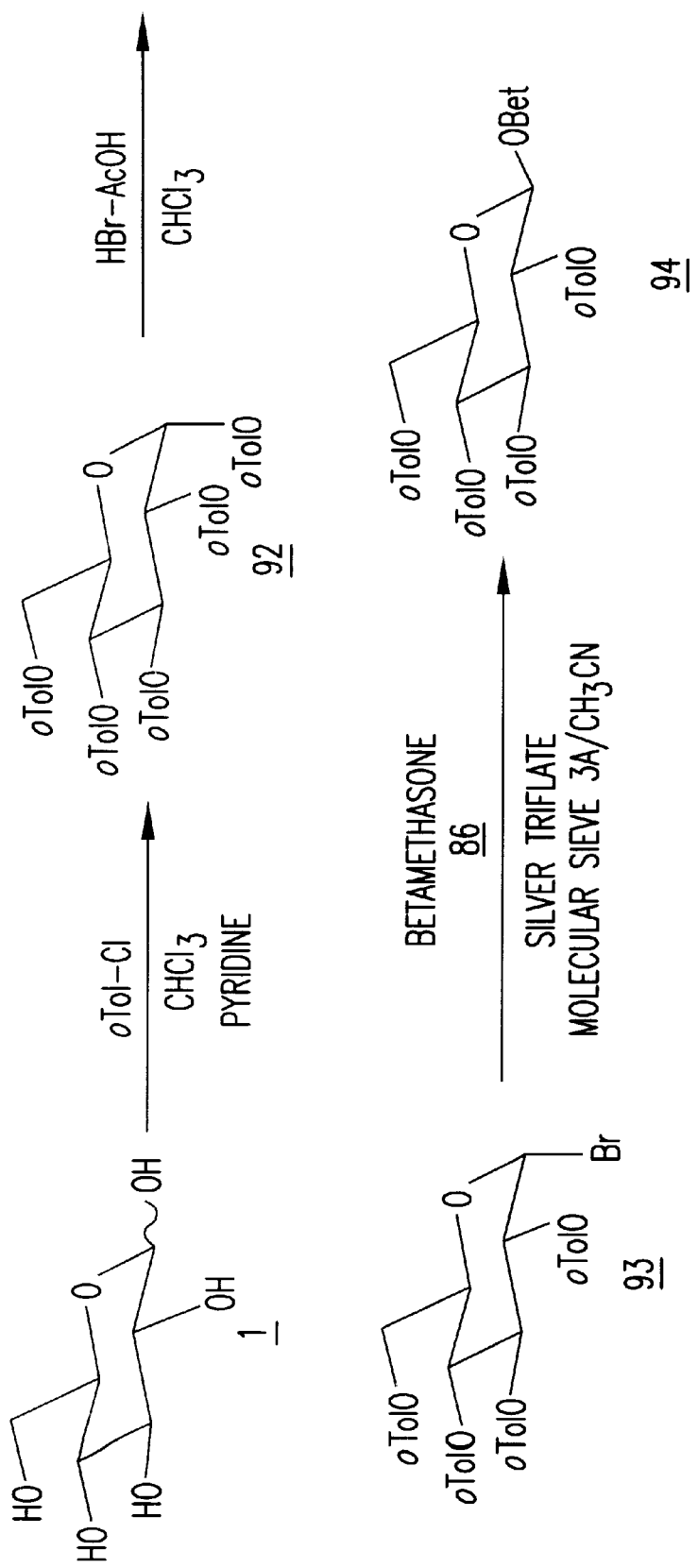
FIG. 14 is a flow-chart showing the synthesis route of glucosylbetamethasone (o-toluoyl derivative).

Synthesis of glucosylbetamethasone (o-toluoyl derivative) (FIG. 14)

1) Toluoylation of glucose 1→92

D-(+)-Glucose (1) (1.21 g) was dissolved in chloroform (24ml), and to this solution were added p-toluoyl chloride (8.85 ml) and pyridine (5.49 ml) drop-wise at 0–5° C. While the reaction temperature was slowly raised to room temperature, the reaction mixture was stirred for 4 h. The reaction solution was poured into ice-water, and extracted with chloroform. The organic layer was washed successively with saturated solutiosn of copper sulfate, sodium bicarbonate, and sodium chloride. After the solution was dried over anhydrous magnesium sulfate, the solvent was evaporated from the solution in vacuo. The residue thus obtained was purified by silica gel column chromatography (toluene:ethyl acetate=6:1) to give 92 as white powder [5.16 g (quant.)].

Compound 92

$C_{46}H_{42}O_{11}$ MW=770.881

$^1$H-NMR [500 MHz, $CDCl_3$, Ref=0.000 ppm (TMS)]

δ; 2.578, 2.561, 2.492, 2.439, 2.352 (15H, 5s, $CH_3C_6H_4CO$—)

6.877 (1H, d, J=3.66, H-1)

8.061, 7.961, 7.887, 7.831, 7.790 (5H, 5d, J=8.06, $CH_3C_6H_4CO$—)

2) Bromination of glucose (o-toluoyl derivative) 92→93

92 (2.84 g) was dissolved in chloroform (13 ml), and to this solution was added hydrogen bromide-acetic acid solution (7.7 ml) at 0–5° C. While the reaction temeprature was slowly raised to room temperature, the mixture was stirred for 3 h. After the unreacted bromine was removed with an argon stream, the solvent was distilled off in vacuo. The residue was dissolved in chloroform, and the solution was washed cold saturated sodium bicarbonate solution. After the chloroform solution was dried over anhydrous magnesium sulfate, the solvent was evaporated in vacuo to give 93 as pale yellow powder [2.44 g (yield 92.6%)].

Compound 93

$C_{38}H_{35}O_9Br$ MW=715.593

$^1$H-NMR [500 MHz, $CDCl_3$, Ref=0.000 ppm(TMS)]

δ; 2.611, 2.553, 2.451, 2.340 (12H, 4s, $CH_3C_6H_4CO$—)

6.890 (1H, d, J=4.03, H-1)

8.002, 7.974, 7.912, 7.734, (4H, 4d, J=8.06, $CH_3C_6H_4CO$—)

3) Synthesis of glucosylbetamethasone (o-toluoyl derivative) 93+86→94

Betamethasone (86) (350 mg) was dissolved in acetonitrile (23ml), and to this solution were added molecular sieve 3A (460 mg) and silver triflate (437 mg). To this mixture was added, under an argon atmosphere and at 0–5° C., a bromide of glucose (o-toluoyl derivative) (93) (1.22 g) dissolved in acetonitrile (12ml). While the reaction temperature was slowly raised to room temperature, the mixture was stirred for 6 h. To this mixture was further added silver triflate (437 mg), and the resulting mixture was stirred at room temperature for 17 h. The reaction solution was filtered, and the solvent was distilled off from the filtrate in vacuo. The residue was dissolved in chloroform, and washed with saturated sodium chloride solution. After the chloroform solution was dried over anhydrous magnesium sulfate, the solvent was evaporated in vacuo. The residue thus obtained was pruified by silica gel column chromatography (hexane:ethyl acetate=5:4) to give white powder (723.8 mg). This powder was further purified by HPLC using a reversed phase partition column chromatography (acetonitrile-water) to give 94β as white powder [450.4 mg (yield 49.2%)].
Compound 94β
$C_{60}H_{63}O_{14}F$ MW=1027.15
$^1$H-NMR [500 MHz, CDCl$_3$, Ref=0.000 ppm(TMS)]
δ; 2.574, 2.482, 2.436, 2.277 (12H, 4s, CH$_3$C$_6$H$_4$CO—)

4.119–4.081 (1H, m, H-5)

4.578 (2H, d, J=4.39, H-6, 6')

5.043 (1H, d, J=8.06, H-1)

5.542 (1H, dd, J=9.53, H-2)

5.642 (1H, t, H-4)

5.898 (1H, t, H-3)

6.113(1, s, Bet-4)

6.319 (1H, d, Bet-1)

7.965, 7.840, 7.755 (4H, 3d, J=6.96, CH$_3$C$_6$H$_4$CO—)
FAB(+)MS calcd. 1026.42; 1049(M+Na)$^-$
MP: 124–127° C.
IR $v_{max}^{KBr}$ cm$^{-1}$ 1734 (C=O position-20), 1665(C=O position-3)

EXAMPLE 15

Figure 15:
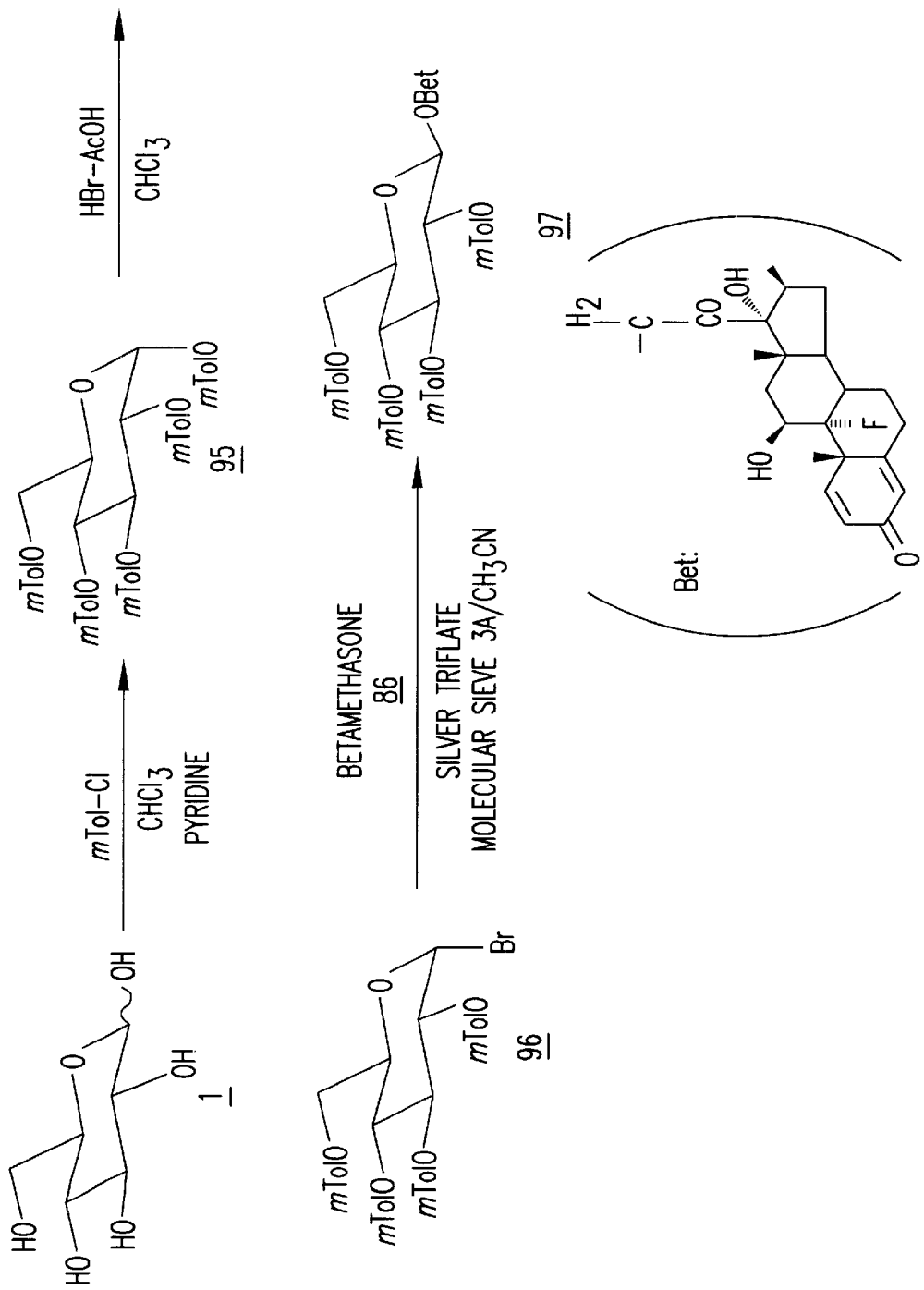
FIG. 15 is a flow-chart showing the synthesis route of glucosylbetamethasone (m-toluoyl derivative).

Synthesis of glucosylbetamethasone (m-toluoyl derivative) (FIG. 15)

1) m-Toluoylation of glucose 1→95

D-(+)-Glucose (1) (1.26 g) was dissolved in chloroform (24ml), and to this solution were added m-toluoyl chloride (9.20 ml) and pyridine (5.65 ml) at 0–5° C. While the reaction temperature was slowly raised to room temperature, the mixture was stirred for 3 h. The reaction solutin was poured into ice-water, and extracted with chloroform. The organic layer was washed successively with saturated solutions of copper sulfate, sodium bicarbonate, and sodium chloride. After the chloroform solution was dried over anhydrous magnesium sulfate, the solvent was evaporated in vacuo. The residue thus obtained was purified by silica gel column chromatography (hexane:ethyl acetate=5:1) to give 95 as white powder [5.49 g (quant.)].
Compound 95
$C_{46}H_{42}O_{11}$ MW=770.881
$^1$H-NMR [500 MHz, CDCl$_3$, Ref=0.000 ppm(TMS)]
δ; 2.463, 2.372, 2.328, 2.293, 2.248 (15H, 5s, CH$_3$C$_6$H$_4$CO—)

6.834 (1H, d, J=4.03, H-1)

2) Bromination of glucose (m-toluoyl derivative) (97) 95→96

(95) (2.64 mg) was dissolved in chloroform (12ml), and to this solution was added hydrogen bromide-acetic acid solution (5.2 ml) at 0–5° C. While the reaction temperature was slowly raised to room temperature, the mixture was stirred for 5 h. After the unreacted bromine was removed with an argon stream, the solvent was distilled off in vacuo. The residual material was dissolved in chloroform, and washed with cold saturated sodium bicarbonate solution. After the chloroform solution was dried over anhydrous magnesium sulfate, the solvent was evaporated in vacuo to give 96 as white powder [2.27 g (yield 92.5%)].
Compound 96
$C_{38}H_{35}O_9Br$ MW=715.593
$^1$H-NMR [500 MHz, CDCl$_3$, Ref=0.000 ppm(TMS)]
δ; 2.401, 2.353, 2.338, 2.290(12H, 4s, CH$_3$C$_6$H$_4$CO—)

6.874 (1H, d, J=4.03, H-1)

7.865, 7.799, 7.755, 7.684 (8H, 4d, J=7.70, CH$_3$C$_6$H$_4$CO—)

3) Synthesis of glucosylbetamethasone (m-toluoyl derivative) (97) 96+86→97

Betamethasone (86) (334 mg) was dissolved in acetonitrile (23 ml), and to this solution were added molecular sieve 3A (460 mg) and silver triflate (437 mg). To this mixture was added, under an argon atmosphere and at 0–5° C., a bromide of glucose (m-toluoyl derivative) (96) (1.22 mg) dissolved in acetonitrile (12 ml). While the reaction temperature was slowly raised to room temperature, the mixture was stirred for 3 h. To this mixture was further added silver triflate (437 mg), and the resulting mixture was stirred at room temperature overnight. The reaction solution was filtered, and the solvent was distilled off from the mother liquor in vacuo. The residual material was dissolved in chloroform, and the solution was washed with saturated sodium chloride solution. After the chloroform solution was dried over anhydrous magnesium sulfate, the solvent was evaporated in vacuo. The residue thus obtained was purified by silica gel column chromatography (hexane:ethyl acetate=5:4) to give white powder (819 mg). A portion of this product (300 mg) was further purified by HPLC using a reversed phase partition column chromatography (acetonitrile-water) to give β-anomer (97β) as white powder [212.9 mg (yield 66.5%)].
Compound 97β
$C_{60}H_{63}O_{14}F$ MW=1027.15
$^1$H-NMR [500 MHz, CDCl$_3$, Ref=0.000 ppm(TMS)]
δ; 2.338, 2.317, 2.294, 2.272(12H, 4s, CH$_3$C$_6$H$_4$CO—)

4.133–4.096(1H, m, H-5)

5.035(1H, d, J=8.06, H-1)

5.541(1H, dd, J=9.53, H-2)

5.656(1H, t, H-4)

5.833(1H, t, H-3)

6.135(1H, s, Bet-4)

6.344(1H, d, J=9.89, Bet-1)

7.786, 7.738, 7.705, 7.642(4H, 3d, J=7.69, CH$_3$C$_6$H$_4$CO—)
FAB(+)MS calcd. 1026.42;1049(M+Na)
MP:125–128° C.
IR $v_{max}^{KBr}$cm$^{-1}$ 1735(C=O position–20), 1665(C=O position–3)

EXAMPLE 16

Figure 16:
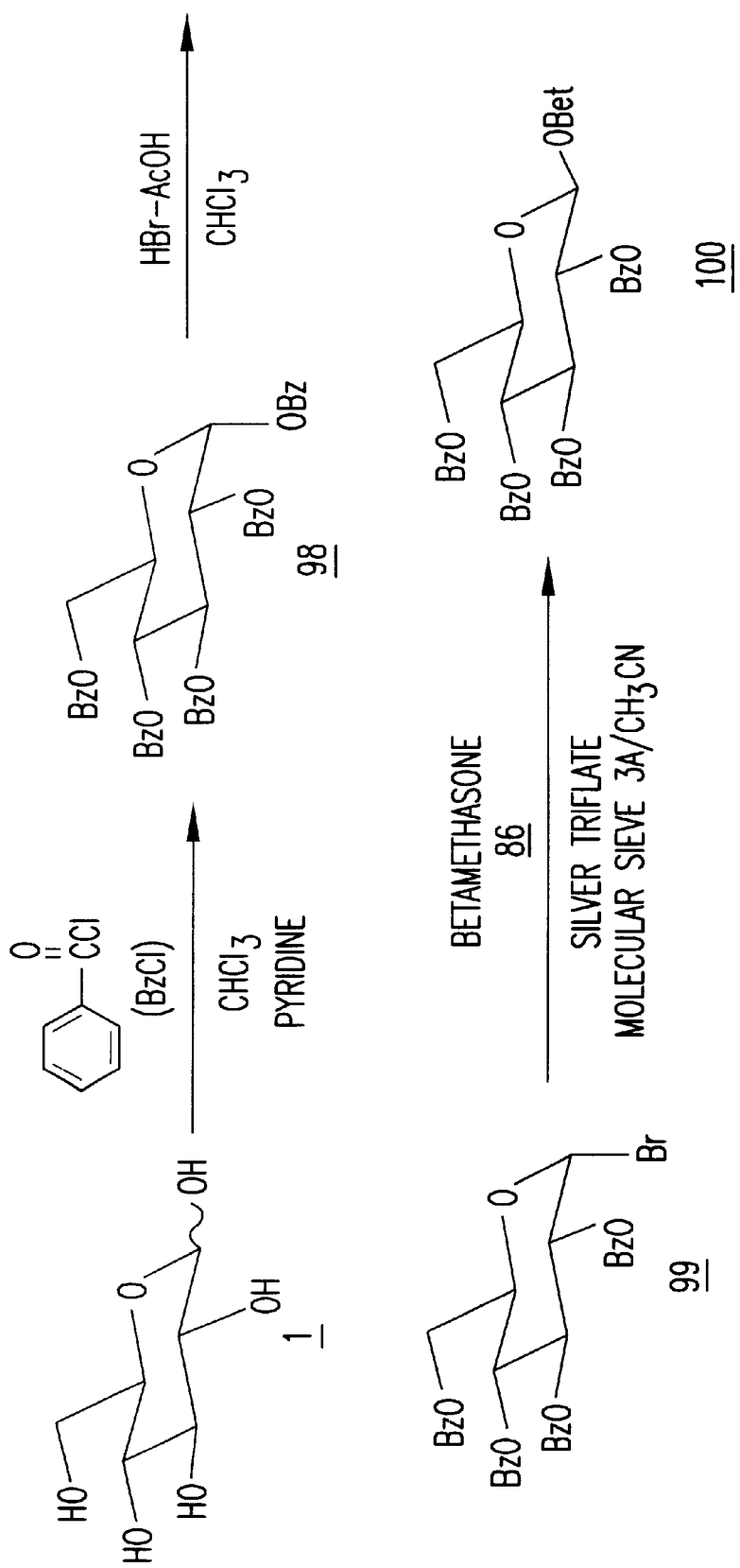
FIG. 16 is a flow-chart showing the synthesis route of glucosylbetamethasone (benzoyl derivative).

Synthesis of glucosylbetamethasone (benzoyl derivative) (FIG. 16)

1) Benzoylation of glucose 1→98

D-(+)-Glucose (1) (1.30 g) was dissolved in chloroform (24 ml), and to this solution were added benzoyl chloride (8.3 ml) and pyridine (5.8 ml) drop-wise at 0–5° C. While the reaction temperature was slowly raised to room temperature, this mixture was stirred for 4 h. The reaction solution was poured into ice-water, and extracted with chloroform. The organic layer was washed successively with saturated solutions of copper sulfate, sodium bicarbonate, and sodium chloride. After the chloroform solution was dried over anhydrous magnesium sulfate, the solvent was evaporated in vacuo. The residue thus obtained was purified by silica gel column chromatography (hexane:ethyl acetate= 3:1) to give 98 as white powder [7.26 g (theoretical)].
Compound 98
$C_{41}H_{32}O_{11}$ MW=700.693
$^1$H-NMR [500 MHz, CDCl$_3$, Ref=0.000 ppm(TMS)]
δ;5.683(1H, dd, J=10.26, H-2)

5.859(1H, t, H-4)

6.319(1H, t, H-3)
6.853(1H, d, J=4.03, H-1)
8.167, 8.026, 7.946, 7.874(8H, 4d, J=8.43, C$_6$H$_5$CO—)

2) Bromination of glucose (benzoyl derivative) 98→99

98(3.89 g) was dissolved in chloroform (19 ml), and to this solution was added hydrogen bromide-acetic acid solution (8.5 ml) at 0–5° C. While the reaction temperature was slowly raised to room temperature, the mixture was stirred for 4 h. After the unreacted bromine was removed with an argon stream, the solvent was evaporated from the reaction mixture in vacuo. The residue was dissolved in chloroform, and washed with cold saturated sodium bicarbonate solution. After the solution was dried over anhydrous magnesium sulfate, the solvent was distilled off in vacuo to give 99 as pale yellow powder [2.80 g (yield 76.4%)].

Compound 99
C$_{34}$H$_{27}$O$_9$Br MW=659.485
$^1$H-NMR [500 MHz, CDCl$_3$, Ref=0.000 ppm (TMS)]
δ;4.514(1H, dd, J=12.82, H-6)
4.667(1H, dd, J=4.77, H-6')
4.751–4.716(1H, m, H-5)
5.328(1H, dd, J=9.89, H-2)
5.818(1H, t, H-4)
6.263(1H, t, H-3)
6.865(1H, d, J=4.03, H-1)
8.068, 8.002, 7.952, 7.874(8H, 4d, J=8.06, C$_6$H$_5$CO—)

3) Synthesis of glucosylbetamethasone (benzoyl derivative) 100  99+86→100

Betamethasone (86) (510 mg) was dissolved in acetonitrile (35 ml), and to this solution were added molecular sieve 3A (700 mg) and silver triflate (668 mg). To this mixture was added, under an argon atmosphere and at 0–5° C., a glucose bromide (benzoyl derivative) (99) (1.72 g) dissolved in acetonitrile (18 ml). While the reaction mixture was slowly raised to room temperature, the reaction mixture was stirred for 5 h. To this mixture was further added silver triflate (668 mg), and the resulting mixture was stirred at room temperature for 18 h. The reaction solution was filtered, and the solvent was distilled off from the mother liquor in vacuo. The residue thus obtained was dissolved in chloroform, and was washed with saturated sodium chloride solution. After the chloroform solution was dried over anhydrous magnesium sulfate, the solvent was evaporated in vacuo. The residue thus obtained was purified by silica gel colum chromatography (hexane:ethyl acetate=5:4) to give white powder (1.24 g), which was further purified by HPLC using a reversed phase partition chromatography (acetonitrile-water) to give β-anomer (100β) as white powder [813 mg (yield 64.4%)].

Compound 100β
C$_{56}$H$_{55}$O$_{14}$F MW=971.04
$^1$H-NMR [500 MHz, CDCl$_3$, Ref=0.000 ppm (TMS)]
δ;4.149–4.112(1H, m, H-5)
5.064(1H, d, J=8.06, H-1)
5.562(1H, dd, J=9.53, H-2)
5.695(1H, t, H-4)
5.917(1H, t, H-3)
6.126(1H, s, Bet-4)
6.339(1H, d, Bet-1)
7.990, 7.947, 7.926, 7.832(8H, 4d, J=8.43, C$_6$H$_5$CO—)
FAB(+)MS calcd. 970.36;993 (M+Na)$^+$
MP:142–145° C.
IR ν$_{max}^{KBr}$cm$^{-1}$ 1734(C=O position-20), 1665(C=O position-3)

EXAMPLE 17

Figure 17:
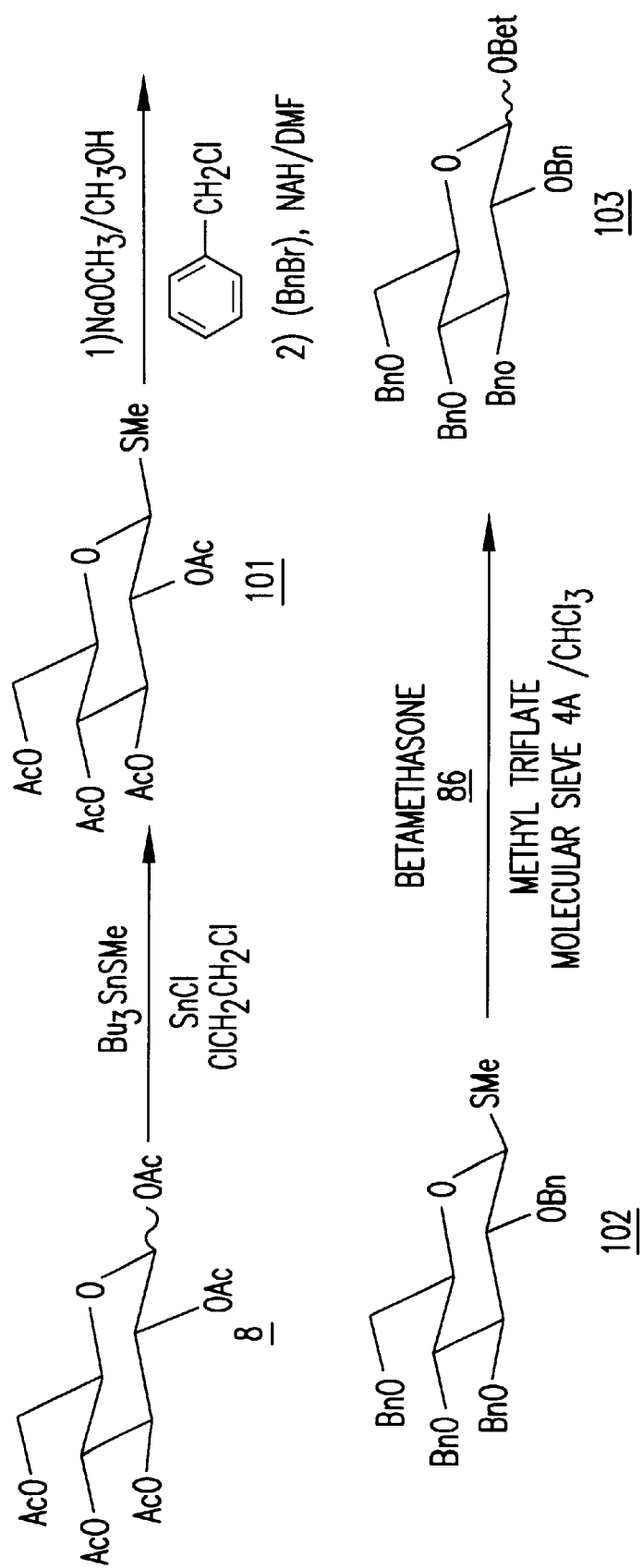
FIG. 17 is a flow-chart showing the synthesis route of glucosylbetamethasone (benzyl derivative).
Figure 18:
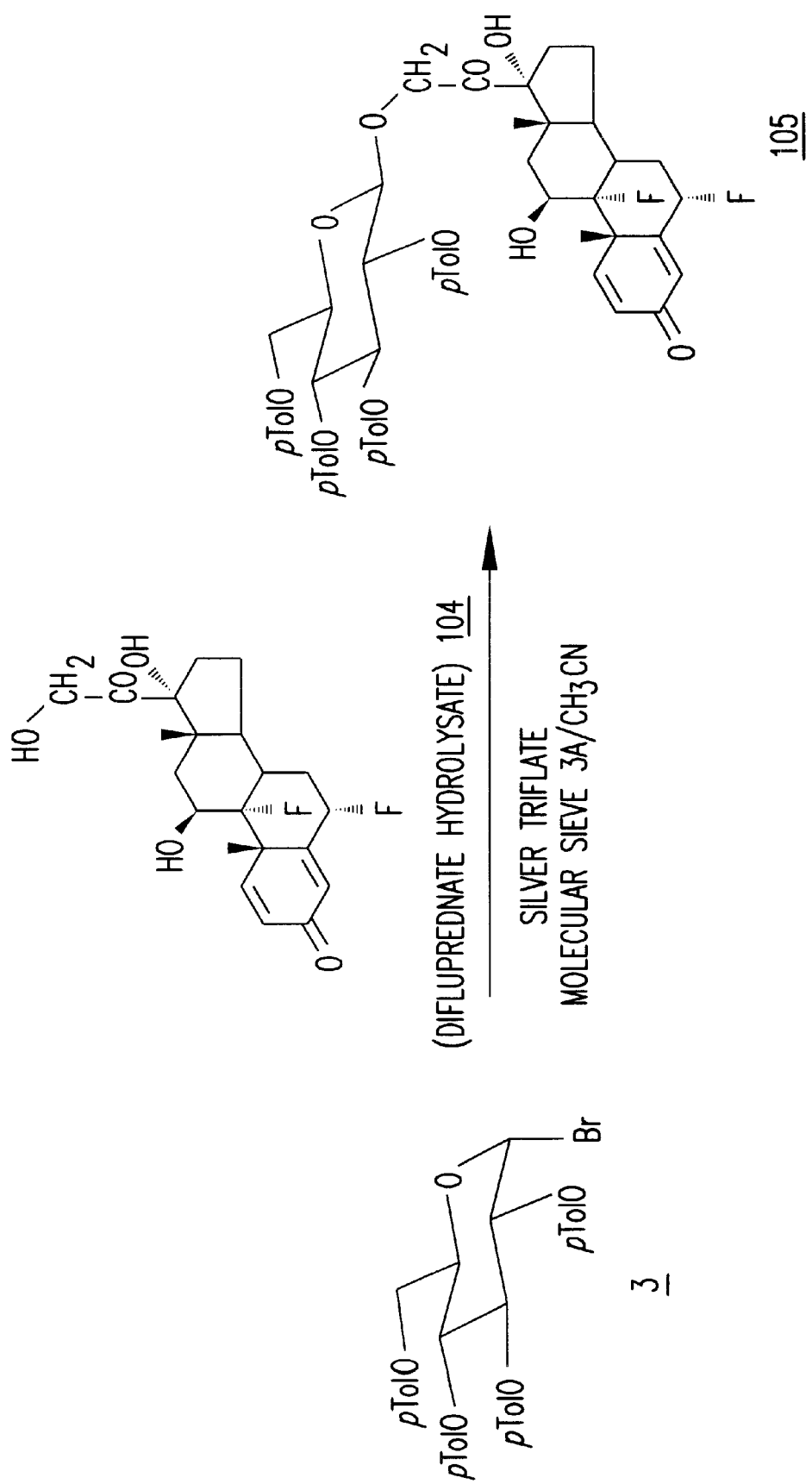
FIG. 18 is a flow-chart showing the synthesis route of glucosyldiflupredonate (p-toluoyl derivative).
Figure 19:
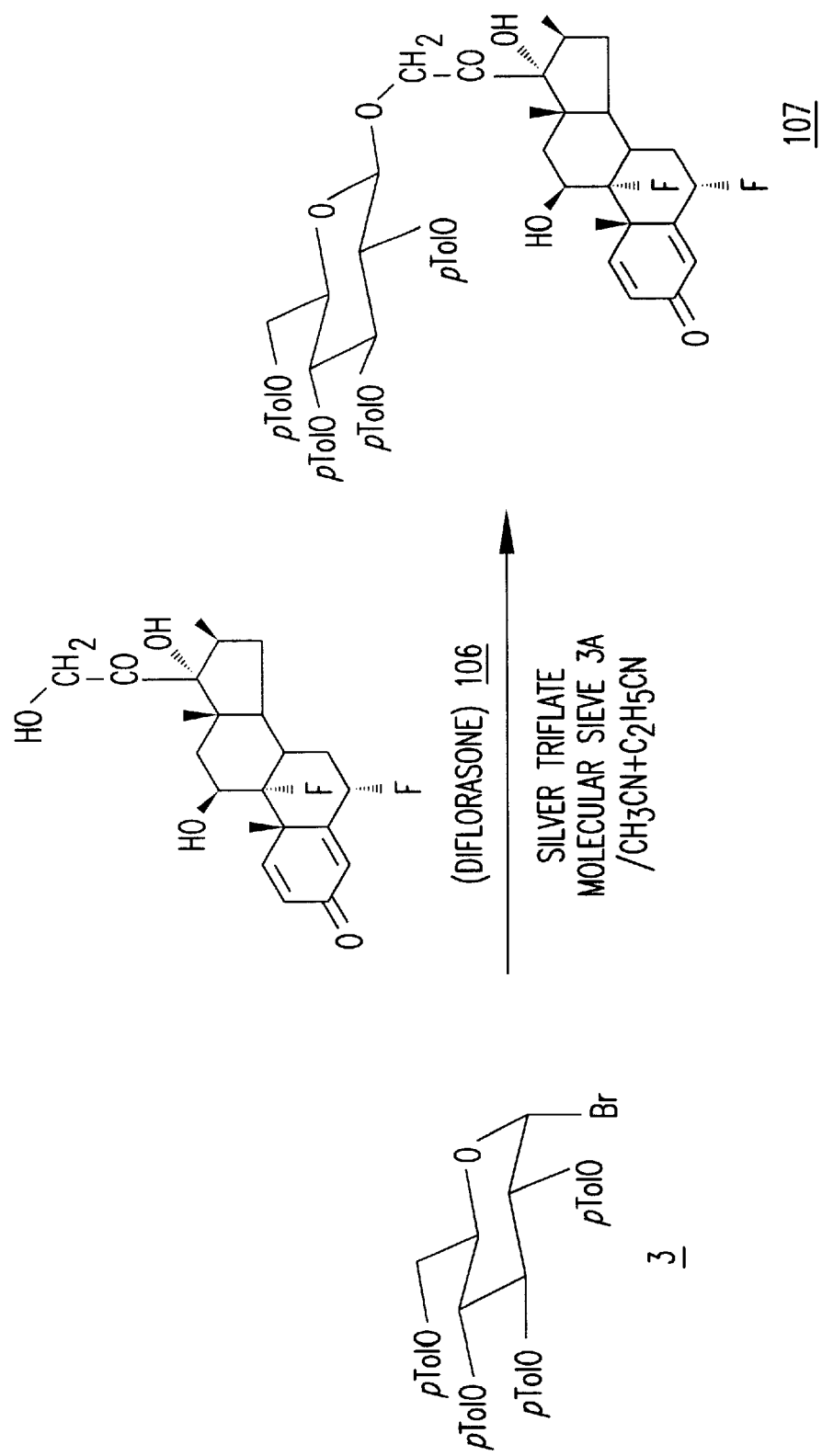
FIG. 19 is a flow-chart showing the synthesis route of glucosyldiflorasone (p-toluoyl derivative).
Figure 20:
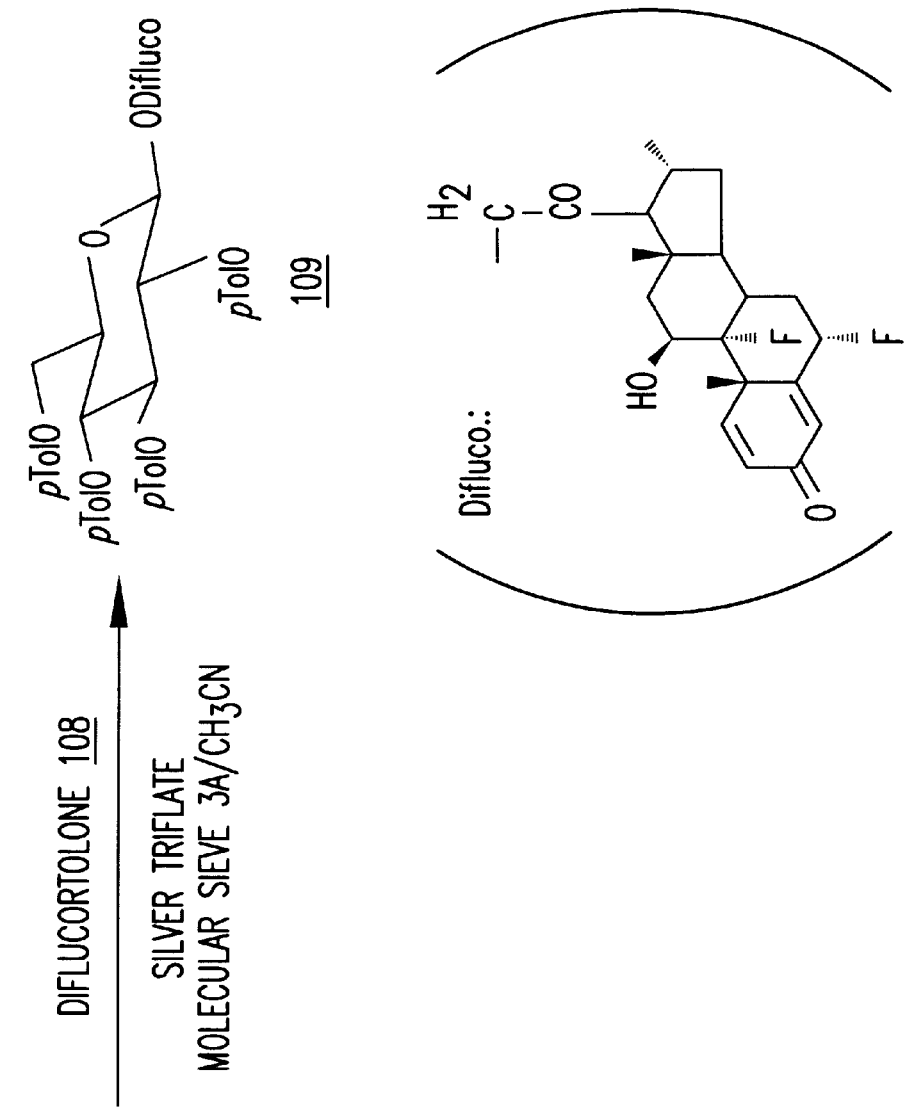
FIG. 20 is a flow-chart showing the synthesis route of glucosyldiflucortolone (p-toluoyl derivative).
Figure 21:
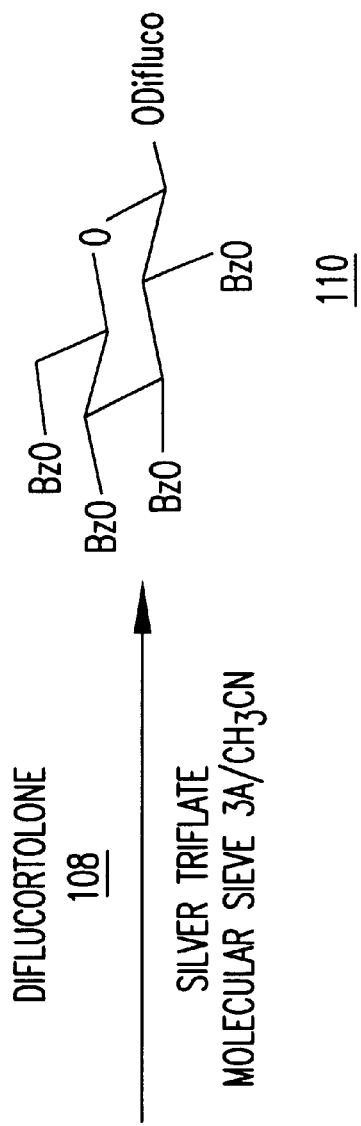
FIG. 21 is a flow-chart showing the synthesis route of glucosyldiflucortolone (benzoyl derivative).
Figure 22:
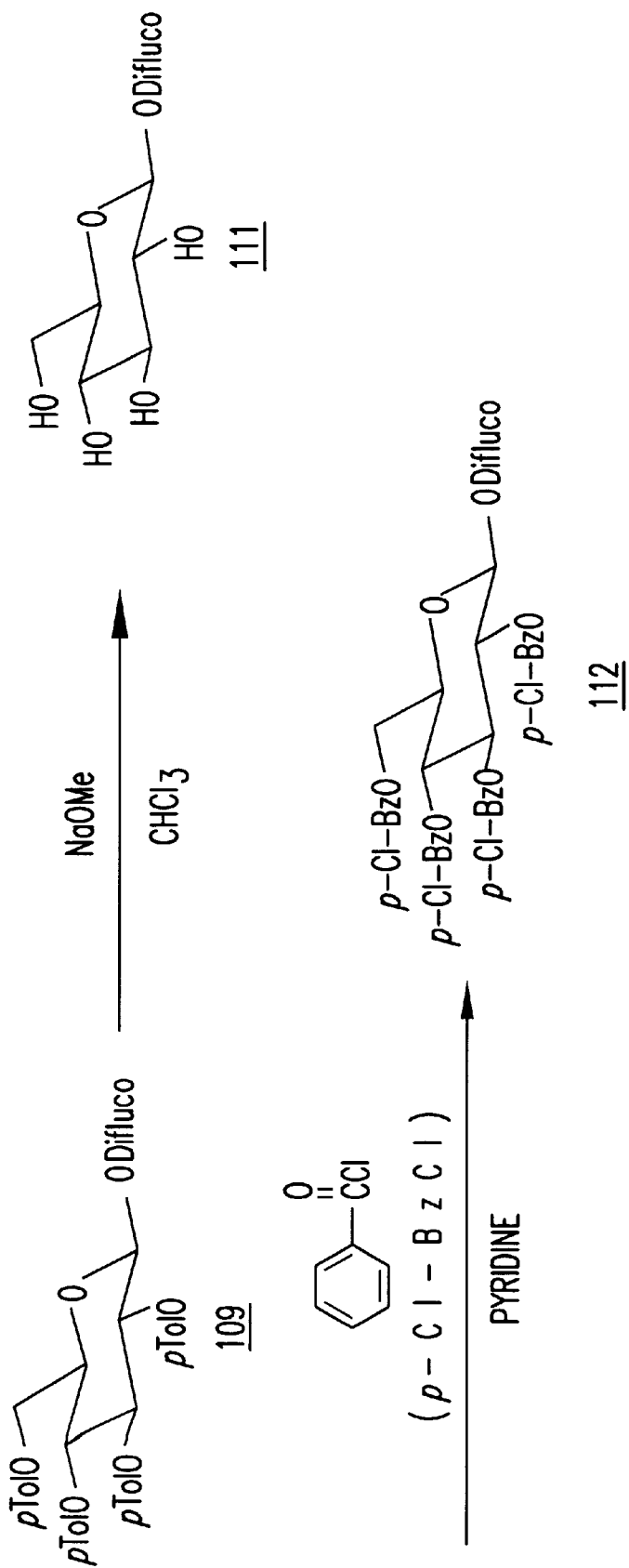
FIG. 22 is a flow-chart showing the synthesis route of glucosyldiflucortolone (p-chlorobenzoyl derivative).
Figure 23:
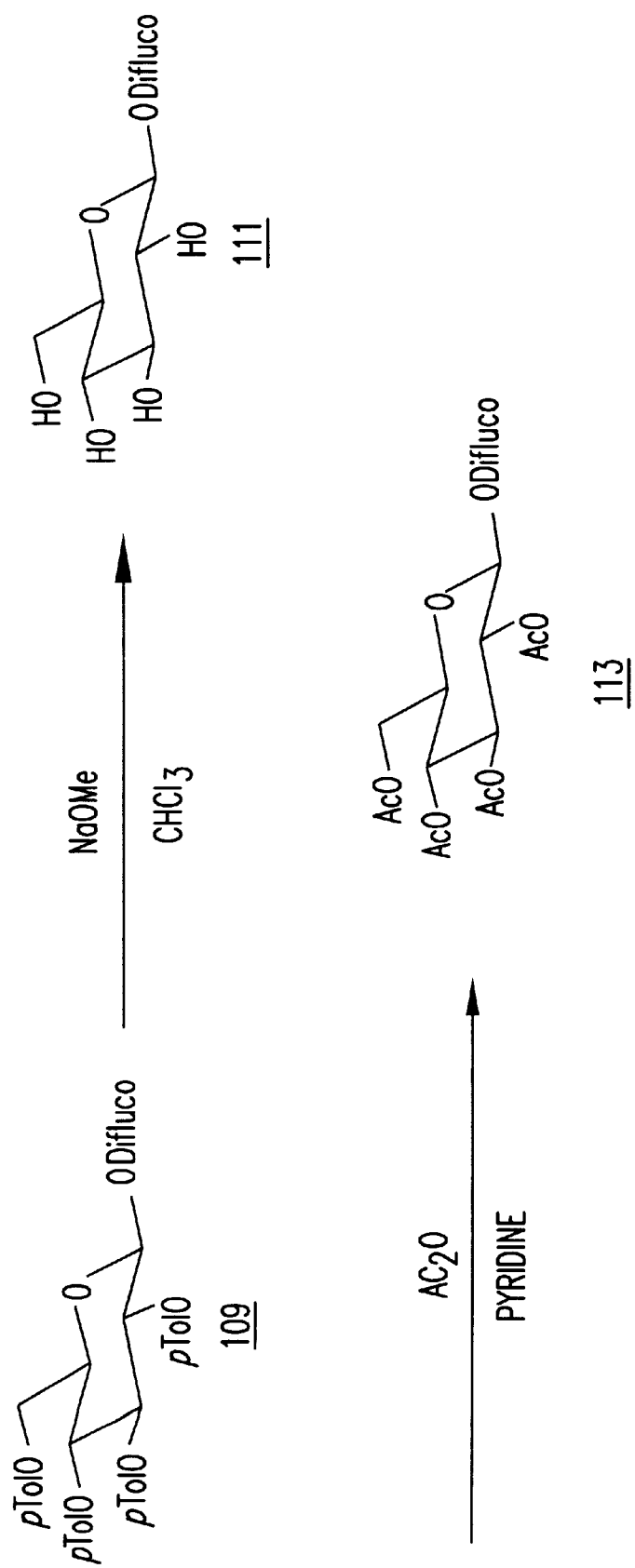
FIG. 23 is a flow-chart showing the synthesis route of glucosyldiflucortolone (acetyl derivative).

Synthesis of glucosylbetamethasone (benzyl derivative) (FIG. 17)

1) S-Methylation of glucose 8→101

β-D-Glucose-penta-O-acetate (8) (5 g) and tributyltin methylsulfide (6.5 g) were suspended in dichloroethane (40 ml), and to this suspension was added, under ice-cooling, tin(IV) chloride (1.94 ml). The resulting mixture was stirred at 0° C. for 5 h. After the reaction mixture was diluted with chloroform, a potassium fluoride solution was added to the above mixture, and stirred at room temperature. The reaction solution was filtered through celite, and the mother liquor was washed successively with saturated sodium bicarbonate solution, water, and saturated sodium chloride solution. After the organic layer was dried over anhydrous magnesium sulfate, the solvent was distilled off from the solution in vacuo. The residual material thus obtained was purified by silica gel column chromatography (hexane:ethyl acetate= 3:2) to give 101 as white powder [4.5 g (yield 93.2%)].

Compound 101
C$_{15}$H$_{22}$O$_9$S MW=378.39
$^1$H-NMR [500 MHz, CDCl$_3$, Ref=0.000 ppm(TMS)]
δ;2.086, 2.069, 2.030, 2.013(12H, 4s, CH$_3$COO—)
2.173(3H, s, CH$_3$S—)
3.754–3.720(1H, m, H-5)
4.151(1H, dd, J=12.46, H-6)
4.256(1H, dd, J=5.13, H-6')
4.399(1H, d, J=9.90, H-1)
5.107–5.056(2H, m, H-2, H-4)
5.235(1H, t, J=9.52, H-3)

2) Benzylation of glucose (S-methyl derivative) 101→102

Glucose (S-methyl derivative) (101) (400 mg) was dissolved in methanol (6 ml), and to this solution was added 1 M sodium methoxide (0.5 ml) at 0–5° C. The mixture was stirred at room temperature for 5 h. After the solvent was distilled off from the reaction mixture in vacuo, the residual material was dissolved in DMF (9 ml), and to this solution were added benzyl bromide (1.45 g) at 0° C., followed by sodium hydride (0.4 mg). The resulting mixture was stirred for 3 h, while it was allowed to warm up slowly to room temperature. Then, to this reaction mixture was added methanol under ice-cooling, and the resulting mixture was evaporated in vacuo. To the residue thus obtained was added diethyl ether, and the solution was washed with saturated sodium chloride solution. After the solution was dried over anhydrous magnesium sulfate, the solvent was distilled off in vacuo. The residual material thus obtained was purified by silica gel column chromatography (hexane:ethyl acetate= 7:1) to give 102 as white powder [445.2 mg (yield 73.8%)].

Compound 102
C$_{35}$H$_{38}$O$_5$S MW=570.75
$^1$H-NMR [500 MHz, CDCl$_3$, Ref=0.000 ppm(TMS)]
δ;2.244(3H, s, CH$_3$S—)
4.362(1H, d, J=9.52, H-1)

3) Synthesis of glucosylbetamethasone (benzyl derivative) 103  102+86→103

Betamethasone (86) (114 mg) and glucose (O-benzyl, SMe-derivative) (102) (200 mg) were dissolved in chloroform (6 ml), and to this solution were added molecular sieve 4A (80 mg), followed by methyl triflate (75 μl) at −20° C. While the reaction temperature was slowly raised to room temperature, the mixture was stirred for 5 h. The reaction solution was basified by the addition of triethylamine, filtered, and the solvent was distilled off from the mother liquor in vacuo. The residue was then diluted with chloroform, and the resulting solution was washed with saturated solutions of sodium bicarbonate and sodium chloride. After the solution was dried over anhydrous magnesium sulfate, the solvent was distilled off in vacuo. Residual material thus obtained was purified by silica gel column chromatography (hexane:ethyl acetate=5:4) to give 103 (mixture of α-, β-anomers, α:β=3:1) as white powder [200 mg (yield 75.4%)].

Compound 103
$C_{56}H_{63}O_{10}F$ MW=915.11
$^1$H-NMR [500 MHz, $CDCl_3$, Ref=0.000 ppm(TMS)]
δ; 3.492(0.25H, dd, H-2, β)
3.598(0.75H, dd, H-2, α)
4.504(0.25H, d, J=7.70, H-1, β)
4.823(0.75H, d, J=4.03, H-1, α)
6.110(0.25H, s, Bet-4, β)
6.143(0.75H, s, Bet-4, α)
6.310(0.25H, s, Bet-1, β)
6.338(0.75H, s, Bet-1, α)
FAB(+)MS calcd., 914.44;915(M+H)$^+$
MP:80–83° C.
IR $v_{max}^{KBr}$cm$^{-1}$ 1725(C=O position–20), 1663(C=O position–3)

EXAMPLES 18–23

Syntheses of glucosyldifluorosteroids (FIGS. 18–23)

1) Synthesis of glucosyldiflupredonate (p-toluoyl derivative) 105  3+104→105

Diflupredonate hydrolysate (104) (315 mg) was dissolved in acetonitrile (18 ml), and to this solution were added molecular sieve 3A (439 mg) and silver triflate (409 mg). To this mixture was added, under an argon atmosphere and at 0–5° C., a glucose bromide (3) (1.14 g) dissolved in acetonitrile (18 ml). While the reaction temperature was raised slowly to room temperature, the resulting mixture was stirred for 2 h. To this mixture was further added silver triflate (409 mg), and the resulting mixture was stirred at room temperature for 18 h. After the reaction solution was filtered, the solvent of the mother liquor was evaporated in vacuo. The residue was dissolved in chloroform, and washed with saturated sodium chloride solution. After the solution was dried over anhydrous magnesium sulfate, the solvent was evaporated in vacuo. The residue thus obtained was purified by silica gel column chromatography (hexane:ethyl acetate=2:1) to give white powder (870 mg). This product was further purified by HPLC using a reversed phase partition column (acetonitrile-water) to give β-anomer ( 105β) as white powder [641 mg (yield 78.2%)].

Compound 105β
$C_{59}H_{60}O_{14}F_2$ MW=1031.11
$^1$H-NMR [500 MHz, $CDCl_3$, Ref=0.000 ppm(TMS)]
δ:2.420, 2.371, 2.340, 2.296(12H, 4s, $CH_3C_6H_4O$—)
4.085–4.047(1H, m, H-5)
4.561(1H, dd, H-6)
4.792(1H, dd, H-6')
4.889(1H, d, J=8.06, H-1)
5.454(1H, dd, H-2)
5.633(1H, t, H-3)
5.913(1H, t, H-4)
7.869, 7.849, 7.828, 7.740(8H, 4d, J=8.43, $CH_3C_6H_4O$—)
FAB(+)MS calcd. 1030.4;1031(M+H)$^+$, 1013(M–H$_2$O)$^+$
MP:152–155° C.
IR $v_{max}^{KBr}$cm$^{-1}$ 1733(C=O position–20), 1630(C=O position–3)

2) Synthesis of glucosyldiflorasone (p-toluoyl derivative) 107  3+106→107

Hydrolysate of diflorasone (p-toluoyl derivative) (106) (206 mg) and a glucose bromide (3) (720 mg) were dissolved in a mixture of acetonitrile (3 ml) and cyanoethane (5 ml). To this solution was added molecular sieve 3A (1.0 g), and the mixture was stirred at room temperature for 3 h. This mixture was cooled to 0° C., and to the cooled mixture was added silver triflate (262 mg) dissolved in cyanoethane (1 ml). The resulting mixture was stirred for 20 h, while the reaction temperature was slowly raised to room temperature under an argon atmosphere. The reaction solution was diluted with chloroform, filtered through celite, and the mother liquor was washed with saturated sodium bicarbonate solution and then with saturated sodium chloride solution. After the chloroform solution was dried over anhydrous magnesium sulfate, the solvent was distilled off in vacuo. The residue thus obtained was purified by silica gel column chromatography (toluene:ethyl acetate=7:3) to give white powder (317 mg). This product was further purified by HPLC using reversed phase partition column (acetonitrile-water) to give β-anomer (107β) as white powder [231 mg (yield 44.4%)].

Compound 107β
$C_{60}H_{62}O_{14}F_2$ MW=1045.14
$^1$H-NMR [500 MHz, $CDCl_3$, Ref=0.000 ppm(TMS)]
δ:2.387, 2.354, 2.351, 2.291(12H, 4s, $CH_3C_6H_4O$—)
4.120–4.084(1H, m, H-5)
4.278(1H, t, H-6)
4.582(1H, t, H-6')
4.999(1H, d, J=8.06, H-1)
5.516(1H, dd, H-2)
5.644(1H, t, H-4)
5.873(1H, t, H-3)
6.358(1H, d, Diflora-1)
6.427(1H, s, Diflora-4)
7.860, 7.830, 7.786, 7.717(8H, 4d, J=8.06, $CH_3C_6H_4O$—)
FAB(+)MS calcd. 1044.41;1045(M+H)$^+$, 1067(M+Na)$^+$,
IR $v_{max}^{KBr}$cm$^{-1}$ 1733(C=O position–20), 1671(C=O position–3)

3) Glucosyldiflucortolone (p-toluoyl derivative) 109  3+108→109

Hydrolysate of diflucortolone (108) (200 mg) was dissolved in acetonitrile (2 ml), and to this solution was added molecular sieve 3A (2 g). The mixture was stirred for 30 min. To this mixture were added, under an argon atmosphere and at 0–5° C., a glucose bromide (3) (725 mg) dissolved in acetonitrile (1 ml) and silver triflate (261 mg), and the resulting mixture was stirred for 2.5 h, while the reaction temperature was raised slowly to room temperature. After the reaction solution was filtered, the solvent was distilled off from the mother liquor in vacuo, and the residue was dissolved in ethyl acetate. The solution was washed with saturated sodium bicarbonate solution, then with saturated sodium chloride solution, and dried over anhydrous magnesium sulfate. After the solvent was distilled off in vacuo, the residue thus obtained was purified by silica gel column chromatography (toluene:ethyl acetate=4:1) to give white powder (379 mg). A 370-mg portion of the product was further purified by HPLC using a reversed phase partition column (acetonitrile-water) to give β-anomer (109β) as white powder [289 mg (yield 55.1%)].

Compound 109β
$C_{60}H_{62}O_{13}F_2$ MW=1029.14
$^1$H-NMR [500 MHz, $CDCl_3$, Ref=0.000 ppm(TMS)]
δ:2.421, 2.364, 2.341, 2.293(12H, 4s, $CH_3C_6H_4O$—)
4.070–4.033(1H, m, H-5)
4.972(1H, d, J=8.06, H-1)
5.478(1H, dd, H-2)
5.639(1H, t, H-3)
5.884(1H, t, H-4)
6.370(1H, d, Difluco-1)
6.437(1H, s, Difluco-4)

7.872, 7.831, 7.822, 7.729(8H, 4d, J=8.06, CH$_3$C$_6$H$_4$O—)
FAB(+)MS calcd. 1028.4; 1029(M+H)$^+$
MP:144–147° C.
IR $\nu_{max}^{KBr}$cm$^{-1}$ 1734(C=O position–20), 1672(C=O position–3)

4) Synthesis of glucosyldiflucortolone (benzoyl derivative) 99+108→110α+110β

Hydrolysate of diflucortolone (108) [299.1 mg (0.758 mmol)] was dissolved in acetonitrile (20 ml), and to this solution were added molecular sieve 3A (about 700 mg) and silver triflate [390.6 mg (1.52 mmol)]. The mixture was stirred for 1 h. To this mixture was added, under an argon atmosphere and at 0° C., a benzoylglucose bromide (99) [1.0 g (1.52 mmol)] dissolved in acetonitrile (10 ml). While the reaction temperature was slowly raised to room temperature, the mixture was stirred for 2 h. To this mixture was further added silver triflate (390.6 mg), and the resulting mixture was stirred at room temperature for 14 h. To this mixture was further added silver triflate (390.6 mg), and the resulting mixture was stirred at room temperature for 4 h. After the reaction solution was filtered, the solvent was distilled off from the filtrate in vacuo. The residue thus obtained was dissolved in chloroform, and the solution was washed with saturated sodium chloride solution. After the solution was dried over anhydrous magnesium suflate, the solvent was distilled off in vacuo. The residue thus obtained was purified by silica gel column chromatography (ethyl acetate:hexane= 2:3→4:5) to give fractions containing the desired product (360.2 mg). This product was further purified by HPLC using a reversed phase partition column (water-acetonitrile) to give α-anomer (110α) [19.9 mg (yield 2.7%)] and β-anomer (110β) [249.9 mg (yield 33.9%)], respectively, both as white powder.

Compound 110α
C$_{56}$H$_{54}$F$_2$O$_{13}$ MW=972.35
MP:135–138° C.
FAB(+)MS;955(M–H$_2$O)$^+$, 973(M+H)$^+$, 995(M+Na)$^+$
IR $\nu_{max}^{KBr}$cm$^{-1}$: 3448(O–H), 1731(COPh), 1671(C=O 3-position), 1616 and 1603(C=C)
$^1$H-NMR[500 MHz, CDCl$_3$, Ref=0.000 ppm(TMS)]
δ;7.169(1H, d, J$_{2,1}$=10.3, H-2)
6.437(1H, d, J$_{4,1}$=1.8, H-4)
6.408(1H, dd, H-1)
6.250(1H, t, J$_{3,2}$=9.9, J$_{3,4}$=9.9, H-3$_{Glc}$)
5.780(1H, t, J$_{4,5}$=10.3, H-4$_{Glc}$)
5.338(1H, d, J$_{1,2}$=3.7, H-1$_{Glc}$)
5.223(1H, dd, H-2$_{Glc}$)
4.917(1H, dd, J$_{6,5}$=3.3, J$_{6,6'}$=12.5, H-6$_{Glc}$)
4.657(1H, ddd, J$_{6,6'}$=2.6, H-5$_{Glc}$)
4.296(1H, dd, H-6'$_{Glc}$)
4.249(1H, d, J$_{gem}$=17.6, H-21)
4.231(1H, d, H-21')
1.553(3H, s, H-19)
1.077(3H, s, H-18)
0.968(3H, d, J$_{16CH3,16}$=7.0, 16-CH$_3$)
Compound 110β
C$_{56}$H$_{54}$F$_2$O$_{13}$ MW=972.35
MP:140–145° C.
FAB(+)MS; 955(M–H$_2$O)$^+$, 973(M+H)$^+$, 995(M+Na)$^+$
IR $\nu_{max}^{KBr}$cm$^{-1}$: 3440(O–H), 1731(COPh), 1671(C=O position–3), 1604(C=C)
$^1$H-NMR [500 MHz, CDCl$_3$, Ref=0.000 ppm(TMS)]
δ;7.115(1H, dd, J$_{2,1}$=10.3, H-2)
6.438(1H, d, J$_{4,1}$=1.8, H-4)
6.374(1H, dd, H-1)
5.927(1H, t, J$_{3,2}$=9.9, J$_{3,4}$=9.9, H-3$_{Glc}$)
5.704(1H, t, J$_{4,5}$=9.9, H-4$_{Glc}$)
5.519(1H, dd, J$_{2,1}$=7.7, H-2$_{Glc}$)
5.038(1H, d, H-1$_{Glc}$)
4.691(2H, dd, J$_{6,5}$=4.0, H-6$_{Glc}$)
4.268(1H, d, J$_{gem}$=16.9, H-21)
4.133(1H, d, H-21')
4.084(1H, td, H-5$_{Glc}$)
1.558(3H, s, H-19)
0.900(3H, s, H-18)
0.821(3H, d, J$_{16CH3,16}$=7.0, 16-CH$_3$)

5) Synthesis of glucosyldiflucortolone (p-chlorobenzoyl derivative)112
109→111→112

Glucosyldiflucortolone (p-toluoyl derivative; 109) (1.34 g) was dissolved in chloroform (40 ml), and to this solution was added, under ice-cooling, 1 M sodium methoxide (1.04 ml). While the reaction temperature was slowly raised to room temperature, the mixture was stirred for 1 h. To this reaction solution was added methanol (30 ml), and the resulting mixture was stirred for 3 h. The reaction solution was applied to a gel filtration column of LH-20, and eluted with methanol. The solvent of fractions containing product was distilled off in vacuo, and the residue thus obtained was recrystallized from methanol to give glucosyldiflucortolone (deprotected derivative; 111) (408.4 mg). To a portion of the product (102.5 mg) were added, at 0–5° C., p-chlorobenzoyl chloride (190 μl) and pyridine (0.9 ml), and, while the reaction temperature was slowly raised to room temperature, the mixture was stirred for 6 h. Then, to the mixture was added methanol (1 ml), and the resulting mixture was stirred at room temperature for 30 min. The reaction solution was applied to a gel filtration column of LH-20, and eluted with methanol. After the solvent of fractions containing product was distilled off in vacuo, the residue thus obtained was purified by silica gel column chromatography (toluene:ethyl acetate=4:1) to give 112 as white powder [152.2 mg (yield 42.0%) (109→112 in two steps)].

Compound 111
C$_{28}$H$_{38}$O$_9$F$_2$ MW=556.60
$^1$H-NMR [500 MHz, DMSO, Ref=0.000 ppm(TMS)]
δ:3.079(1H, t, J=5.49, H-6')
3.118(1H, t, J=8.43, H-2)
3.272(1H, d, J=7.79, H-3)
3.439(1H, dd, J=11.36, H-5)
4.161(1H, d, J=8.06, H-1)
6.107(1H, s, Difluco-4)
6.292(1H, d, Difluco-1)
FAB(+)MS calcd. 556.2;557(M+H)$^+$
MP:162–164° C.
IR $\nu_{max}^{KBr}$cm$^{-1}$;1716(C=O position–20), 1630(C=O position–3)

Compound 112
C$_{56}$H$_{50}$O$_{13}$Cl$_4$F$_2$ MW=1110.81
$^1$H-NMR [500 MHz, CDCl$_3$, Ref=0.000 ppm(TMS)]
δ:4.057(1H, ddd, J=4.03, H-5)
4.605(1H, dd, J=4.03, H-6')
4.693(1H, dd, J=12.45, H-6)
5.046(1H, d, J=7.70, H-1)
5.471(1H, dd, J=9.53, H-2)
5.654(1H, t, J=9.86, H-4)
5.843(1H, t, J=9.86, H-3)
7.286, 7.349, 7.352, 7.411(8H, 4d, J=8.79, ClC$_6$H$_4$CO—)
7.762, 7.838, 7.890, 7.902(8H, 4d, J=8.79, ClC$_6$H$_4$CO—)
FAB(+) MS calcd. 1108.2; 1109(M+H)$^+$
MP:147–149° C.
IR $\nu_{max}^{KBr}$cm$^{-1}$: 1738(C=O position–20), 1634(C=O position–3)

6) Synthesis of glucosyldiflucortolone (acetyl derivative) 113 109→113

Glucosyldiflucortolone (p-toluoyl derivative; 109) (1.55 g) was dissolved in chloroform (50 ml), and to this solution was added, under ice-cooling, 1 M sodium methoxide (1.21 ml). While the reaction temperature was slowly raised to room temperature, the mixture was stirred for 1 h. Then, to the reaction solution was added methanol (40 ml), and the mixture was stirred at room temperature for 3 h. After the solvent was distilled off in vacuo, acetic anhydride (8.0 ml) and pyridine (1.8 ml) were added to the residue under ice-cooling, and the resulting mixture was slowly raised to room temperature, the mixture was stirred for 2 h. To this mixture was further added acetic anhydride (2.6 ml) and pyridine (0.6 ml), the mixture was stirred for 3 h. The reaction solution was poured into ice-water, extracted with chloroform, and the chloroform solution was washed successively with saturated sodium bicarbonate solution, 5% copper sulfate solution, and saturated sodium chloride solution. The chloroform solution was dried over anhydrous magnesium sulfate, and then the solvent was evaporated in vacuo. The residue thus obtained was recrystallized from ethyl acetate to give 113 as white powder [668 mg (yield 61.2%)].

Compound 113
$C_{36}H_{46}O_{13}F_2$ MW=724.75
$^1$H-NMR [500 MHz, $CDCl_3$, Ref=0.000 ppm(TMS)]
δ:2.117, 2.069, 2.051, 2.019(12H, 4s, $CH_3COO$—)
  3.663(1H, ddd, J=5.13, H-5)
  4.198(1H, dd, J=2.93, H-6')
  4.389(1H, dd, J=12.46, H-6)
  4.733(1H, d, J=8.06, H-1)
  5.005(1H, dd, J=9.52, H-2)
  5.007(1H, t, J=9.52, H-4)
  5.235(1H, t, J=9.52, H-3)
  6.383(1H, d, Difluco-1)
  6.429(1H, s, Difluco-4)
FAB(+)MS calcd. 724.3;725(M+H)$^+$
MP:233–235° C.
IR $v_{max}^{KBr}$cm$^{-1}$ 1760(C=O position-20), 1671(C=O position-3)

EXAMPLE 24

Figure 24:
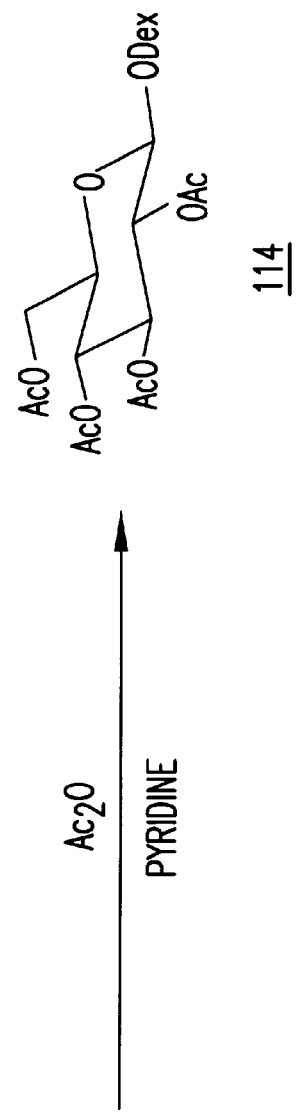
FIG. 24 is a flow-chart showing the synthesis route of glucosyldexamethasone (acetyl derivative).
Figure 24:
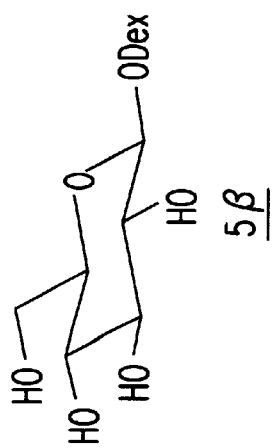

Synthesis of glucosyldexamethasone (acetyl derivative) (FIG. 24)

1) Glucosyldexamethasone (acetyl derivative) 5β→114β

A deprotected derivative (5β) of glucosyldexamethasone (β-anomer) (278 mg) was dissolved in acetic anhydride (1.75 ml), and to this solution was added, under ice-cooling, pyridine (0.40 ml). While the reaction temperature was slowly raised to room temeprature, themixture was stirred for 1 h. The reaction solution was poured into ice-water, and extracted with chloroform. The chloroform solution was washed successively with saturated sodium bicarbonate solution, 5% copper sulfate solution, and saturated sodium chloride solution. After the chloroform solution was dried over anhydrous magnesium sulfate, the solvent was evaporated in vacuo. The residue thus obtained was purified by silica gel column chromatography (hexane:ethyl acetate= 1:2) to give white powder (198 mg). This product was further purified by HPLC using a reversed phase partition column (acetonitrile-water) to give 114β as white powder [147 mg (yield 40.5%)].

Compound 114β
$C_{36}H_{47}O_{14}F$ MW=722.76
$^1$H-NMR [500 MHz, $CDCl_3$, Ref=0.000 ppm(TMS)]
δ: 2.119, 2.094, 2.047, 2.022(12H, 4s, $CH_3COO$—)
  3.690–3.654(1H, m, H-5)
  4.219(1H, dd, J=12.09, 3.29, H-6)
  4.336(1H, dd, J=4.77, H-6')
  4.746(1H, d, J=8.06, H-1)
  5.027(1H, dd, J=9.15, H-2)
  5.087(1H, t, H-4)
  5.245(1H, t, H-3)
  6.121(1H, s, Dex-4)
  6.347(1H, d, Dex-1)
FAB(+)MS calcd. 722.29; 723(M+H)$^+$, 705(M–H$_2$O)$^+$
MP:125–128° C.
IR $v_{max}^{KBr}$cm$^{-1}$1758(C=O position-20), 1666(C=O position-3)

EXAMPLE 25

Figure 25:
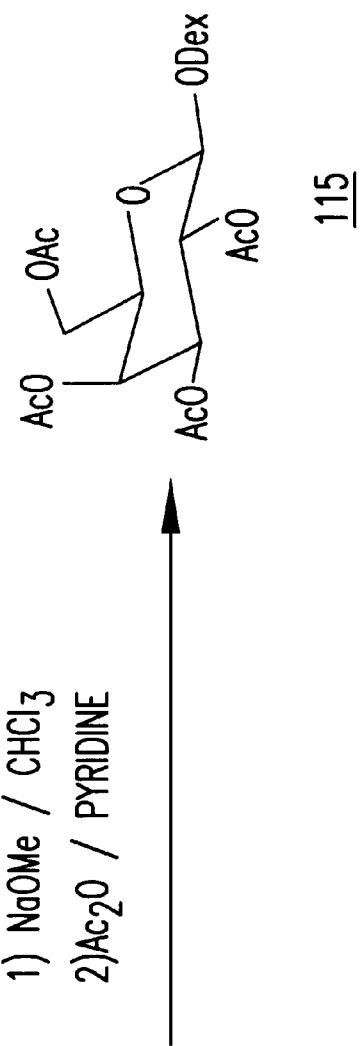
FIG. 25 is a flow-chart showing the synthesis route of galactosyldexamethasone (acetyl derivative).
Figure 25:
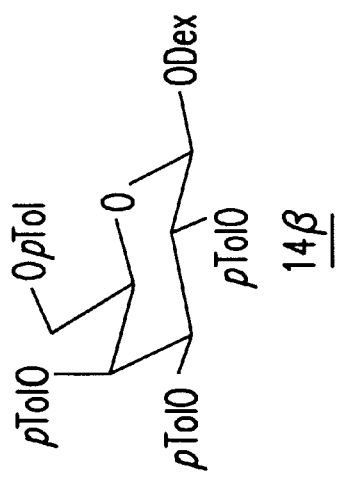
Figure 26:
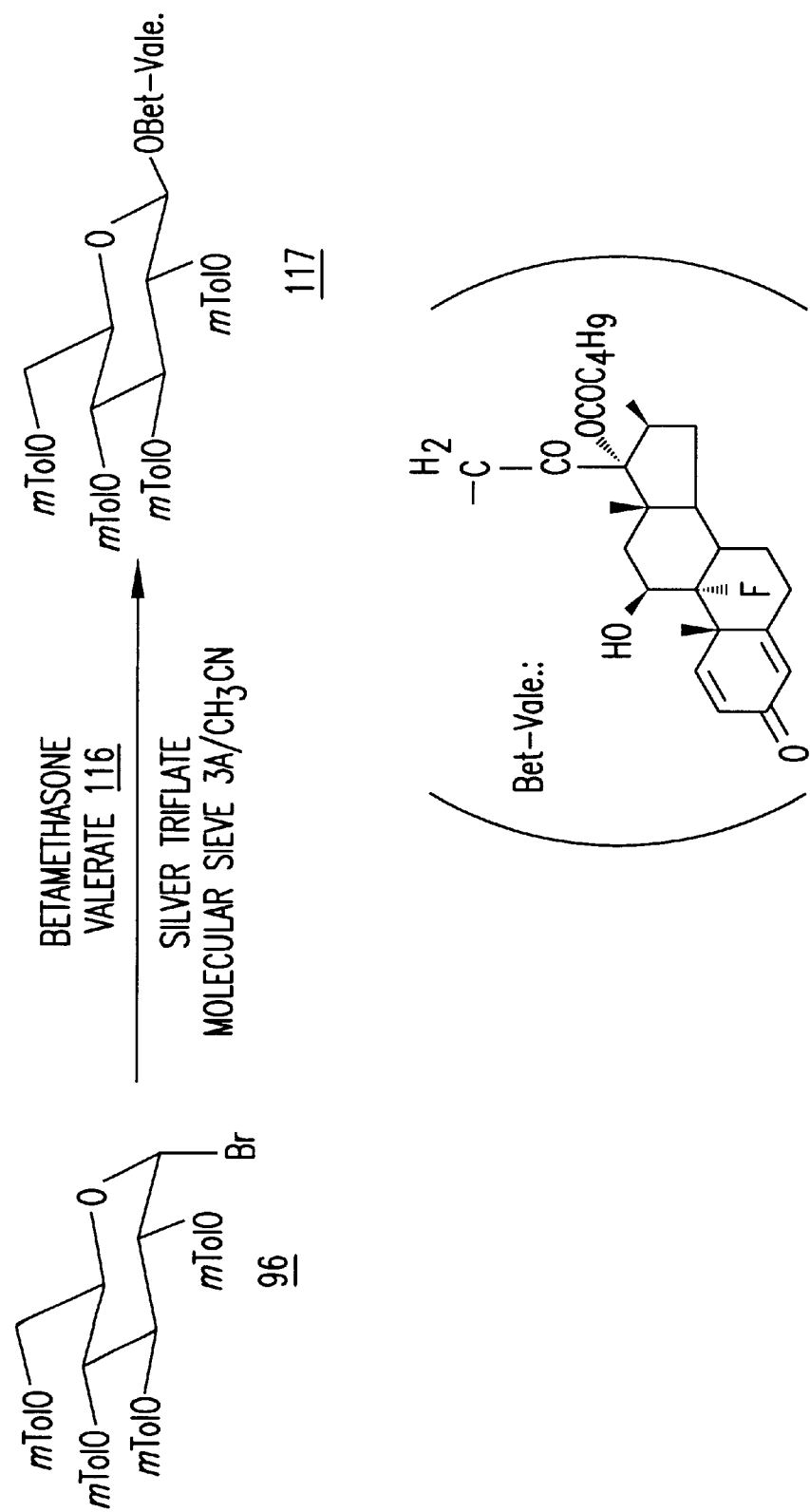
FIG. 26 is a flow-chart showing the synthesis route of glucosylbetamethasone valerate (m-toluoyl derivative).

Synthesis of galactosyldexamethasone (acetyl derivative) (FIG. 25)

1) Synthesis of galactosyldexamethasone (acetyl derivative) 115β 14β→115β

Galactosyldexamethasone (p-tolyoyl derivative; 14β) (762 mg) was dissolved in chloroform (25 ml), and to this solution was added, under ice-cooling, 1 M sodium methoxide (592 µl). While the reaction temperature was slowly raised to room temperature, the mixture was stirred for 2 h. To this reaction solution was added methanol (25 ml), and the mixture was stirred at room temperature for 1 h. After the solvent was evaporated in vacuo, acetic ahnydride (3.90 ml) and pyridine (0.90 ml) were added to the residue under ice-cooling. While the reaction temperature was raised slowly to room temperature, the mixture was stirred for 12 h. To this mixture were further added acetic anhydride (1.30 ml) and pyridine (0.30 ml), and the resulting mixture was stirred at room temperature for 4 h. The reaction solution was poured onto ice-water, and extracted with chloroform. The chloroform solution was washed successively with saturated sodium bicarbonate solution, 5% copper sulfate solution and saturated sodium chloride solution. After the solvent wad distilled off in vacuo, the residue thus obtained was purified by silica gel column chromatography (hexane:ethyl acetate=2:3) to give white powder (462 mg). This product was further purified by HPLC using a reversed phase partition column (acetonitrile-water) to give 115β as white powder [171 mg (yield 31.9%) ].

Compound 115β
$C_{36}H_{47}O_{14}F$ MW=722.76 $^1$H-NMR [500 MHz, $CDCl_3$, Ref=0.000 ppm (TMS)]
δ: 2.190, 2.132, 2.101, 2.002(12H, 4s, $CH_3COO$—)
  4.454(1H, dd, H-6')
  4.575(1H, d, J=8.06, H-1)
  4.621.(1H, dd, H-2)
  5.032(1H, t, H-3)
  5.239(1H, t, H-2)
  5.392(1H, d, H-4)
  6.115(1H, s, Dex-4)
  6.331(1H, d, Dex-1)
FAB(+)MS calcd. 722.29; 723(M+H)$^+$, 705(M–H$_2$O)$^+$
MP:138–141° C.
IR $v_{max}^{KBr}$cm$^{-1}$ 1753(C=O position-20), 1666(C=O position-3)

EXAMPLE 26

Synthesis of glucosylbetamethasone valerate (m-toluoyl derivative) (FIG. 16)

1) Synthesis of glucosylbetamethasone valerate (m-toluoyl derivative) 117

96+116→117

Betamethasone valerate (116) (405 mg) was dissolved in acetonitrile (23 ml), and to this solution were added molecular sieve 3A (460 mg) and silver triflate (437 mg). To this mixture was added, under an argon atmosphere and at 0–5° C., aglucose bromide (m-toluoyl derivative (96) (1.22 g). While the reaction temperature was raised slowly to room temperature, the mixture was stirred for 5 h. After the reaction solution was filtered, the solvent of the mother liquor was evaporated in vacuo. The residue was dissolved in chloroform, and washed with saturated sodium chloride solution. After the solution was dried over anhydrous magnesium sulfate, the solvent was evaporated in vacuo. The residue thus obtained was purified by silica gel column chromatography (hexane:ethyl acetate=5:4) to give white powder (779 mg). This product was further purified by HPLC using a reversed phase partition column (acetonitrile-water) to give β-anomer (117β) [407 mg (yield 43.1%] and αanomer (117α) [59 mg (yield 6.3%)], respectively, both as white powder.

Compound 117β
$C_{65}H_{71}O_{15}F$ MW=1111.2
$^1$H-NMR [500 MHz, CDCl$_3$, Ref=0.000 ppm(TMS)]
δ:2.352, 2.307, 2.290, 2.277(12H, 4s, $\underline{CH_3}C_6H_4O$—)
  4.088–4.051(1H, m, H-5)
  4.353(1H, d, J=9.16, H-6)
  4.663(1H, d, J=4.76, H-6')
  5.135(1H, d, J=8.06, H-1)
  5.481(1H, dd, H-2)
  5.675(1H, t, H-4)
  5.869(1H, t, H-3)
  6.181(1H, s, Bet-4)
  6.400(1H, d, Bet-1)
  7.800, 7.712, 7.475(8H, 3d, J=7.69, CH$_3$C$_6$H$_4$O—)
FAB(+)MS calcd. 1110.48;1111(M+H)$^{30}$, 1094(M-H$_2$O)$^+$
MP:113–115° C.
IR $v_{max}^{KBr}$cm$^{-1}$ 1734(C=O position–20), 1668(C=O position–3)

Compound 117α
$C_{65}H_{71}O_{15}F$ MW=1111.2
$^1$H-NMR [500 MHz, CDCl$_3$, Ref=0.000 ppm(TMS)]
δ:2.386, 2.339, 2.333, 2.284(12H, 4s, $\underline{CH_3}C_6H_4O$—)
  4.088–4.051(1H, m, H-5)
  5.330(1H, d, J=3.67, H-1)
  6.162(1H, s, Bet-4)
  6.385(1H, d, Bet-1)
  7.831, 7.772, 7.676(8H, 3d, J=8.06, CH$_3$C$_6$H$_4$O—)
FAB(+)MS calcd. 1110.48;1111(M+H)$^+$, 1094(M-H$_2$O)$^+$
MP:105–108° C.
IR $v_{max}^{KBr}$cm$^{-1}$ 1732(C=O position–20), 1668(C=O position–3)

Figure 27:
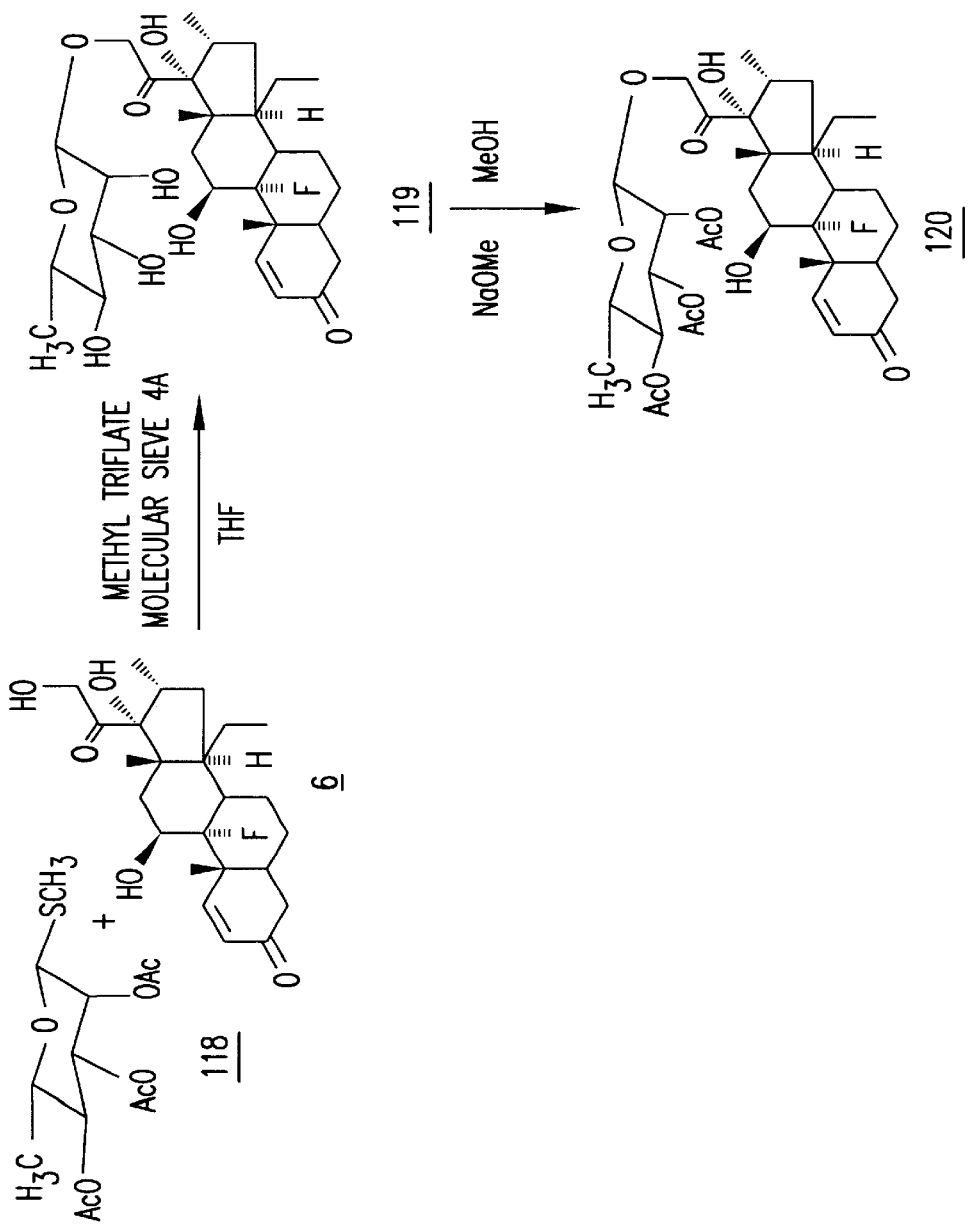
FIG. 27 is a flow-chart showing the synthesis route of β-rhamnosyldexamethasone.

Synthesis of β-rhamnosyldexamethasone (FIG. 27)
1) Synthesis of a protected (acetyl) derivative of rhamonosyldexamethasone 119(glucosylation)

Dexamethasone (6) (1.10 g) and rhamnose (o-acetyl, S-methyl derivative) 118 (1.12 g) were dissolved in tetrahydrofuran (10 ml, and this solution was added to molecular sieve 4A (1.2 g) contained in a brown reaction vessel. To this mixture was added, at −10° C., methyl triflate (2 ml), and, while the reaction temperature was slowly raised to room temperature, themixture was stirred for 4 h. The reaction solution was diluted with ethyl acetate (10 ml) and neutralized by the addition of triethylamine. The mixture was filtered, diluted with ethyl acetate (300 ml), and washed with saturated sodium bicarbonate solution followed by saturated sodium chloride solution. After the solution was dried over anhydrous magnesium sulfate, the solvent was evaporated in vacuo. The residue thus obtained was purified by silica gel column chromatography (toluene:acetone=1:1) to give 119β as white powder [312.5 mg (yield 16.8%)].

Compound 119β
$C_{34}H_{45}FO_{12}$ MW=664.72
Rf=0.62 (silica gel TLC, CHCl$_3$: methanol=20:1)
$^1$H-NMR [500 MHz, CDCl$_3$, Ref=0.000 ppm(TMS)]
δ; 7.213(1H, d, Dexa-H-2, $J_{2,1}$=10.3)
  6.336(1H, dd, Dexa-H-1, $J_{1,4}$=1.5)
  6.115(1H, d, Dexa-H-4)
  5.376(1H, dd, H-2, $J_{2,3}$=3.3, $J_{2,1}$=1.8)
  5.321(1H, dd, H-3, $J_{3,4}$=9.9)
  5.088(1H, dd, H-4, $J_{4,5}$=9.9)
  4.785(1H, d, H-1)
  4.511(1H, d, Dexa-H-21, $J_{gem}$=16.5)
  4.418(1H, d, Dexa-H-21')
  4.380(1H, m, Dexa-H-11)
  4.014(1H, dq, H-5, $J_{5,6}$=6.2)
  3.118(1H, m, Dexa-H-16)
  2.617(1H, m, Dexa-H-6)
  2.157, 2.057, 2.003(3H×3, each s, OAc×3)
  1.548(3H, s, Dexa-H-19)
  1.218(3H, d, H-7')
  1.055(3H, s, Dexa-H-18)
  0.910(3H, d, Dexa-16CH$_3$, $J_{16CH3,16}$=7.3)
FAB(+)MS;665(M+H)$^+$
MP:137–139° C.
IR $v_{max}^{KBr}$cm$^{-1}$ 3430(O–H), 1752(C=O), 1668(C=O)

2) Synthesis of a deprotected derivative of rhamnosyldexamethasone (synthesis of 119β→120β)

A protected derivative of rhamnosyldexamethasone (119β) (103.4 mg) was dissolved in methanol (1 ml), and to this solution was added 1 M sodium methoxide (40 µl). The mixture was stirred at room temperature for 1 h. The reaction solution was applied to a gel filtration column of LH-20, and eluted with methanol. The solvent of fractions containing product was distilled off in vacuo to give 120β as white powder [55.4 mg (yield 64%)].

Compound 120β
$C_{28}H_{39}FO_9$ MW=538.61
Rf=0.67(silica gel TLC, CHCl$_3$: methanol=1:1)
$^1$H-NMR [500 MHz, CD$_3$OD, Ref=0.000 ppm(TMS)]
δ;7.403(1H, d, Dexa-H-2, $J_{2,1}$=10.3)
  6.286(1H, dd, Dexa-H-1, $J_{1,4}$=1.8)
  6.115(1H, d, Dexa-H-4)
  4.682(1H, d, H-1, $J_{1,2}$=1.5)
  4.649(1H, d, Dexa-H-21, $J_{gem}$=18.3)
  4.412(1H, d, Dexa-H-21')
  4.259(1H, m, Dexa-H-11)
  3.951(1H, dd, H-2, $J_{2,3}$=3.3)
  3.698(1H, dd, H-3, $J_{3,4}$=9.5)
  3.596(1H, dq, H-5, $J_{5,4}$=9.5, $J_{5,6}$=6.2)
  3.383(1H, dd, H-4)
  3.062(1H, m, Dexa-H-16)
  2.713(1H, m, Dexa-H-6)
  2.480(1H, m, Dexa-H-6')
  2.317(1H, m, Dexa-H-12)
  2.222(1H, m, Dexa-H-14)
  1.876(1H, m, Dexa-H-7)
  1.727(1H, m, Dexa-H-15)
  1.580(3H, s, Dexa-H-19)
  1.265(3H, d, H-6)
  1.002(3H, s, Dexa-H-18)
  0.855(3H, d, Dexa-16CH$_3$, $J_{16CH3,16}$=6.9)
FAB(+)MS;539(M+H)$^+$
MP:144–146° C. (decomp.)
IR $v_{max}^{KBr}$cm$^{-1}$ 3418(O–H), 1719(C=O), 1663(C=O)

We claim:

1. A steroid-glycoside compound wherein the steroid aglycon has the formula:

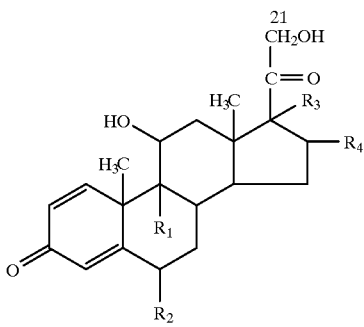

wherein $R_1$ is H or F, $R_2$ is H or F, $R_3$ is H, $CH_3$ or $OR_6$, $R_4$ is H, $CH_3$ or $OR_5$, $R_5$ is H or $COR_6$, and $R_6$ is an alkyl group, and the steroid aglycon has a 21-position which is replaced with a saccharide or acylated derivative of said saccharide in which hydroxyl groups of the saccharide or the acylated derivative of said saccharide are protected with toluoyl, benzoyl, p-chlorobenzoyl or aryl-alkyl group.

2. A steroid-glycoside compound wherein the steroid aglycon comprises difluprednate, diflorasone or diflucortolone and has a 21-position which is replaced with a saccharide or acylated derivative of said saccharide in which hydroxyl groups of the saccharide or the acylated derivative of said saccharide are protected with toluoyl, benzoyl, p-chlorobenzoyl or aryl-alkyl group.

3. A steroid glycoside compound wherein the steroid aglycon comprises dexamethasone, betamethasone or betamethasone valerate and has a 21-position which is replaced with a saccharide or acylated derivative of said saccharide in which hydroxyl groups of the saccharide or the acylated derivative of said saccharide are protected with toluoyl, benzoyl, p-chlorobenzoyl or aryl-alkyl group.

4. A steroid-glycoside compound wherein the steroid aglycon has a 21-position which is replaced with a saccharide or acylated derivative of said saccharide in which hydroxyl groups of the saccharide or the acylated derivative of said saccharide are protected with toluoyl, benzoyl, p-chlorobenzoyl or aryl-alkyl group, wherein the saccharide or acylated derivative of said saccharide is selected from the group consisting of glucose, galactose, mannose, fucose, rhamnose, N-acetylglucosamine, N-acetylgalactosamine, galacturonic acid, glucuronic acid and sialic acid.

5. The steroid-glycoside compound of claim 4, wherein the saccharide or acylated derivative of said saccharide is fucose or rhamnose.

6. Anti-inflammatory drug composition comprising one or more steroid-glycoside compounds wherein the steroid aglycon has a 21-position which is replaced with a saccharide or acylated derivative of said saccharide in which hydroxyl groups of the saccharide or the acylated derivative of said saccharide are protected with toluoyl, benzoyl, p-chlorobenzoyl or aryl-alkyl group.

7. Anti-inflammatory drug composition comprising one or more of the steroid-glycoside compounds of claim 2.

8. Anti-inflammatory drug composition comprising one or more of the steroid-glycoside compounds of claim 3.

9. A method of treating dermatitis comprising administering the anti-inflammatory drug composition of claim 6.

10. A method of treating dermatitis comprising administering the anti-inflammatory drug composition of claim 7.

11. A method of treating dermatitis comprising administering the anti-inflammatory drug composition of claim 8.

12. A method of treating bronchial asthma comprising administering the anti-inflammatory drug composition of claim 6.

13. A method of treating allergic rhinitis comprising administering the anti-inflammatory drug composition of claim 6.

14. A method of treating bronchial asthma comprising administering the anti-inflammatory drug composition of claim 7.

15. A method of treating allergic rhinitis comprising administering the anti-inflammatory drug composition of claim 7.

16. A method of treating bronchial asthma comprising administering the anti-inflammatory drug composition of claim 8.

17. A method of treating allergic rhinitis comprising administering the anti-inflammatory drug composition of claim 8.

18. The method according to claim 9, wherein the anti-flammatory drug composition is administered as an ointment, cream, lotion or tape.

19. The method according to claim 12, wherein the anti-inflammatory drug composition is administered intra-orally or intra-nasally.

20. The method according to claim 13, wherein the anti-inflammatory drug composition is administered intra-orally or intra-nasally.

21. A steroid-glycoside compound wherein the steroid aglycon has the formula:

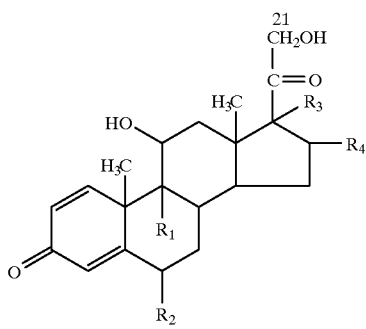

wherein $R_1$ is H or F, $R_2$ is H or F, $R_3$ is H, $CH_3$ or $OR_5$, $R_4$ is H, $CH_3$ or $OR_5$, $R_5$ is H or $COR_6$, and $R_6$ is an alkyl group, and the steroid aglycon has a 21-position which is replaced with a saccharide or acylated derivative of said saccharide in which hydroxyl groups of the saccharide or the acylated derivative of said saccharide are protected with toluoyl group.

* * * * *